US011446008B2

(12) United States Patent
Mehanian et al.

(10) Patent No.: US 11,446,008 B2
(45) Date of Patent: Sep. 20, 2022

(54) AUTOMATED ULTRASOUND VIDEO INTERPRETATION OF A BODY PART WITH ONE OR MORE CONVOLUTIONAL NEURAL NETWORKS

(71) Applicant: Tokitae, LLC, Bellevue, WA (US)

(72) Inventors: Courosh Mehanian, Redmond, WA (US); Sourabh Kulhare, Bellevue, WA (US); Xinliang Zheng, Issaquah, WA (US); Benjamin K. Wilson, Snoqualmie, WA (US)

(73) Assignee: Tokitae LLC, Bellevue, WA (US)

( * ) Notice: Subject to any disclaimer, the term of this patent is extended or adjusted under 35 U.S.C. 154(b) by 288 days.

(21) Appl. No.: 16/540,759

(22) Filed: Aug. 14, 2019

(65) Prior Publication Data

US 2020/0054306 A1 Feb. 20, 2020

Related U.S. Application Data

(60) Provisional application No. 62/719,429, filed on Aug. 17, 2018.

(51) Int. Cl.
*A61B 8/08* (2006.01)
*G06T 7/00* (2017.01)
(Continued)

(52) U.S. Cl.
CPC ............ *A61B 8/5207* (2013.01); *A61B 8/486* (2013.01); *G06F 17/18* (2013.01); *G06K 9/628* (2013.01); *G06K 9/6218* (2013.01); *G06K 9/6277* (2013.01); *G06N 3/082* (2013.01); *G06N 3/084* (2013.01); *G06N 5/046* (2013.01);

(Continued)

(58) Field of Classification Search
CPC .... A61B 8/5207; G16H 50/20; G06T 7/0012; G06T 2207/10132; G06K 2209/05
See application file for complete search history.

(56) References Cited

U.S. PATENT DOCUMENTS 9,277,877 B2 3/2016 Burlina et al.
2009/0041325 A1 2/2009 Luo
(Continued)

OTHER PUBLICATIONS

Cao, Zhantao, et al. "Breast tumor detection in ultrasound images using deep learning." International Workshop on Patch-based Techniques in Medical Imaging. Springer, Cham, 2017. (Year: 2017).*

(Continued)

*Primary Examiner* — Vincent Rudolph
*Assistant Examiner* — Raphael Schwartz
(74) *Attorney, Agent, or Firm* — AEON Law, PLLC; Adam L. K. Philipp; Shan Liao

(57) ABSTRACT

In an embodiment, an intelligent system includes an electronic circuit configured to execute a neural network, to detect at least one feature in an image of a body portion while executing the neural network, and to determine a respective position and a respective class of each of the detected at least one feature while executing the neural network. For example, such a system can execute a neural network to detect at least one feature in an image of a lung, to determine a respective position within the image of each detected feature, and to classify each of the detected features as one of the following: A-line, B-line, pleural line, consolidation, and pleural effusion.

22 Claims, 24 Drawing Sheets

(51) Int. Cl.
*G06T 7/70* (2017.01)
*G06K 9/62* (2022.01)
*G06N 3/08* (2006.01)
*G06N 5/04* (2006.01)
*G06F 17/18* (2006.01)
*G16H 50/20* (2018.01)

(52) U.S. Cl.
CPC .............. *G06T 7/0012* (2013.01); *G06T 7/70* (2017.01); *G16H 50/20* (2018.01); *G06T 2207/10132* (2013.01); *G06T 2207/20084* (2013.01); *G06T 2207/30061* (2013.01)

(56) References Cited

U.S. PATENT DOCUMENTS

| | | | |
|---|---|---|---|
| 2013/0004044 A1 | 1/2013 | Ross et al. | |
| 2013/0197370 A1 | 8/2013 | Burlina et al. | |
| 2016/0239959 A1* | 8/2016 | Blackbourne | G06T 7/0012 |
| 2017/0086790 A1* | 3/2017 | Halmann | A61B 8/0858 |
| 2017/0358078 A1 | 12/2017 | Hoff et al. | |
| 2018/0053300 A1* | 2/2018 | Podilchuk | G06T 7/223 |
| 2018/0114317 A1 | 4/2018 | Song et al. | |
| 2020/0043602 A1* | 2/2020 | Kim | G06N 20/00 |
| 2020/0060642 A1* | 2/2020 | Raju | A61B 8/13 |

OTHER PUBLICATIONS

PCT International Search Report; International App. No. PCT/US2019/046917; dated Dec. 5, 2019; pp. 1-3.
Akaike, H.; "A new look at the statistical model identification"; Dec. 1974; IEEE Transactions on Automatic Control; vol. 19, No. 6; pp. 716-723.
Parthasarathy, "A Brief History of CNNs in Image Segmentation: From R-CNN to Mask R-CNN", Apr. 22, 2017, pp. 1-23, www.blog.athelas.com.
Schwarz, "Estimating the Dimension of a Model", The Annals of Statistics, pp. 461-464, 1978, vol. 6, No. 2, www.jstor.org.
Wikipedia; "Automatic image annotation"; Found at https://en.wikipedia.org/wiki/Automatic_image_annotation Retrieved on Jan. 24, 2019; pp. 1-6.
Extended European Search Report and Written Opinion; EP Patent Application No. 19849345.4; dated May 4, 2022; 11 pages.

* cited by examiner

AUTOMATED ULTRASOUND VIDEO INTERPRETATION OF A BODY PART WITH ONE OR MORE CONVOLUTIONAL NEURAL NETWORKS

CROSS-RELATED APPLICATION(S)

This application claims benefit of priority to U.S. Provisional Patent Application Ser. No. 62/719,429, titled "Automated Ultrasound Video Interpretation Of A Body Part, Such As A Lung, With One Or More Convolutional Neural Networks Such As A Single-Shot-Detector Convolutional Neural Network," which was filed 17 Aug. 2018, and which is incorporated by reference.

This invention was made with Government support under Agreement No. HR0011-17-3-001, awarded by DARPA. The Government has certain rights in the invention.

SUMMARY

Today, ailments, such as pulmonary (i.e., lung-related) ailments, are diagnosed by a doctor, such as a pulmonologist, or other medical professional, after he/she considers medical images, such as one or more medical images of one or both lungs taken by, e.g., x-ray, CAT, PET, and ultrasound.

Although the below discussion and embodiments are directed to ultrasound images, both still images and a time sequence/stream of multiple images (e.g., a video or a video stream), it is understood that the below discussion, described embodiments, and described techniques can be used for medical images other than ultrasound images.

To make his/her diagnosis regarding a pathology of a subject's lungs, a pulmonologist looks for features in one or more ultrasound images, such features including pleural line and absence of lung sliding along the pleural line, A-lines, B-lines, pleural effusion, consolidation, and merged B-lines.

Referring to FIG. 1, the pleural line 10 corresponds to the tissue structure formed by the visceral and parietal pleurae, and the pleural cavity 12 between these pleurae. The visceral pleura 14 is the "inner" pleura, which is the serous membrane that covers the surface of a lung 16 and that dips into the tissues between the lobes of the lung. The parietal pleura 18 is the "outer" serous membrane that attaches the lung 16 to the inner surface 20 of the thoracic cavity. In the pleural cavity 12 between the visceral 14 and parietal 18 pleurae is a "slippery" liquid that allows the pleurae to slide back and forth past one another as the diaphragm (the "breathing muscle," not shown in FIG. 1) contracts and relaxes to expand and compress the lung 16, and, therefore, to cause the inhalation and the expiration phases of respiration.

A lack of sliding of the visceral pleura 14 relative to the parietal pleura 18 can indicate to the pulmonologist (not shown in FIG. 1) a problem such as pneumothorax (collapsed lung). Pneumothorax is a condition where air is trapped in the pleural cavity 12 between visceral pleura 14 and the parietal pleura 18 of the lung. Pneumothorax is a serious condition and intervention is usually indicated. When a patient with a normal lung respires, the visceral pleura 14 and the parietal pleura 18 slide across each other. This relative motion of the two pleura 14 and 18 is observable in a lung ultrasound video. A lung ultrasound video of a subject with pneumothorax does not exhibit lung sliding because the high-impedance contrast of the trapped air prevents the observation of relative pleural movement.

Still referring to FIG. 1, A-lines 22 are an echo artifact of ultrasound that, by themselves, indicate the presence of air in the lung. Echoes are multiple discrete reflections (e.g., "bouncing" between two impedance boundaries like the transducer head and liquid in tissue, where the delay of a bounced signal shows up as a "ghost" object at an integer multiple of the distance between the two impedance boundaries), whereas reverberation is a continuous signal caused by, for example, a signal "bouncing around" inside a water droplet and showing multiple closely spaced "ghost" objects (e.g., B-lines, see FIG. 5) due to the reverb delay, which is typically, although not necessarily, shorter than an echo delay. The presence of A-lines 22 typically indicates a high confidence that the tissue in which the A-lines appear is normal. But the absence of A-lines 22, by itself, does not indicate a pathology.

Still referring to FIG. 1, A-lines 22 typically manifest, in an ultrasound image, as artifacts/lines that are effectively parallel to the transducer (not shown in FIG. 1) face, i.e., that are parallel (for a flat, hereinafter linear, transducer), or circumferential (for a round, hereinafter curvilinear, transducer), lines. When an ultrasound wavefront is incident on the pleura 14 or 18, the pleura redirects a portion of the ultrasound wave back to the ultrasound transducer. The transducer receives a portion of this first redirected wave, and, in response, generates, in the ultrasound image, a bright line, which is the pleural line 10. But the transducer redirects another portion of the first redirected wave back into the body due to the impedance mismatch at the skin/transducer boundary. When this second redirected wave is incident on the pleura 14 or 18, the pleura redirects a portion of this second redirected wave back to the transducer. The ultrasound machine (not shown in FIG. 1) is "dumb" in that it merely measures a time delay from the generation of a wave front to the receiving of a redirected wave front, translates the time delay into a distance, and displays a bright spot/line at the distance in the ultrasound image. That is, the ultrasound machine cannot distinguish an echo from a true first redirection of the wavefront. Therefore, because the delay between generation of the wavefront and receiving the redirected portion of the second redirected wave is twice the delay between generation of the wave front and receiving the redirected portion of the first redirected wave (from the pleura 14 or 18), the ultrasound machine generates a second bright line at twice the distance of the first line, i.e., at twice the distance from the true pleura distance. This redirection phenomena continues such that the ultrasound image has a series of A lines 22, which are separated by the distance between the transducer and the pleura 14 or 18. So, the pulmonologist (not shown in FIG. 1) knows that the first line is the true pleural line 10, and the other lines at integer multiples of the pleura 14 or 18 distance are A-lines 22, which are really image artifacts, but which do indicate the presence of air in the pleural cavity 10 (abnormal), or just behind the pleura 14 (normal). Although the lack of, or dimmer, A-lines 22 may indicate that there is little or no air in or just behind the pleura 14, associating the lack of, or dimmer, A-lines with an abnormality concerning the lung 16 is not commonly accepted in the medical literature or in the medical community. That is, it is not commonly acceptable to diagnose a pathology of the lung 16 based solely on the lack of, or dim, A-lines 22.

Referring to FIG. 2 and to FIG. 14, B-lines 24 are an artifact of ultrasound reverberation caused by liquid/air interfaces inside of the lung, and the presence of B-lines may indicate a lung condition (e.g., pneumonia, acute respiratory distress syndrome (ARDS)) characterized by excess liquid in a portion of the lung. A small number, or a total absence, of B-lines 24 is typically indicative of normal levels of liquid in the lung tissue. B-lines 24 show up in an ultrasound image as artifacts/lines that are perpendicular to the transducer face (not shown in FIGS. 2 and 14) if the transducer is a linear transducer, and as lines that extend radially outward from a curvilinear transducer (not shown in FIGS. 5 and 14).

Referring to FIGS. 3-5 and FIG. 17, pleural effusion 30 is characterized by an accumulation of excess fluid within the pleural cavity 12 (i.e., the space between the visceral pleura 14 and the parietal pleura 18). In severe cases, a pulmonologist, or other doctor or clinician, may need to perform an intervention, such as therapeutic aspiration to drain the fluid. In an ultrasound image, pleural effusion 30 shows up as dark regions along, or adjacent to, the pleural line 10, and can be graded as, e.g., low severity, medium severity, and high severity.

Referring to FIG. 6, consolidation 60 is characterized by a grouping of bright spots in the lung 16, beyond the pleural line 10, and can indicate liquid in the lung (ultrasound wave reflects from the air/fluid interfaces). The size of the consolidation 60 is related to the severity of the potential liquid buildup in the lung tissue.

And referring to FIG. 7, a phenomenon similar to consolidation 60 of FIG. 6 is a merger 62 of B-lines 24, in which multiple, closely spaced B-lines are found in the region below the pleural line 10. A merger 62 of B-lines 24 can indicate liquid buildup more serious than that indicated by a single B-line. The number of B-lines 24 in a merger 62 of B-lines, and the separation between adjacent ones of the B-lines, are related to the severity of the potential liquid buildup.

Referring to FIGS. 1-7, a problem with needing a pulmonologist to interpret ultrasound images is that in many regions of the world, such as in low-resource nations and in other economically underdeveloped regions, skilled pulmonologists are often scarce or unavailable.

Furthermore, even where a skilled pulmonologist is available, it may be desirable to provide an intelligent system to assist the pulmonologist in making a diagnosis, and to increase the chances that the pulmonologist's diagnosis is correct.

In an embodiment, such an intelligent system includes an electronic circuit configured to execute a neural network, to detect at least one feature in an image of a body portion while executing the neural network, and to determine a respective position and a respective class of each of the detected at least one feature while executing the neural network.

For example, such a system can execute a neural network to detect at least one feature in an image of a lung, to determine a respective position within the image of each detected feature, and to classify each of the detected features as one of the following: A-line, B-line, pleural line, consolidation, and pleural effusion.

In another embodiment, such an intelligent system includes an electronic circuit configured to execute a classifier neural network, to receive an image of a body portion, and to determine, while executing the classifier neural network, a probability that the image indicates a state of a function of the body portion, the function belonging to a particular class.

For example, such a system can receive a sequences of images of a lung, such as a video stream of images of a lung or a conventional M-mode image of a lung, and execute a classifier neural network to determine a probability that the image indicates that the lung exhibits, or does not exhibit, lung sliding.

In yet another embodiment, such an intelligent system includes an electronic circuit configured to execute a neural network having input channels, and configured, while executing the neural network, to receive each of an image of a body portion and at least one modified version of the image with a respective input channel, to detect at least one feature in the image in response to the image and the at least one modified version of the image, and to determine a respective position and a respective class of each of the detected at least one feature in response to the image and the at least one modified version of the image.

For example, the at least one modified version of the image can be a filtered version of the image to enhance the electronic circuit's ability to detect one or more features in the image.

In still another embodiment, such an intelligent system includes an electronic circuit configured to execute a neural network and configured to receive an image of a body portion, the image including at least one feature belonging to a class, and, while executing the neural network, to detect at least one feature in the image, and to determine, for each of the detected at least one feature, a respective position and a respective confidence level that the respective one of the detected at least one feature belongs to the class.

And an embodiment of a system for training a neural network includes an electronic circuit configured to generate, from each of at least one first training image, at least one second training image, and to train the neural network by executing the neural network to determine a respective probability that each of at least one feature in at least one of the at least one first training image and the at least one second training image belongs to a feature class, by determining, for each of the at least one feature, a probability difference between the determined respective probability and a corresponding annotated probability, and by changing a respective weighting of each of at least one synapse of the neural network in response to the probability difference.

DETAILED DESCRIPTION

In general, an embodiment described herein has at least the following three aspects, in which feature/object identification and classification can be the same operation or separate operations:

1) Using one or more convolutional neural networks (CNNs), or one or more other neural networks (NNs), to detect, to identify/classify features/objects in an ultrasound image (or in a series of ultrasound images) of a lung, such features including, or corresponding to, pleural line and absence of lung sliding along the pleural line (hereinafter "absence of lung sliding," "presence of lung sliding," without the phrase "along the pleural line"), A-lines, B-lines, pleural effusion, consolidation, and merger of B-lines (hereinafter merged B-lines)—as described below, determining whether or not a series, or video, of ultrasound images indicates the absence or the presence of lung sliding typically is a classification problem only, and does not entail feature detection;

2) Training the one or more CNNs, or one or more other NNs, to perform aspect (1); and 3) Rendering a diagnosis based on the features/objects detected, and identified/classified in aspect (1).

Other embodiments include improving M-mode image generation from ultrasound video images of the lung and selecting the trained NN model(s) to use for aspect (1).

Figure 8:
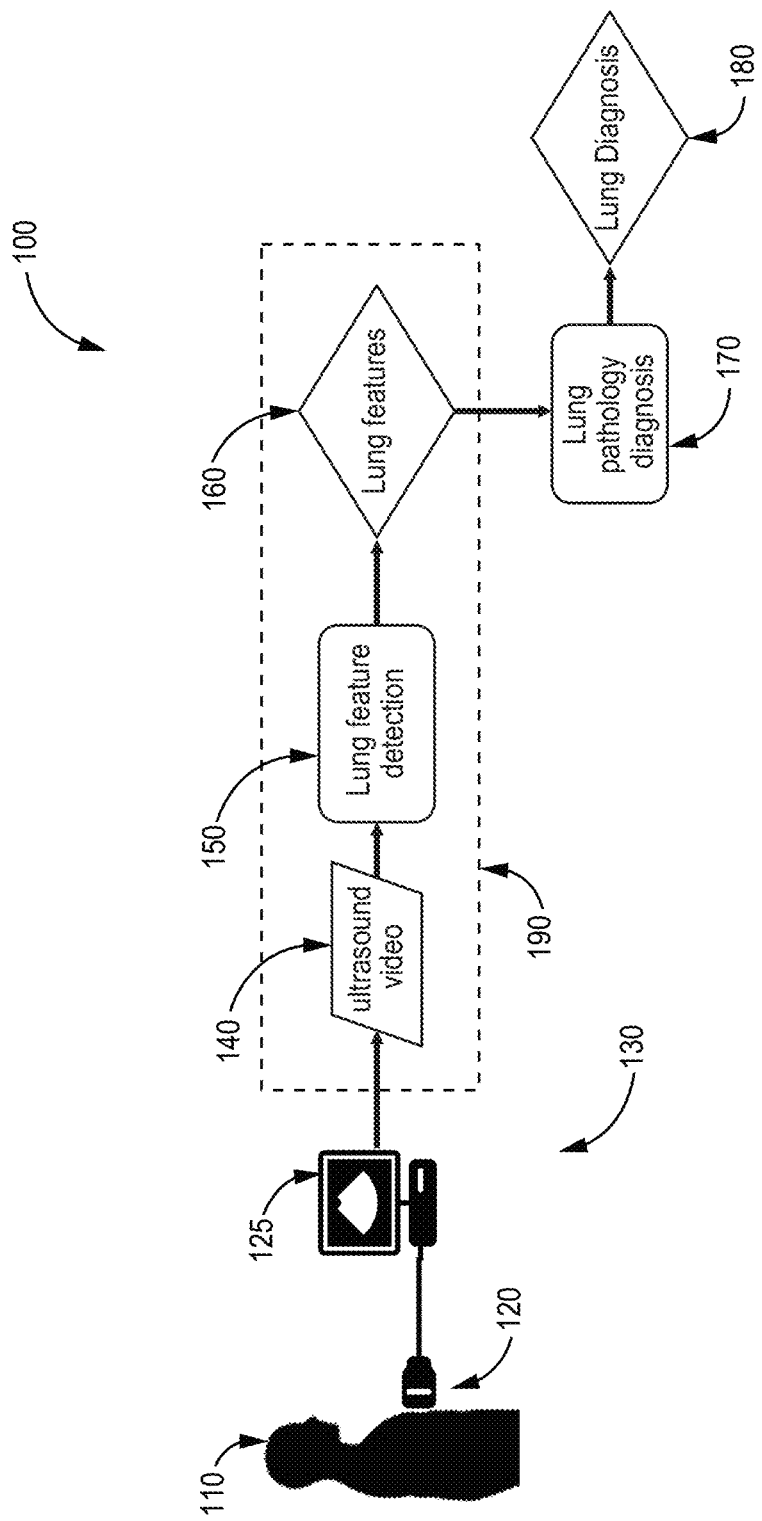
FIG. 8 is a workflow of an ultrasound-image-of-a-lung acquisition, of an ultrasound-image-of-a-lung analysis, and of a lung diagnosis, according to an embodiment.

FIG. 8 is a workflow 100 of an acquisition of an ultrasound image of a lung, an analysis of the acquired ultrasound image of the lung, and a lung diagnosis based on the analysis, and includes a diagram of an ultrasound system 130, according to an embodiment. In FIG. 8, rectangular boxes are processing steps; and diamonds are determined and provided (e.g., displayed) results.

There are two processing steps in FIG. 8:

(1) Lung-feature-detection processing step 150. The output of the processing step 150 include those of the following feature/objects that the ultrasound system 130 detects in an analyzed image: A-Line, pleural line, B-line, merged B-lines, absences of lung sliding, consolidation, and pleural effusion.

(2) Lung-pathology-diagnosis processing step 170. The output of the processing step 170 is the lung diagnosis 180, e.g., pneumothorax, pneumonia, pleural effusion, or ARDS (Acute Respiratory Distress Syndrome).

The ultrasound system 130 includes an ultrasound transducer 120 coupled to an ultrasound machine 125; the ultrasound system is described in more detail below in conjunction with FIG. 24.

An ultrasound technician, also called a sonographer (not shown in FIG. 8), manipulates the ultrasound transducer head 120 over the chest of a subject 110 to generate a time sequence of ultrasound images, i.e., to generate ultrasound video.

The ultrasound machine 125, which can be, or which can include, a conventional computer system, and which can execute software, or which can be configured with firmware, that causes the computer system to process the ultrasound images as follows.

First, the machine 125 is configured to use conventional techniques, including image-filtering and other image-processing techniques, to render enhanced ultrasound video 140 (see FIG. 13), such as B-mode ultrasound video.

Then, referring to a step 150, the ultrasound machine 125 executes a CNN, such as a Single Shot Detection (SSD) CNN, that detects and identifies features/objects in one or more frames of the ultrasound video 140, such features/objects including, or representing, pleural line, A-lines, B-lines, pleural effusion, consolidation, and merged B-lines. Furthermore, because lung sliding is a classification problem only (lung sliding is either present in an M-mode image (see below) or not present in the M-mode image), an SSD CNN is not used to detect lung sliding in an M-mode image; instead, a classification algorithm, such as a classic CNN, is used to identify/classify lung sliding as being present in, or absent from, an M-mode image. Furthermore, hereinafter "features" and "objects" in an image, such as an ultrasound image, are considered to be equivalent terms, and, therefore, are used interchangeably. Moreover, hereinafter "identify" and "classify" features in an image such as an ultrasound image, are considered to be equivalent terms, and, therefore, are used interchangeably.

Next, at a step 170, the ultrasound machine 125 executes a diagnosis algorithm that evaluates the classified lung features to render a lung-pathology diagnosis 180. For example, such a pathology diagnosis is in response to the determined likelihood of the presence, and the respective severities, of conditions such as less-than-normal, or absence of, lung sliding, A-line, B-line, pleural effusion, consolidation, and merged B-line.

Examples of the lung diagnosis 180 include pneumonia, collapsed lung, and ARDS.

Figure 9:
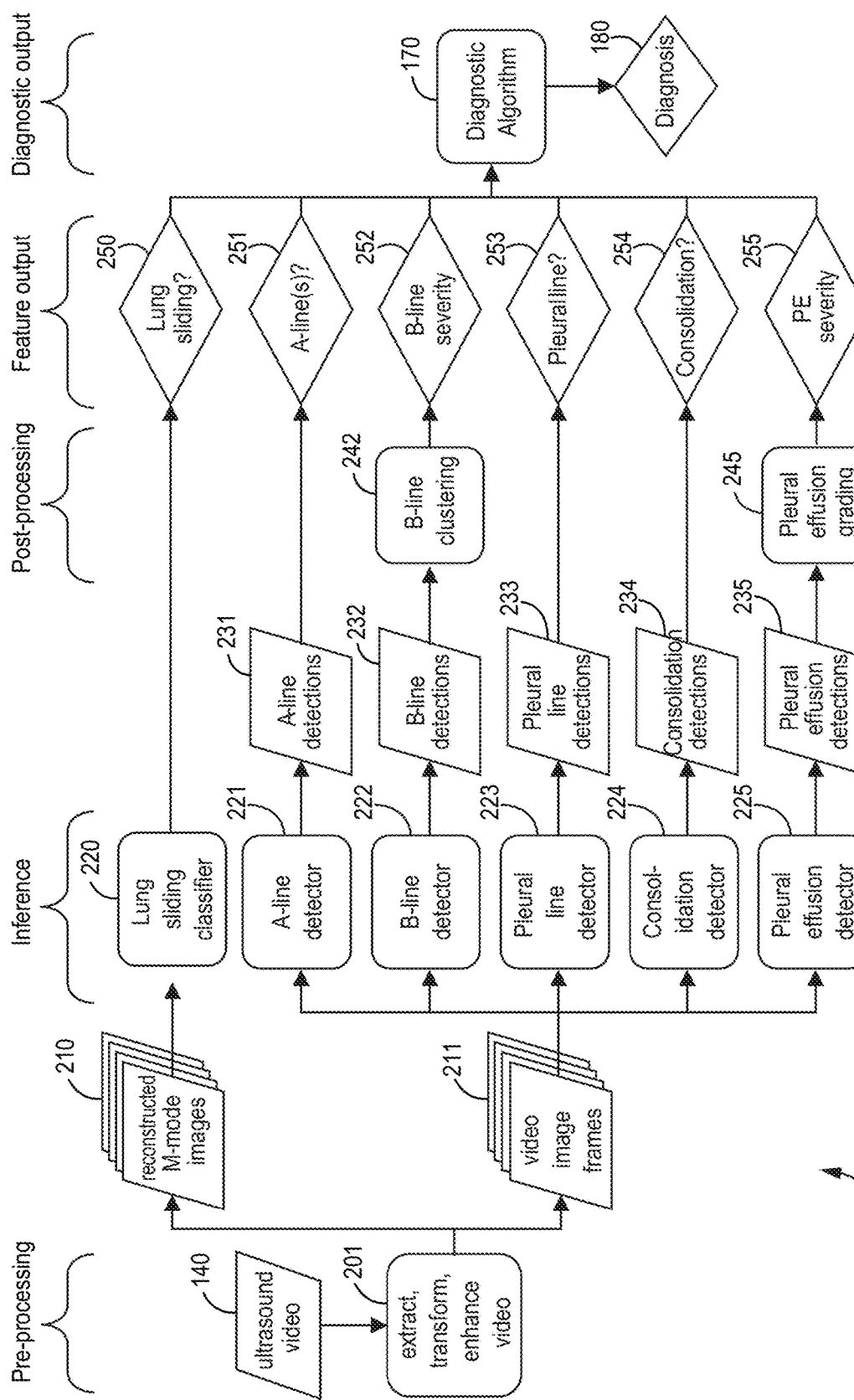
FIG. 9 is a more detailed diagram of the workflow of the ultrasound-image-of-a-lung acquisition, of the ultrasound-image-of-a-lung analysis, and of the lung diagnosis, of FIG. 8, according to an embodiment.

FIG. 9 is a workflow 200 with additional steps and results, and more detail of steps and results 150, 160, 170, and 180 of FIG. 8, according to an embodiment that is referred to as single-class embodiment for reasons explained below. In the embodiment shown in FIG. 9, the ultrasound machine 125 (FIG. 8) executes a classification CNN to classify lung sliding in M-mode images 210. The ultrasound machine 125 executes five single-class SSD CNNs to detect and to classify each of another five features A-line, B-line, pleural line, consolidation, and pleural effusion, respectively (see the column labeled "Inference" in FIG. 9); therefore, the workflow 200 can be referred to as a single-class SSD CNN embodiment, or, more generally, as a single-class CNN embodiment. And details of how a CNN, particularly an SSD CNN, operates are described further below.

At a step 201, the ultrasound machine 125 (FIG. 8) pre-processes ultrasound video images 140 by transforming and enhancing the images. The ultrasound machine 125 (a) extracts a plurality of image frames 211 from the ultrasound video 140, (b) optionally applies one or more geometric transforms to the image frames, (c) optionally enhances the image frames, and (d) generates one or more reconstructed M-mode images 210 from the pre-processed video. The extraction of the image frames 211 from the ultrasound video 140 is conventional and, therefore, is not described further.

Two types of ultrasound transducers 120 (FIG. 8) are generally used for pulmonary applications. Curvilinear transducers are typically used for adults, and linear transducers for children. Curvilinear transducers produce fan-shaped output images as shown, for example, in FIGS. 10 and 12, whereas linear transducers produce rectangular output images (not shown). A fan-shaped output image may be described by a polar coordinate system, and a rectangular output image may be described by ordinary Cartesian coordinates. In an embodiment, the ultrasound machine 125 (FIG. 8), at the step 201, converts polar output from a curvilinear transducer to a rectangular output, and in another embodiment, converts rectangular output from a linear transducer to a polar output. Enhancement of images is described below.

Figure 10:
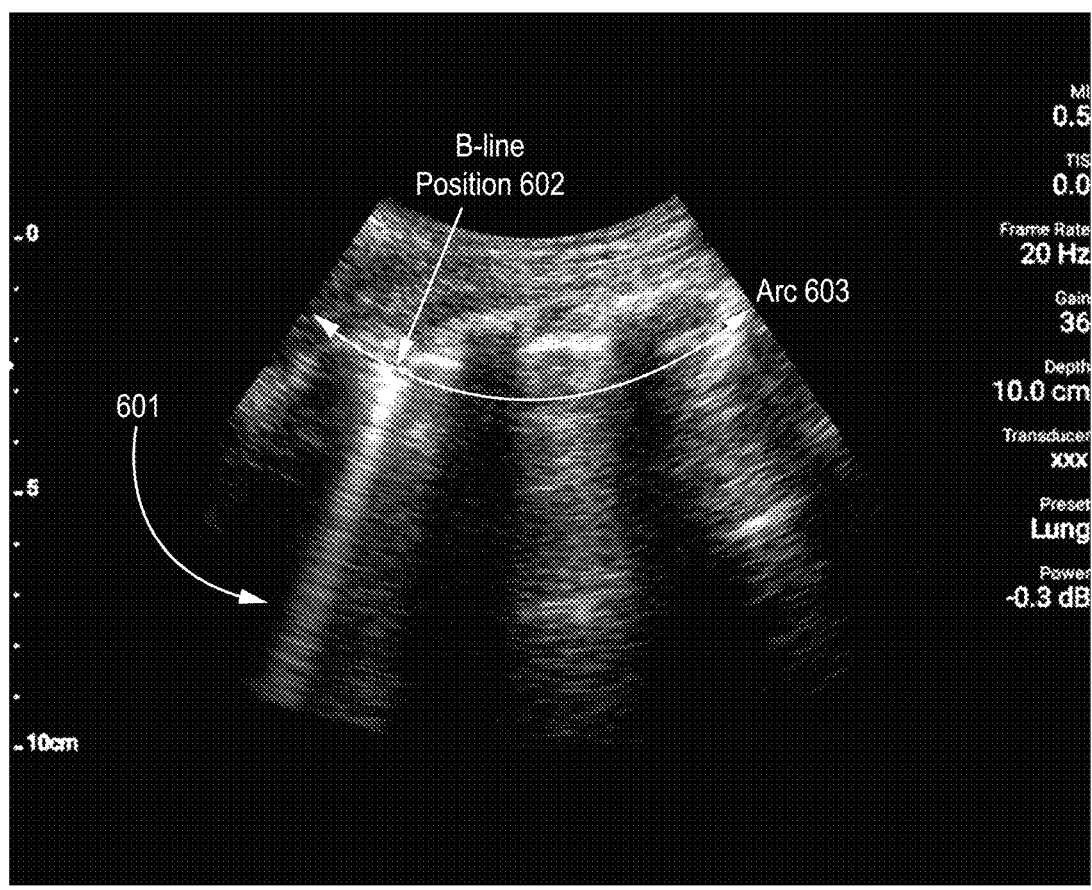
FIG. 10 is an ultrasound image of a lung, the image produced by a curvilinear ultrasound transducer and including features corresponding to B-lines.

For example, referring to FIGS. 9-10, if the ultrasound transducer 120 (FIG. 8) is a curvilinear transducer, then, at the step 201, the ultrasound machine 125 (FIG. 8) may translate the images 140 from polar coordinates to linear (Cartesian) coordinates. Furthermore, referring to FIG. 11, the ultrasound machine 125 may filter, or apply other image-processing techniques to, the video images 140 to enhance features such as B-lines to make them easier for the CNN to detect and to classify.

Figure 15:
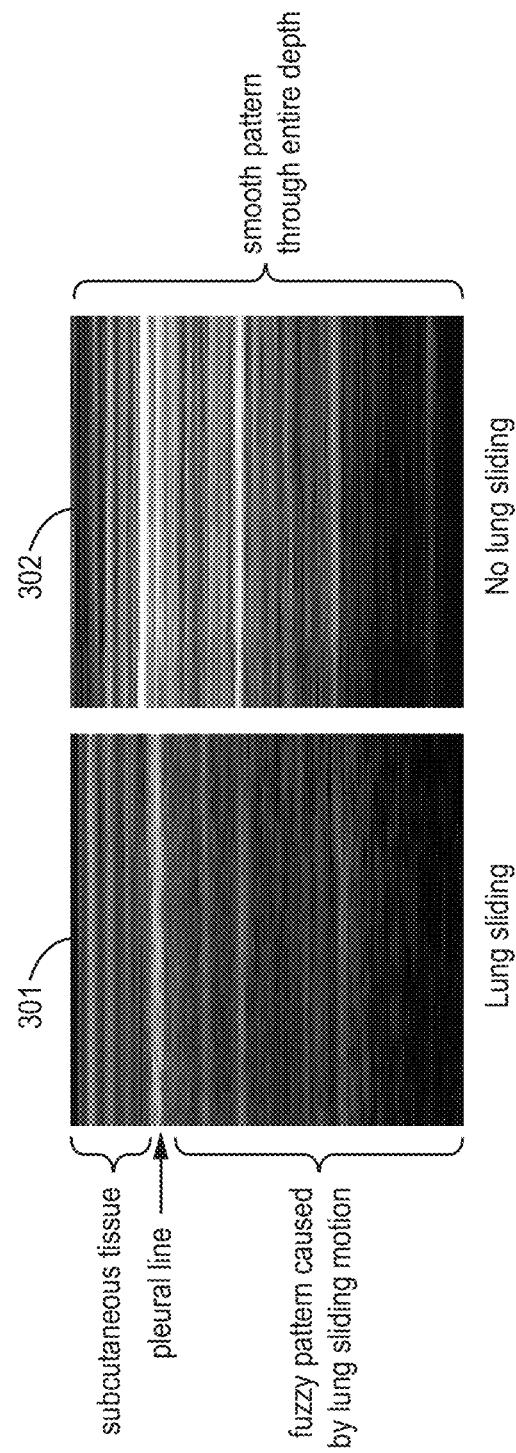
FIG. 15 includes M-mode images that indicate lung sliding along the pleural line (the image on the left) and no lung sliding (the image on the right).

At a step 210, the ultrasound machine 125 reconstructs M-mode images, and effectively provides these images to the lung-sliding classifier 220 to allow the classifier to classify lung sliding. FIG. 15 includes reconstructed ultrasound M-mode images showing a pleural line, the left image 301 indicating lung sliding (fuzziness in the image indicates motion; such lung sliding in an M-mode image is informally called a "seashore pattern"), the right image 302 indicating no lung sliding (smooth, sharper pattern in the image indicates absence of motion; the lack of lung sliding in an M-mode image is informally called a "bar-code pattern"). Therefore, the difference between lung sliding and no lung sliding in a B-mode video is rather subtle and may be hard to discern. Consequently, many commercial ultrasound systems, such as the ultrasound system 130, produce M-mode images, where the distinction between lung sliding and no lung sliding is more obvious. In an M-mode image, the vertical dimension represents depth and the horizontal dimension represents time. An M-mode image can be likened to a video camera that captures only a vertical slice of the field of view, one pixel wide and where these vertical slices are stacked horizontally to form an image. Like a conventional ultrasound device, the ultrasound system 130 (FIG. 8) produces an M-mode image by recording the returned ultrasound signal at one particular position (e.g., an angular position for a curvilinear transducer, a lateral position for linear transducer) as a function of time. If an M-mode image is needed at another position of the lung, the ultrasound machine 125 conducts a separate M-mode-image capture session at the other position.

Figure 12:
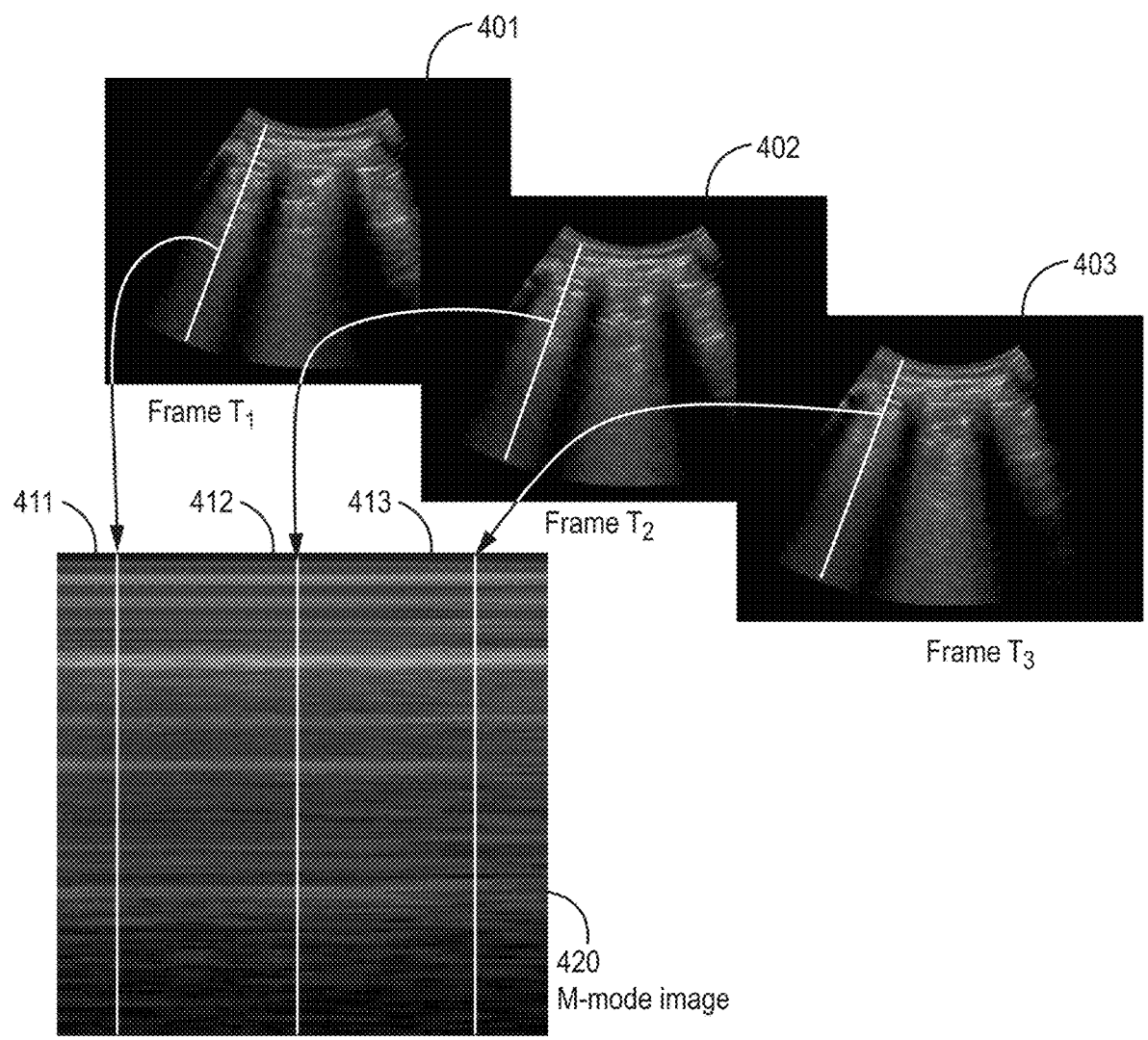
FIG. 12 is an M-mode ultrasound image of a lung, and three of the normal-mode ultrasound images of the lung in response to which the M-mode ultrasound image is generated, according to an embodiment.

Referring to FIG. 12, an M-mode image is described in more detail, according to an embodiment.

"M-mode image" stands for "motion image," which is a time sequence of a single column of pixels of in larger images, where the single column of pixels in each image represents the same location of the tissue (e.g., lung) being imaged.

FIG. 12 includes images showing how M-mode images are constructed. A pixel column of an image is selected and identified with straight vertical line 411 in image 401. In each of subsequent (in time) images 402 and 403, the same pixel column is identified with straight vertical lines 412 and 413, respectively. That is, the image 420 is a time sequence of the same pixel column (actually, of the same region of the tissue being imaged), with the vertical lines 411, 412, and 413 representing the same pixel column at different times (for example, the images 401-403 have undergone a polar-coordinate-to-rectangular-coordinate transformation, or the pixel columns are extracted, and put into a rectangular coordinate system, using radial column extraction). Gray-level differences in the pixel column over time are indicative of lung sliding. Uniformity in the pixel column over time is indicative of reduced or no lung sliding. The ultrasound machine 125 (FIG. 8) is configured to generate and to analyze more than the one pixel column shown in FIG. 12. By analyzing multiple pixel columns, accuracy of lung-sliding detection can be increased at least due to the averaging effect.

For example, still referring to FIG. 12 and to step 210 of the workflow 200 of FIG. 9, the straight lines 411, 412, and 413 each represent a single-column of pixels. In a conventional ultrasound system, a sonographer selects a column for M-mode treatment (e.g., by using a pointing device on the image display), and the ultrasound system thereafter shows M-mode images only of that column. But in an embodiment, the ultrasound system 130 (FIG. 8) can extract, from a sequence of ultrasound images, e.g., from a video stream of ultrasound images, one or more M-mode columns for analysis. That is, instead of displaying only a single column in M-mode as conventional ultrasound machines do, an embodiment of the ultrasound system 130 can generate any number of sequences of M-mode images, up to one respective sequence per pixel column in the ultrasound video images 140. This allows an embodiment of the ultrasound system 130 to perform, efficiently and simultaneously, lung-sliding detection at multiple locations of the pleural line. Where the ultrasound transducer 120 (FIG. 8) is curvilinear so as to generate a "radial" pixel column (the straight lines in the images 401, 402, and 403 of FIG. 12), one way to generate an M-mode image 420 is to convert one or more corresponding ultrasound images, such as ultrasound images 401, 402, and 403, from polar coordinates to rectangular coordinates, such that each slanted pixel column is converted to a vertically straight pixel column 411, 412, and 413, respectively, from which the ultrasound system 130 can generate an M-mode image of the time-sequence at one or more of the straight pixel columns. Another way to generate an M-mode image is to compute the pixel intensities along a radial line (e.g., the slanted lines in images 401, 402, and 403 of FIG. 12) to extract a pixel column from multiple time-sequenced images to form an M-mode image. That is, the ultrasound system 130 uses a radial-pixel-intensity algorithm in place of a polar-coordinate-to-rectangular-coordinate transformation of the ultrasound images to extract of the pixel column from the sequence of coordinate-transformed images.

Still referring to FIG. 9, after the step 201, the ultrasound machine 125 (FIG. 8) effectively provides the transformed and enhanced non-M-mode images 211 to the CNN detectors 221, 222, 223, 224, and 225 for the respective detection of A-line, B-line, pleural line, consolidation, and pleural effusion.

At a step 220, the ultrasound system 130 (FIG. 8) implements a CNN lung-sliding classifier that determines whether the M-mode images 210 exhibit lung sliding. The classifier classifies one or more of the reconstructed M-mode images 210 to determine whether or not there is lung sliding. The classifier that the ultrasound system 130 implements at the step 220 can be any type of machine-learning classifier, including, but not limited to, the following types of machine-learning classifier: logistic regression, support vector machine, k-nearest neighbor, neural network, and deep-learning neural network. In an embodiment, the ultrasound system 130 implements a convolutional neural network (CNN) classifier. The training of such a classifier is described below in conjunction with FIGS. 19-20. The determination of whether or not there is lung sliding is based on classifying several reconstructed M-mode images 210 at various positions in the same ultrasound B-mode video (B-mode video is "normal" video in which the vertical dimension of an image is depth and the horizontal dimension of the image has dimensions of space (e.g., width), not time as does an M-mode image. This has the effect of improving accuracy because of an averaging effect.

In more detail, the CNN lung-sliding classifier determines a likelihood, or a confidence level, that lung sliding exists. The confidence level is a number between 0 and 1. The confidence-level threshold (e.g., 0.5) between whether a feature is likely to exist or is not likely to exist, can be set by a user of the ultrasound system 130 (FIG. 8). If confidence is high (e.g., above the threshold), then lung-sliding probably exists; conversely, if confidence is low (e.g., below the threshold), then lung-sliding probably does not exist. At least some of the details of how the CNN functions to make such a determination are conventional, and, therefore, are not described herein for brevity. Furthermore, other algorithms that the ultrasound machine 125 (FIG. 8) can use in place of the CNN include a feature extractor followed by one or more of a logistic-regression algorithm, a support vector machine, a k-nearest-neighbor algorithm, and one or more other types of neural networks.

Referring again to FIG. 9, at steps 221, 222, 223, 224, and 225, the ultrasound machine 125 executes the respective SSD CNNs to detect and to classify, in the ultrasound images 211, A-lines, B-lines, pleural line, consolidation, and pleural effusion. The detection and classification of each feature are based on a respective confidence level, and include a location, within the image, of the detected and classified feature. A virtue of the single-class embodiment described in conjunction with the workflow 200 of FIG. 9 is that the feature detections are independent of each other and two or more feature detections may trigger at substantially the same location of an image. Therefore, the single-class embodiment can be useful for features such as pleural effusion and pleural line, which tend to be right next to, or on top of, each other in a lung and, therefore, in an ultrasound image of the lung. In the multi-class embodiment in which a single SSD CNN detector, or each of multiple SSD CNN detectors, detects and identifies multiple features, however, two or more features detected at substantially the same location may "compete" with one another such that the ultrasound machine 125 is able to detect only one feature type at a given image location even though, in actuality, there are multiple feature types at the same given location of the image. That is, a multi-class embodiment may eliminate a true detection of some, even all but one, of multiple features that are close to one another in a same ultrasound image. Therefore, from a result-oriented view point, using one single-class SSD CNN for each feature to be detected and classified may be preferred. But because of processing-power limitations (a tablet computer or equivalent) in the geographic regions (e.g., regions far from medical facilities and third-world countries) in which an embodiment of the ultrasound system 130 (FIG. 8) is intended for use, the single-class SSD CNNs may operate sequentially, not in parallel, due to processing-power limitations so that the processing time could be prohibitive. Therefore, from a processing-time point of view, where processing power is limited, a multi-class SSD CNN embodiment may be preferred.

In more detail, in the single-class embodiment described in conjunction with the workflow 200 of FIG. 9, the ultrasound system 130 (FIG. 8) implements a series of five single-class detector modules 221, 222, 223, 224, and 225 to operate on the collection of (pre-processed) video-image frames 211. Each module "looks" for its respective target feature, e.g., A-lines, B-lines, pleural-line, consolidation, and pleural effusion, respectively, in the input video frames 211. Modules 221, 222, 223, 224, and 225 are computer vision-based detectors. In some embodiments, one or more of the modules 221, 222, 223, 224, and 225 are feature detectors of the single-shot type (e.g. SSD or you only look once (YOLO)) or dual-network type (e.g. region (R)-CNN, Fast R-CNN, or Faster R-CNN). The training of the modules 221, 222, 223, 224, and 225 is described below in conjunction with FIGS. 19-20.

Figure 1:
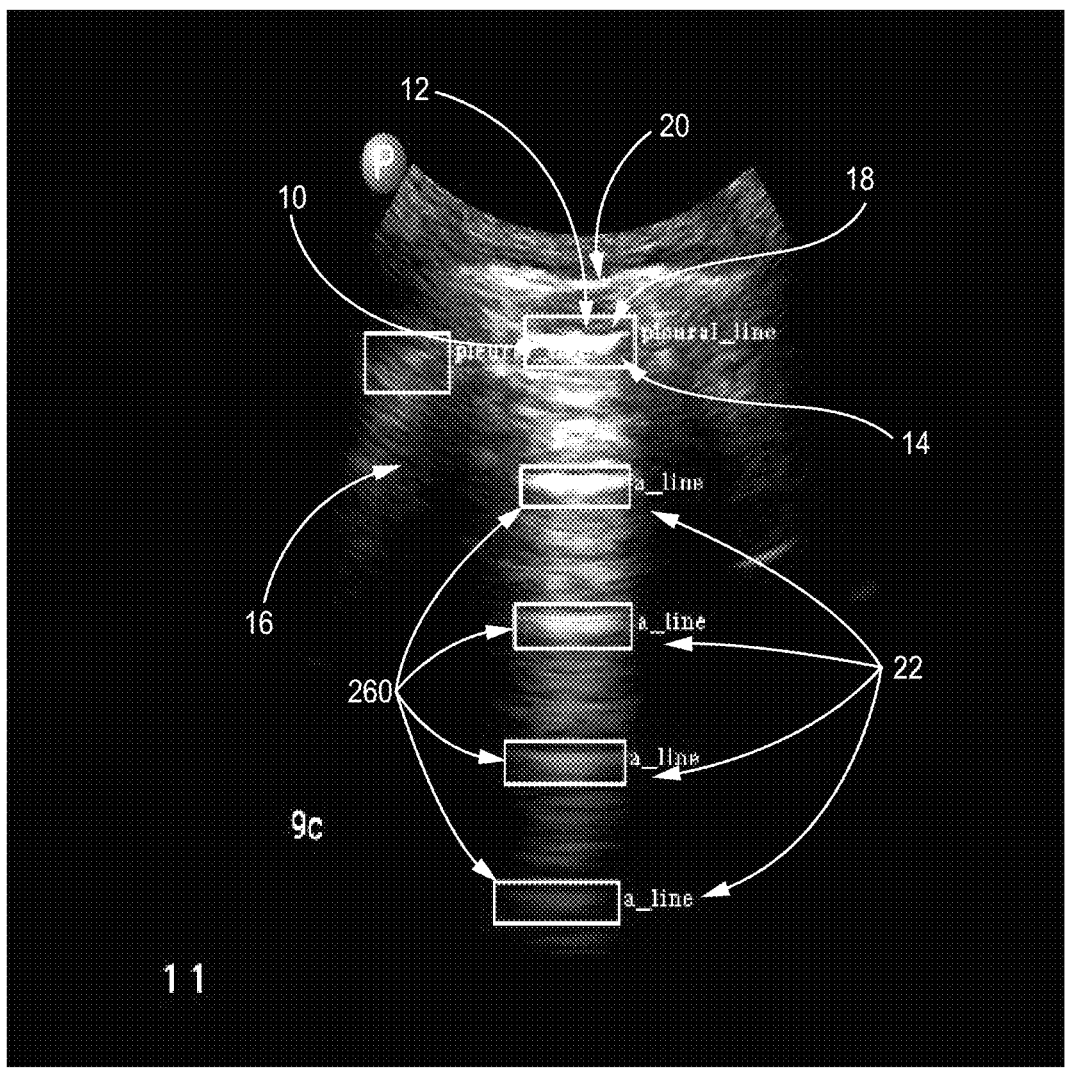
FIG. 1 is an ultrasound image of a lung, the image including features corresponding to a pleural line of the lung and to A-lines.

The output 231 of the module 221 includes one or more detections of A-lines, each detection being represented by five real numbers. The first number is the probability, or confidence level, that the image feature detected is an A-line. The remaining four numbers are, respectively, the <x,y> coordinates of the upper-left corner of the bounding box containing the detected A-line, and the width <$\Delta$x, $\Delta$y> of the bounding box (see, e.g., bounding boxes 260 of FIG. 1).

Figure 2:
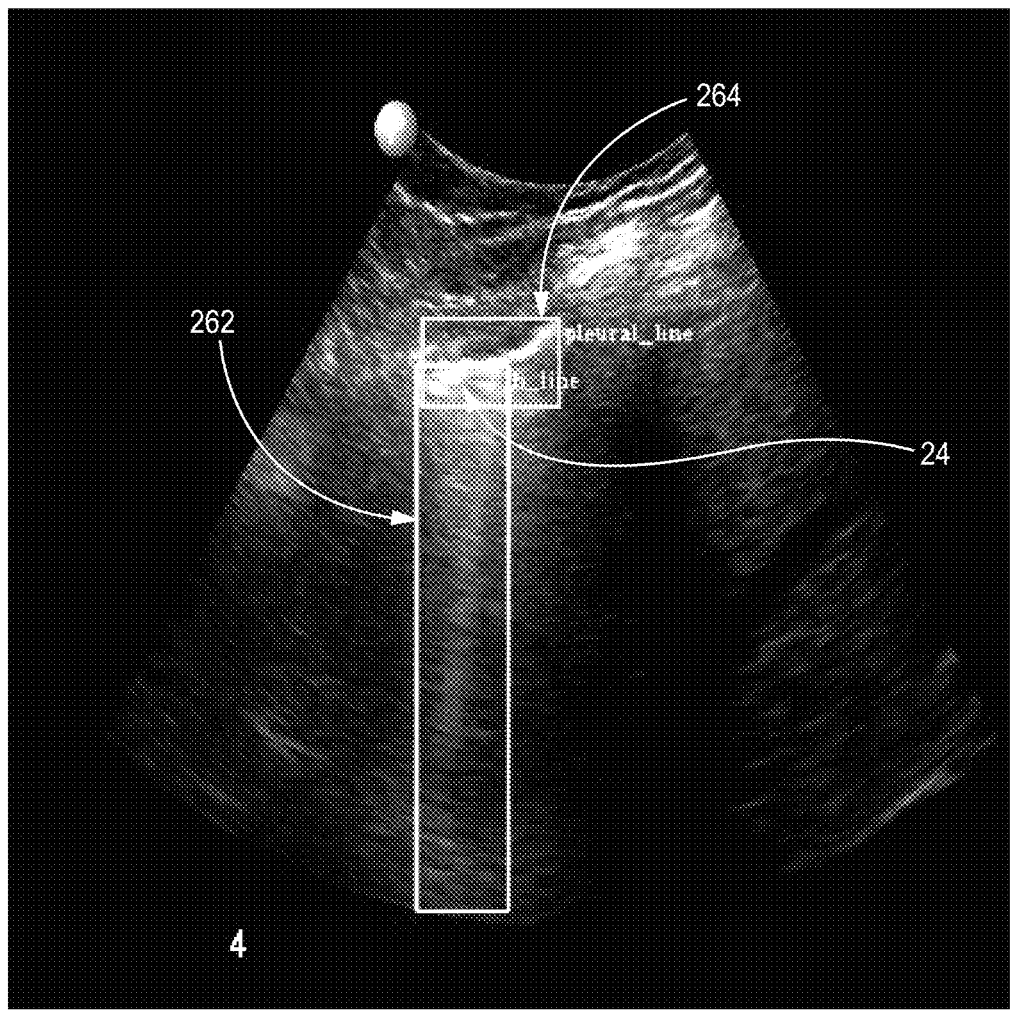
FIG. 2 is an ultrasound image of a lung, the image including features corresponding to a pleural line of the lung and to a B-line.
Figure 3:
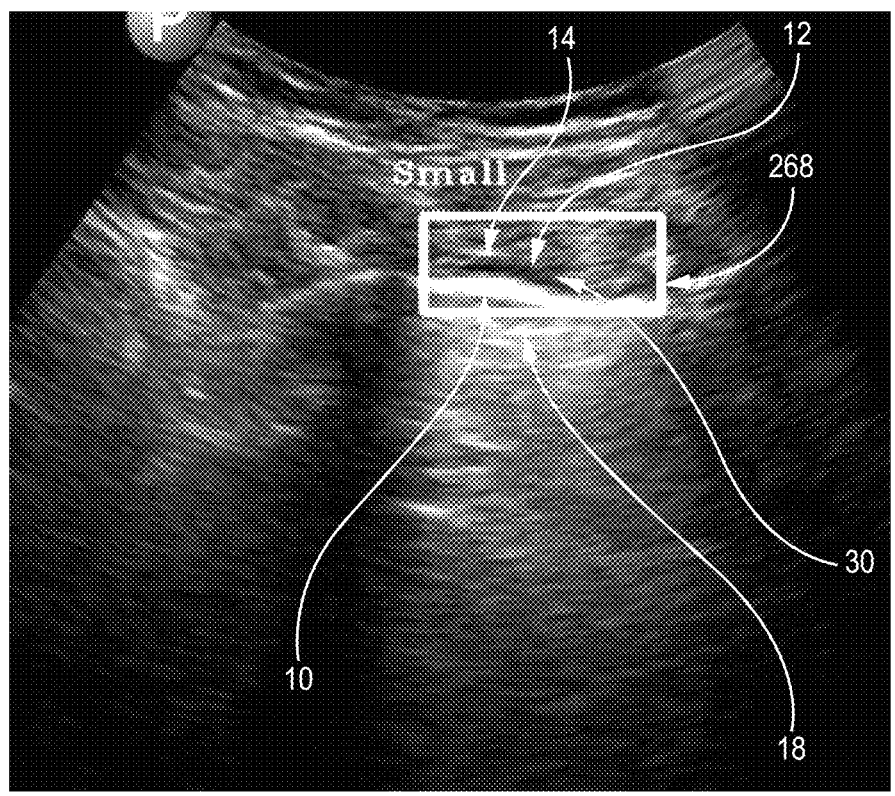
FIGS. 3-5 are respective ultrasound images of a lung, each of the images including features corresponding to a respective pleural effusion.
Figure 4:
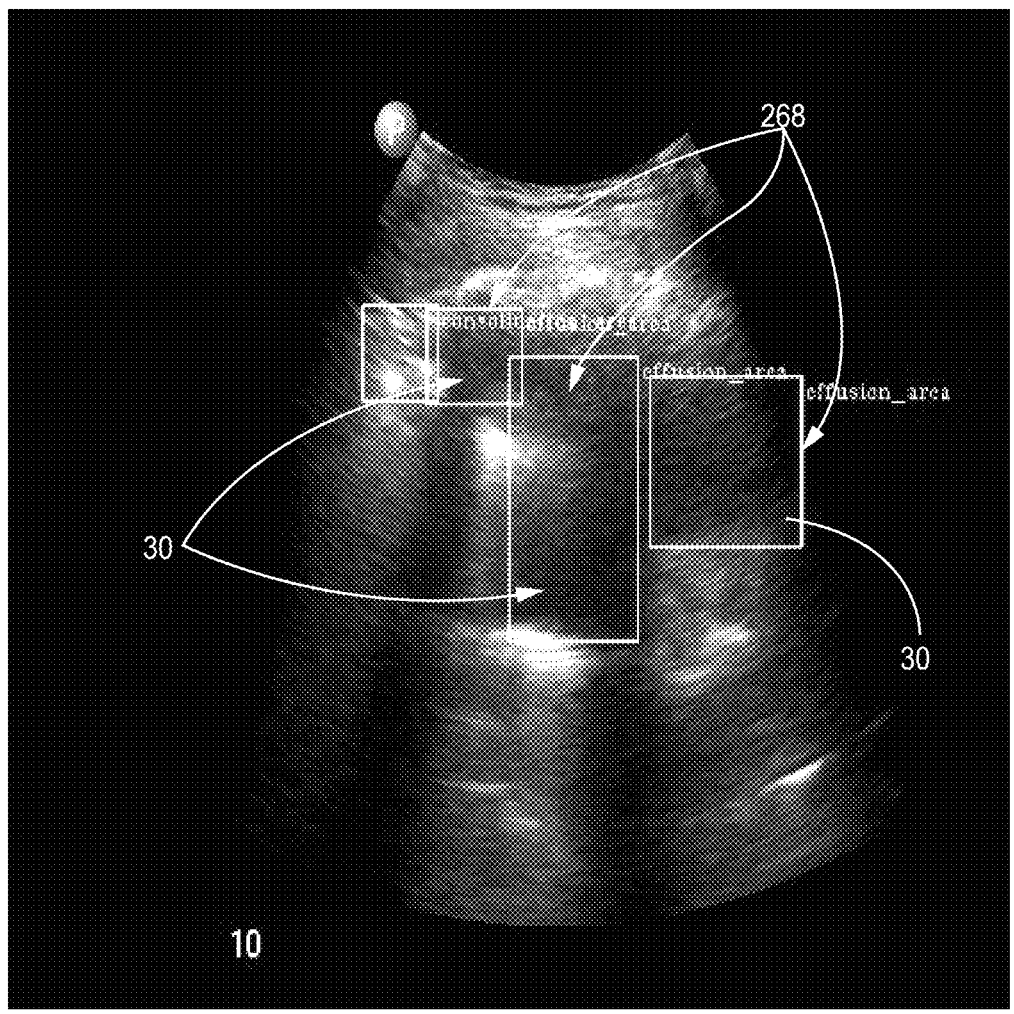
Figure 5:
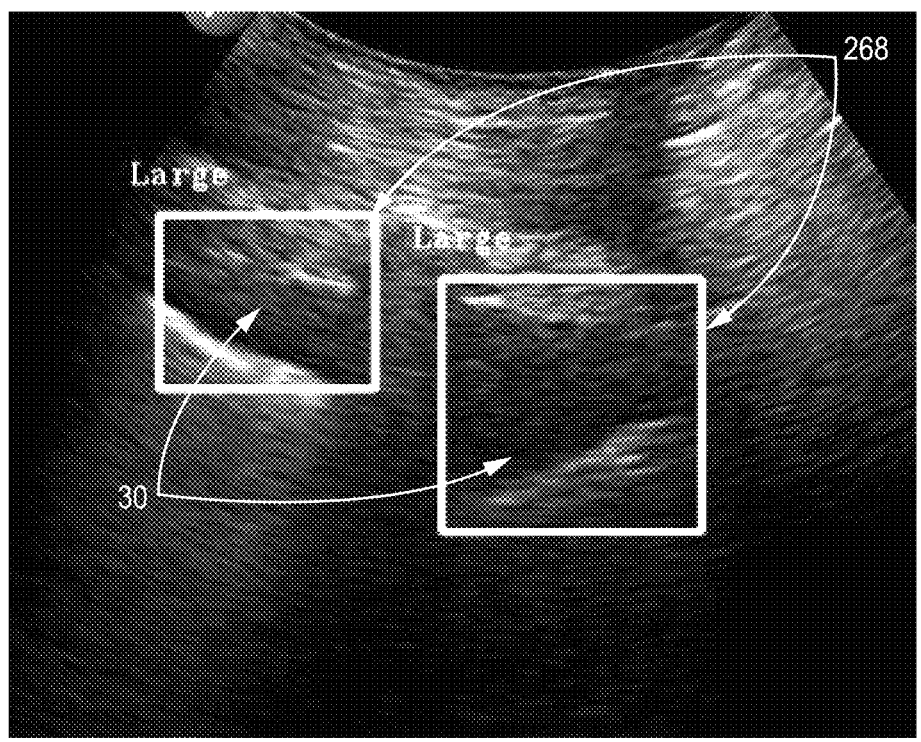
Figure 6:
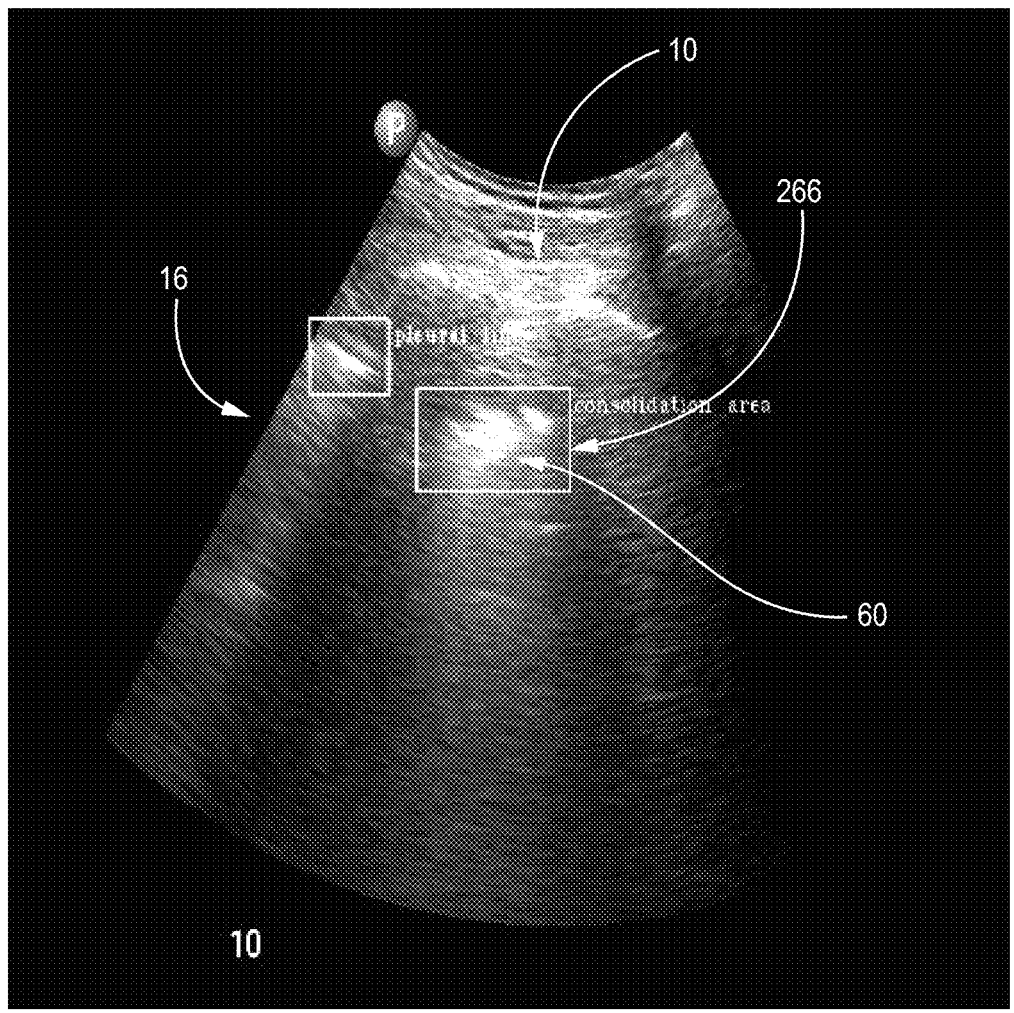
FIG. 6 is an ultrasound image of a lung, the image including features corresponding to a consolidation.
Figure 7:
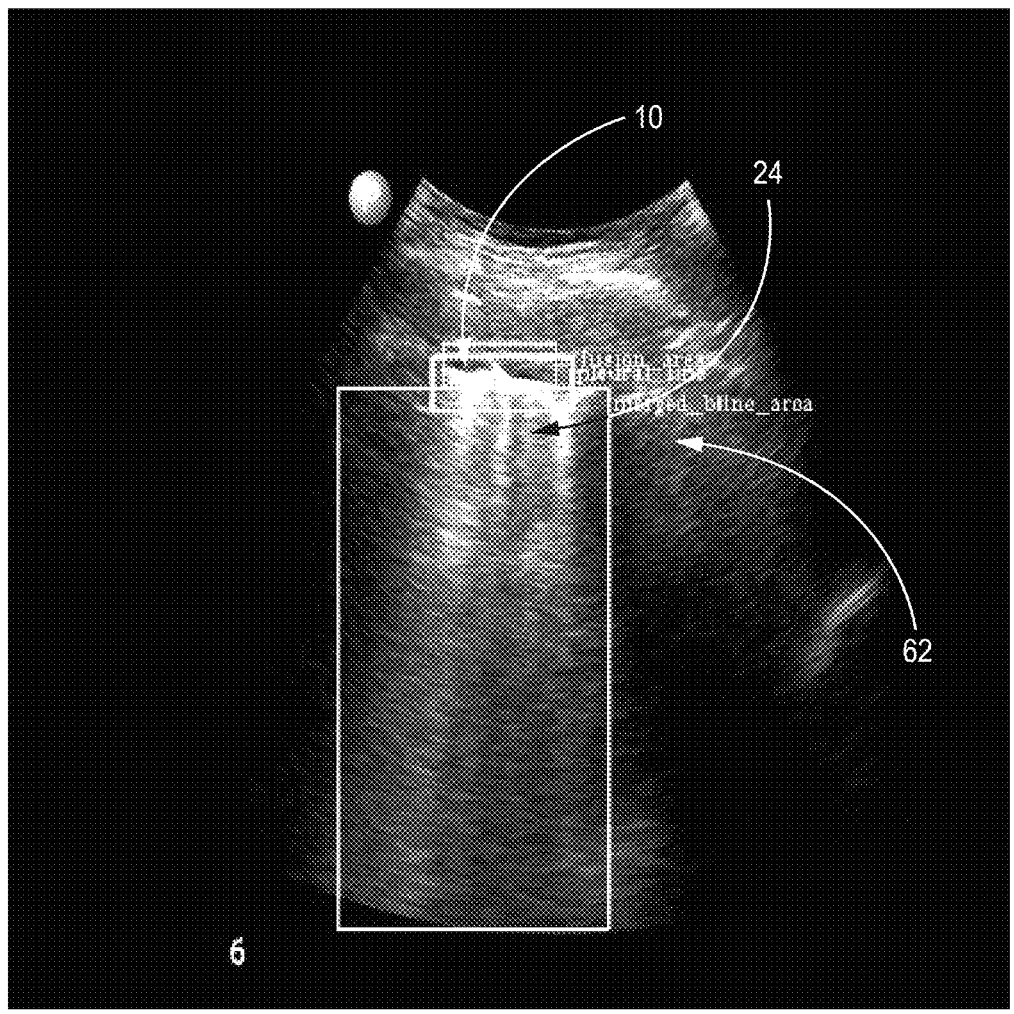
FIG. 7 is an ultrasound image of a lung, the image including features corresponding to a merger of B-lines.

The outputs 232, 233, 234 and 235 of the modules 222, 223, 224, and 225 have the same format; that is, each of these outputs represents one or more detections of a feature, each detection being represented by five real numbers. For example, the first number of a detection of the output 232 is the probability, or confidence level, that the image feature detected is a B-line. The remaining four numbers are, respectively, the <x,y> coordinates of the upper-left corner of the bounding box containing the detected B-line, and the width <$\Delta$x, $\Delta$y> of the bounding box (see, e.g., bounding box 262 of FIG. 2). Similarly, the first number of a detection of the output 233 is the probability, or confidence level, that the image feature detected is a pleural line. The remaining four numbers are, respectively, the <x,y> coordinates of the upper-left corner of the bounding box containing the detected pleural line, and the width <$\Delta$x, $\Delta$y> of the bounding box (see, e.g., bounding box 264 of FIG. 2). Likewise, the first number of a detection of the output 234 is the probability, or confidence level, that the image feature detected is a consolidation. The remaining four numbers are, respectively, the <x, y> coordinates of the upper-left corner of the bounding box containing the detected consolidation, and the width <Δx, Δy> of the bounding box (see, e.g., bounding box 266 of FIG. 6). Similarly, the first number of a detection of the output 235 is the probability that the image feature detected is a pleural effusion. The remaining four numbers are, respectively, the <x, y> coordinates of the upper-left corner of the bounding box containing the detected pleural effusion, and the width <Δx, Δy> of the bounding box (see, e.g., bounding boxes 268 of FIGS. 3, 4, and 5).

Figure 13:
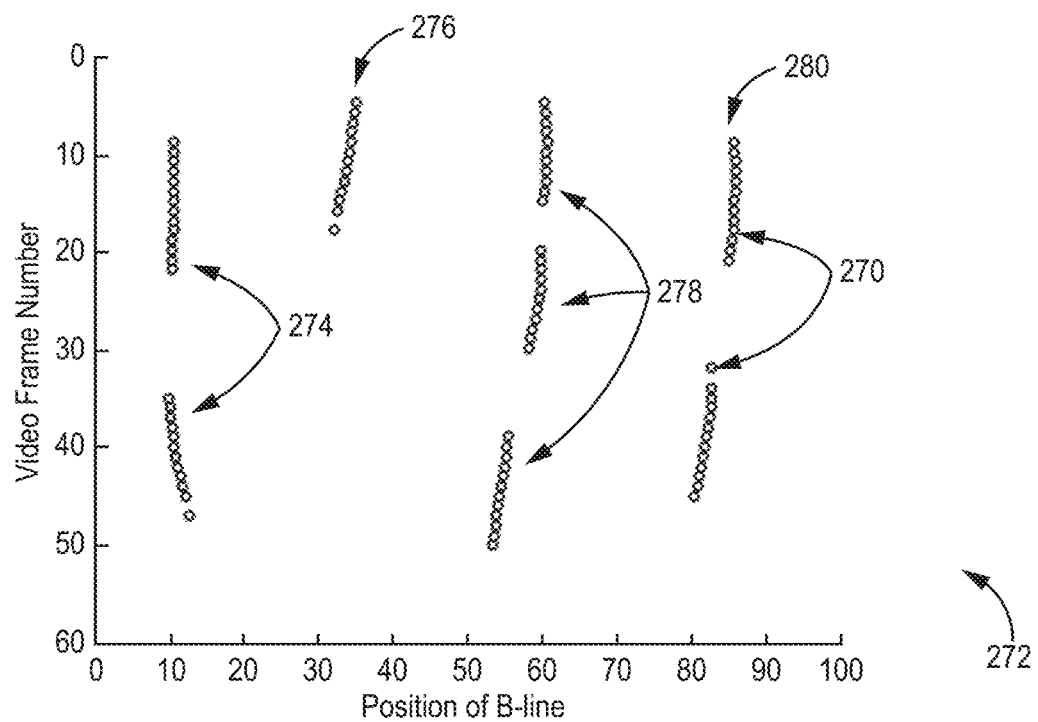
FIG. 13 is a plot of B-lines and B-line clusters in an ultrasound image of a lung, according to an embodiment.
Figure 14:
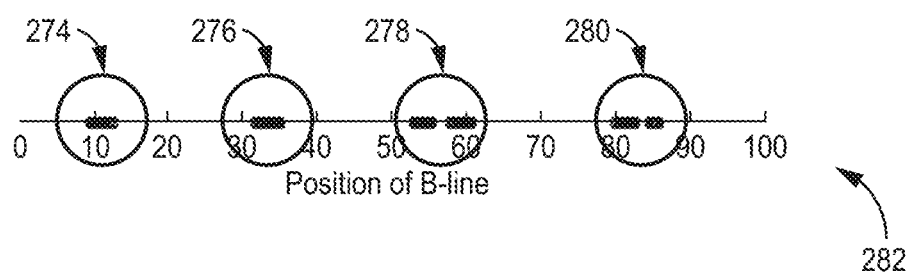
FIG. 14 is the plot of FIG. 13 compressed into one dimension along the horizontal axis of the plot, according to an embodiment.

At a step 242, the ultrasound machine 125 (FIG. 8) further analyzes the identified/classified B-lines to determine the true number of B-lines, because the probability that a lung problem exists, and the severity of the lung problem, is related to the number of actual B-lines; this analysis is called B-line clustering. Generally, a single B-line can appear to move relative positions from image to image due to movement of the lung during breathing. Therefore, counting B-lines from image to image may result in a larger number of B-lines than actually exist because a B-line in one image may be the same B-line in another image even though the position of the B-line is different from image to image. Therefore, referring to FIG. 13, the ultrasound system 130 (FIG. 8) effectively plots the locations of the B-lines 270 from frame to frame, and calls the formed groups of B-lines B-line clusters. The plot 272 of FIG. 13 shows four clusters 274, 276, 278, and 280 of B-lines 270, each cluster indicated by a respective circle in the plot 282 of FIG. 14, where the plot 282 is the plot 272 of FIG. 13 compressed into one dimension along the horizontal axis. Consequently, the ultrasound system 130 (FIG. 8) determines that the actual number of B-lines 270 is the number of clusters, here four clusters 274, 276, 278, and 280, uses this number (here four) as an indicator of the number of B-lines, and uses the positions of the clusters (e.g., uses a respective centroid of each cluster as the position of each cluster) as the positions of the B-lines, when determining the probability and severity of a lung problem indicated by the B-lines.

Figure 17:
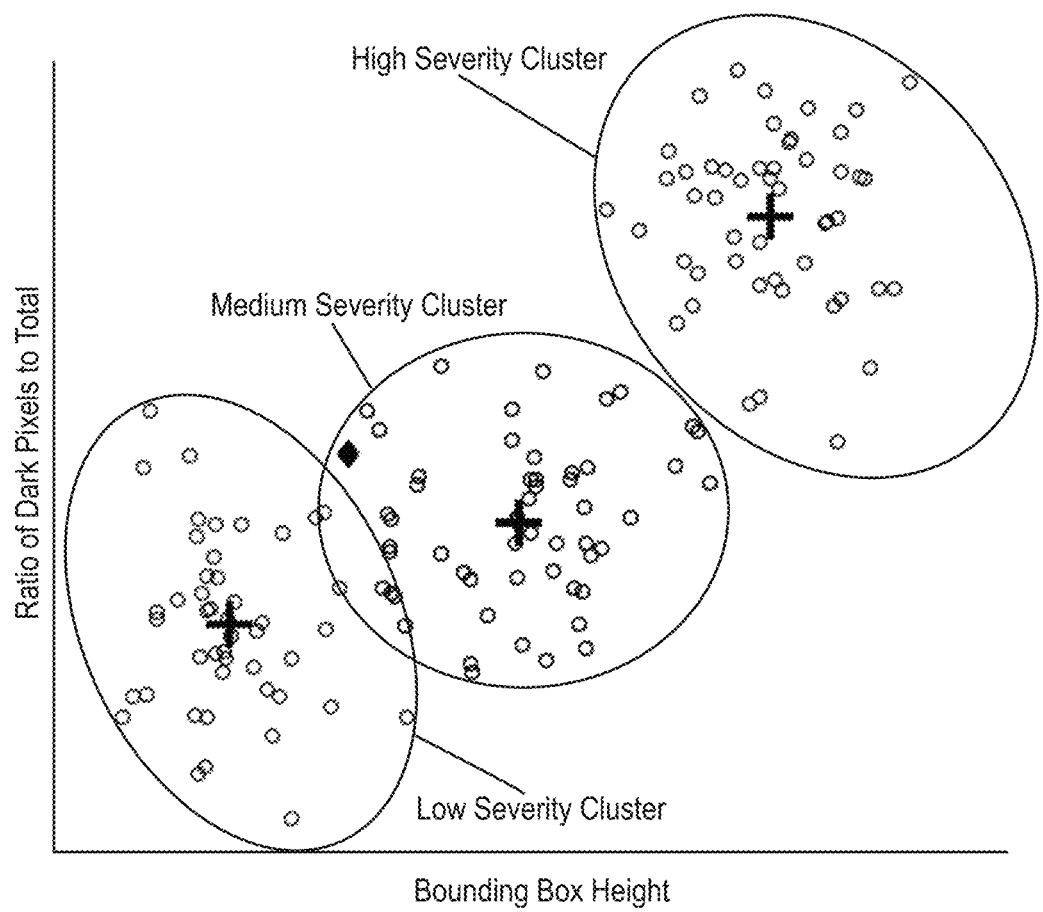
FIG. 17 is a plot of instances of pleural effusion by size (bounding-box height) along the abscissa and by the ratio of the number of dark pixels to the number of total pixels along the ordinate, according to an embodiment.

Referring to FIGS. 9 and 17, at a step 245, further analysis of any detected and classified pleural effusions yields a respective grade (e.g., low severity, medium severity, high severity) for each identified pleural effusion.

Referring again to FIG. 9, as outputs 250, 251, 252, 253, 254, and 255, the ultrasound system 130 (FIG. 8) yields the existence or number, and severity, of the respective identified feature.

For example, as the output 250, the ultrasound system 130 (FIG. 8) yields the probability, or confidence level, that lung sliding exists, and, the likely severity of any existing lung sliding.

Similarly, as the output 251, the ultrasound system 130 yields the number and locations of any A-lines detected, the probability, or confidence level, that a pathology corresponding to the detected one or more A-lines (e.g., corresponding to the one or more A-lines alone or to the one or more A-lines in combination with one or more other detected features) exists, and the likely severity of the corresponding pathology if the pathology exists.

As the output 252, the ultrasound system 130 yields the number and locations of any B-lines detected, the probability, or confidence level, that a pathology corresponding to the detected one or more B-lines (e.g., corresponding to the one or more B-lines alone or to the one or more B-lines in combination with one or more other detected features) exists, and the likely severity of the corresponding pathology if the pathology exists.

As the output 253, the ultrasound system 130 yields the locations of any pleural lines detected, the probability, or confidence level, that a pathology corresponding to the detected one or more pleural lines (e.g., corresponding to the one or more pleural lines alone or to the one or more pleural lines in combination with one or more other detected features) exists, and the likely severity of the corresponding pathology if the pathology exists.

As the output 254, the ultrasound system 130 yields the locations of any consolidations detected, the probability, or the confidence level, that a pathology corresponding to the detected one or more consolidations (e.g., corresponding to the one or more consolidations alone or to the one or more consolidations in combination with one or more other detected feature) exists, and the likely severity of corresponding pathology if the pathology exists.

And as the output 255, the ultrasound system 130 yields the locations of any pleural effusions detected, the probability, or confidence level, that a pathology corresponding to the detected one or more pleural effusions (e.g., alone or in combination with another detected feature) exists, and the likely severity of corresponding pathology if the pathology exists.

At a step 170, the ultrasound system 130 (FIG. 8) executes an algorithm (e.g., a CNN or a rule-based algorithm) to analyze the detected and categorized features and severities yielded as the outputs 250-255 for the purpose of rendering a diagnosis. At a step 180, the ultrasound system 130 (FIG. 8) yields a likely diagnosis (e.g., likely pneumonia, likely pneumothorax), based on the features, classifications, and severities yielded as the outputs 250-255.

Still referring to FIG. 9, in an alternate embodiment of the workflow 200, the preprocessing module 201 optionally enhances the image video frames 211 for the purpose of improving accuracy of detection and classification for one or more lung features and pathologies. For example, the B-line 601 shown in FIG. 10 is robust and, and, therefore, is typically easily detected by the ultrasound system 130 (FIG. 8) at the B-line-detector step 222. There are, however, weaker B-lines (not pointed out in FIGS. 9-10) that may evade detection. The B-line accuracy of the ultrasound system 130 may be improved through the introduction of pseudo-color image channels based on image-filtering operations applied to the original grayscale image. An image frame extracted from an ultrasound video may be filtered to enhance certain feature types. For example, a B-line may be enhanced when it is filtered with a Gabor filter having the same orientation and the same scale as the B-line. One or more of these filtered images may be stacked along with the original grayscale image as pseudo-color channels, and these filtered images may be used for training and testing the CNN models of the ultrasound system 130.

Figure 11:
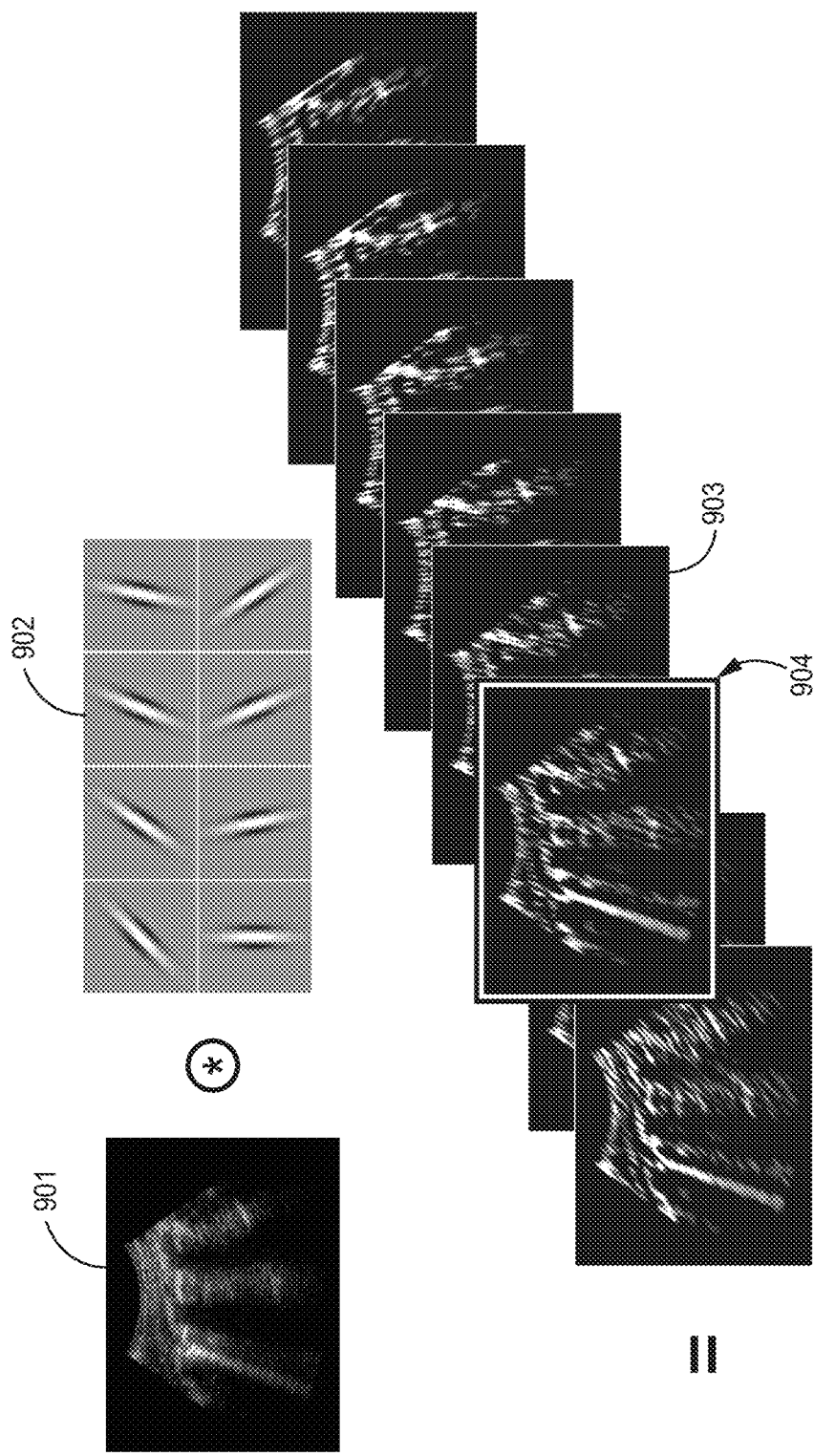
FIG. 11 is a diagram of a method for enhancing an ultrasound image of a lung by filtering the image, according to an embodiment.

An illustration of an embodiment of this video-image-enhancement technique for B-lines is shown, and described in conjunction with, FIG. 11. Original grayscale image 901, which is the image of FIG. 10 and, therefore, which includes the B-line 601 of FIG. 10, is filtered with a filter bank including eight oriented, elongated Gabor filters 902, although in other embodiments, the filter bank can include more or fewer than eight Gabor filters. The Gabor filtering operation results in the bank of images 903. The image in the bank 903 corresponding to the Gabor filter mostly closely aligned with the B-line 601 in the image 901 typically stands out. In this example, the third Gabor filter most closely aligns with the B-line 601, and, therefore, corresponds to the third image 904 in the bank 903. After undergoing this filtering operation, the original grayscale image 901 is appended with the bank 903 of the eight filtered images to form a nine-channel image, which, in an embodiment, forms an input to the CNN models implemented by the ultrasound system 130 (FIG. 8). This filtering algorithm can take advantage of multiple image channels that the ultrasound system 130 implements, at least some of such channels being for the different components of a color image; examples of such components include Red (R), Green (G), Blue (B), Y, CB, and CR.

Still referring to FIG. 11, in more detail, the ultrasound system 130 (FIG. 8) implements an image-processing technique to enhance B-lines so that they are easier for a CNN implemented by the ultrasound imaging system to detect and to classify. For a curvilinear ultrasound transducer 120 (FIG. 8), B-lines extend radially from the transducer (image 901, see also the same image in FIG. 10). Therefore, the image can be processed according to Gabor filters having axes that respectively lie along lines extending radially from the center of the transducer 120. For example, a filter sharpens (e.g., brightens, increases contrast of) brighter pixels that are aligned with, and that are inside of, the filter boundary. The ultrasound system 130 effectively steps each filter horizontally and vertically (e.g., 1 pixel at a time in each dimension) over the image so as to filter B-lines regardless of where they are located within an image. And although the image 902 shows only eight filters, other numbers of filters can be used. After the filtering, the ultrasound system 130 stacks the original grayscale image together with N filtered images to form an N+1 channel pseudo-color image. That is, each of these images, original and filtered, is input to the B-line-feature-detection SSD CNN (step 222 of FIGS. 9 and 16) on a separate input channel. So, the SSD CNN effectively analyzes all of these images, both original and filtered, to detect and to classify B-lines.

Furthermore, although FIG. 11 shows only B-line filters, the ultrasound system 130 (FIG. 8) can employ filters to enhance A-line, and the other searched-for features. Moreover, multiple enhanced features can appear on a single output image; that is, each feature filter is not required to generate a respective separate set of images. For example, all searched-for features of an image can be enhanced, and the result of all of the enhancements can be combined into a single stack of images that correspond to a single input image, where each image in the stack (filtered and original) is input to a respective channel of the SSD CNN. An SSD CNN is typically configured to receive at least three input pixel streams corresponding to a color image (e.g., RGB, HSV). However, per FIG. 11, an SSD CNN can be configured to receive an input image with a number of channels significantly greater than three, depending on the number of filtered/enhanced images that are generated for each original ultrasound image.

In other embodiments, the ultrasound system 130 can perform other pseudo-color enhancements to improve accuracy for other features (e.g., A-line, pleural line, consolidation, and pleural effusion) of interest.

Still referring to FIG. 9, in yet another embodiment of the workflow 200, each of one or more of the detection outputs 231, 232, 233, 234, and 235 undergoes further processing before the output is reported to a user as detected feature. For example, as stated above, B-lines are image artifacts that are caused by reverberations of acoustic waves at a fluid-air interface inside of a lung. As stated above, an example of an ultrasound video frame exhibiting a B-line 601 is shown in FIG. 10. In FIG. 10, the B-line 601 has a position 602 along an arc 603 as indicated because the ultrasound transducer 120 (FIG. 8) that was used to make the image of FIG. 10 is a curvilinear transducer such that the B-line 601 extends radially outward from the transducer. As stated above, multiple or merged B-lines in an ultrasound image may be a symptom of a serious abnormal lung condition such as pneumonia or acute respiratory distress syndrome (ARDS). The number of B-lines in an ultrasound image can be important as it can be an indication of the severity of the condition, with greater than three B-lines, for example, being clinically and statistically relevant. During the capture of a stream of ultrasound video images (e.g., the ultrasound video images 140) of a lung, as the patient respires, B-lines may change position from image frame to image frame due to the movement of the pleural membranes of the lung. The B-lines may also fade in and out in the sequence of video-image frames. In an embodiment, the ultrasound system 130 (FIG. 8) detects B-lines 270 frame by frame. Furthermore, the ultrasound system 130 employs a clustering technique in which the ultrasound system associates detected B-lines across multiple frames of a video stream to determine the true number of B-lines present in the analyzed video images. This post-processing clustering of B-lines 270 is indicated as a step 242 in FIG. 9. As described above, FIG. 13 is a plot of the detected individual B-lines 270 at various locations across multiple video frames. Each B-line detection 270 is indicated with a small circle, the location of the B-line within a corresponding image frame is plotted along the abscissa of the plot 272, and the identifier (e.g., the number) of the image frame in which the B-line is detected is plotted along the ordinate of the plot 272. As described above, FIG. 14 shows the B-line detections across all analyzed ultrasound video frames projected onto the abscissa (e.g., the x-axis). The clustering algorithm that the ultrasound system 130 implements during the step 242 determines, in the described example, that the collection of all detected B-lines 270 across all analyzed frames of the ultrasound video are grouped into four clusters 274, 276, 278 and 280 by location, as indicated by the circles in FIG. 14. More specifically, the clustering algorithm is not part of any of the SSD CNNs that the ultrasound system 130 may execute during the steps 221, 222, 223, 224, and 225 of FIG. 9, but is another type of algorithm that is, or uses, for example, a conventional distance-based clustering technique or a conventional density-based clustering technique to determine the number of clusters and to which cluster each B-line 270 belongs. For example, in FIG. 14, the clustering algorithm determines that all B-lines within a threshold distance, e.g., ten units, from one another are considered to be part of the same cluster, where a "unit" can be any arbitrary unit of distance such as pixels or millimeters (mm). Consequently, the clustering algorithm determines a level of severity of detected B-lines 270 in the analyzed portion of the ultrasound video in response to the number of B-line clusters (here, four clusters 274, 276, 278, and 280) that the clustering algorithm identifies, not in response to the raw count of the B-lines 270 that the clustering algorithm detects in all analyzed frames of the ultrasound video.

Figure 16:
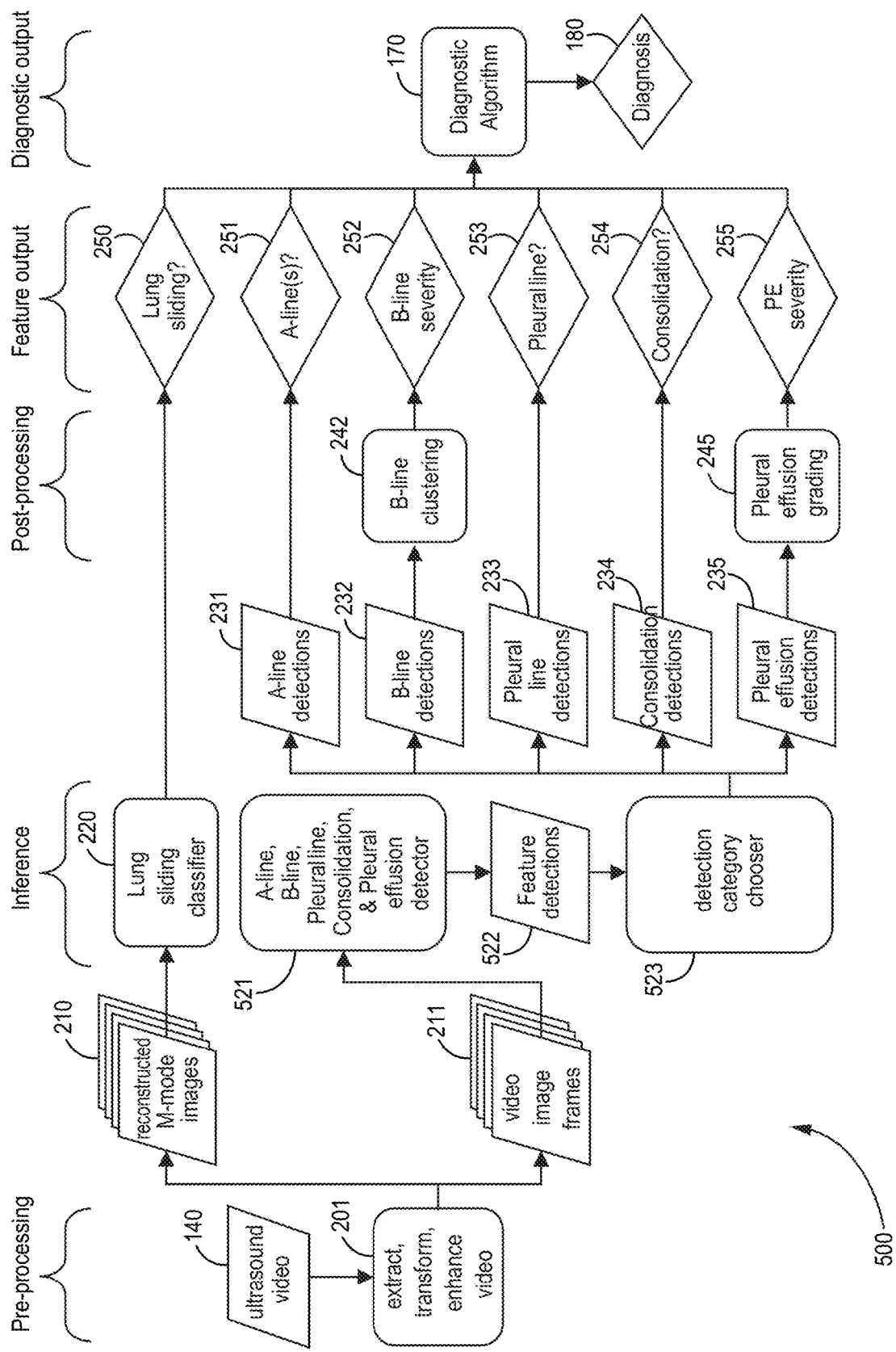
FIG. 16 is a diagram of a workflow for multi-class feature/object detection and identification/classification, according to an embodiment.

FIG. 16 is a diagram of a workflow 500, which is similar to the workflow 200 of FIG. 9, but which is a workflow for multi-class object detection and classification, according to an embodiment. Instead of running a separate SSD CNN to detect and to classify each feature (e.g., A-line, B-line, pleural line, consolidation, pleural effusion), the ultrasound system 130 (FIG. 8) runs a single, multi-class SSD CNN to detect and to classify each feature (the ultrasound system still classifies lung sliding with a separate classification CNN as described above in conjunction with FIG. 9).

Steps, outputs, and objects 140, 201, 210, 211, and 220 are similar to these same steps, outputs, and objects as described above in conjunction with FIG. 9.

At a step 521, the ultrasound system 130 (FIG. 8) implements a single, multi-class SSD CNN as described above, to detect, in the ultrasound video-image frames 211, one or more features such as A-line, B-line, pleural line, consolidation, and pleural effusion.

Next, at a step 523, the ultrasound system 130 (FIG. 8) classifies each instance of a detected feature 522 as a specific one of the features such as A-line, B-line, pleural line, consolidation, and pleural effusion. That is, each of the detections 522 1 includes a respective location within a respective one of the image frames 211 where the ultrasound system 130 has detected something (e.g., a feature), and includes the probabilities, or confidence levels, that detected something is one of the features (e.g., A-line, B-line, pleural line, consolidation, pleural effusion) that the ultrasound system 130 is "looking for."

Then, at a step 523, in response to the respective location and respective probabilities or confidence levels, the ultrasound system 130 (FIG. 8) classifies each feature detection 522 as either one of the features (e.g., A-line, B-line, pleural line, consolidation, pleural effusion) that the ultrasound system 130 is "looking for," or as an unknown feature (in most cases, however, at the step 521 the ultrasound system 130 does not detect a feature unless the feature is one of the features that the ultrasound system 130 is "looking for."

Still referring to FIG. 16, classified feature detections 231, 232, 233, 234, and 234, steps 242 and 245, outputs 250, 251, 252, 253, 254, and 255, step 170, and diagnosis 180 are similar to the corresponding detections, steps, and outputs as described above in conjunction with FIG. 9. That is, after the step 523, operation of the ultrasound system 130 (FIG. 8) as it performs the workflow 500 is similar to the operation of the ultrasound system as it performs the workflow 200 of FIG. 9 after the steps 220, 221, 222, 223, 224, and 225.

Referring to FIGS. 9, 16, and 17, the step 245 of grading pleural effusions is described, according to an embodiment.

FIG. 17 is a plot of instances of pleural effusion plotted as a function of size (e.g., bounding-box height, bounding boxes are described below in conjunction with FIGS. 22-23) along the abscissa and ratio of the number of dark pixels to the number of total pixels along the ordinate, according to an embodiment. One can see that the larger the size (e.g., bounding-box height) and the higher the ratio of the number of dark pixels to the number of total pixels, the more severe the instance of the pleural effusion, at least as determined by the ultrasound system 130 (FIG. 8). The pleural effusions in the low-severity cluster (hereinafter "group"), medium-severity group, and high-severity group are from training images, and the crosses indicate the two-dimensional centers of mass of the points (represented by circles in FIG. 17) within each group, respectively. The boundaries between the groups are determined by a conventional unsupervised clustering algorithm (an unsupervised clustering algorithm finds similarities in the input data without being "told" the identity of the samples).

After training, at the step 245 of FIGS. 9 and 16, the ultrasound system 130 (FIG. 8) effectively plots a detected and identified pleural effusion (represented by the diamond in FIG. 17), determines the respective distance between the plotted pleural effusion and each of the group centers (crosses in FIG. 17), and identifies the pleural effusion as having a grade corresponding to the group to which the pleural effusion is closest. For example, if the pleural-effusion (diamond) is closest to the center (cross) of the medium-severity group, then the ultrasound system 130 grades the pleural effusion as being of medium severity.

Still referring to FIGS. 9, 16, and 17, the step 245 of grading pleural-effusions is described in more detail.

The plot of FIG. 17 is a scatter plot of training examples in the space consisting of two attributes: bounding box height (size) vs. ratio of dark pixels to total pixels. The ultrasound machine 130 (FIG. 8) may perform clustering using any of the following conventional algorithms: k-means, Gaussian mixture model (GMM), and density-based clustering. The number of groups, or clusters, is determined a priori, is an input to the clustering algorithm (e.g., by a programmer or one who configures the clustering algorithm for a particular application) and is chosen to be equal to the number of severity categories desired. For example, if the desired categories are low severity, medium severity, and high severity, the number of clusters, k, is set to 3. FIG. 17 shows the results of clustering the training examples using k-means. The cluster centers are indicated with the cross, or "plus," symbols. Once the training-set examples are clustered into, say, k=3 groups, the mapping between cluster index and its corresponding severity is determined by examining the severity of the training cases in each cluster. The majority of examples falling in each cluster will determine the identity of that cluster. In the example shown in FIG. 17, the lower-left cluster corresponds to low severity, the middle cluster corresponds to medium severity, and the upper-right cluster corresponds to high severity.

During an inference portion of the step 245 of FIGS. 9 and 16, any detected pleural effusion has its clustering attributes extracted and evaluated by the grading algorithm. If the clustering algorithm is k-means, for example, the pleural-effusion detection is categorized as low severity if its attribute values are closest to the cluster center (cross) corresponding to low-severity effusions, and so on. If the clustering algorithm is GMM, then the ultrasound system 130 (FIG. 8) assigns the detected pleural effusion to the cluster that has the highest posterior probability based on the clustering attributes of the detected pleural effusion. In FIG. 17, the gray diamond represents the clustering attributes of a detected and classified pleural effusion. Its position in the clustering-attributes space is closest to the medium-severity cluster's center (cross), so the ultrasound system 130 grades the corresponding pleural effusion as a medium-severity pleural effusion.

Referring to FIG. 16, in an embodiment, the multi-class SSD CNN that the ultrasound system 130 (FIG. 8) implements to perform steps 521 and 523 outputs, for each detected feature, a vector of nine real numbers. The first five numbers are the respective probabilities/confidences that the detected feature belongs to one of the target classes/categories, e.g., (A-line, B-line, pleural line, consolidation, pleural effusion). Typically, the feature is classified according to the class indicated by the highest confidence number.

A "tie" between two confidence levels for different categories is unlikely to occur because the ultrasound system 130 (FIG. 8) post-processes the confidence levels output from the multiclass SSD CNN by implementing a conventional softmax operation, which tends to amplify the highest confidence level and to suppress the other confidence levels (sort of like a differential-error amplifier). In the unlikely event that two confidence levels are exactly equal, the ultrasound system 130 can implement a tie-breaking algorithm, or can report the multiple tied classifications for the detected feature.

Figure 18:
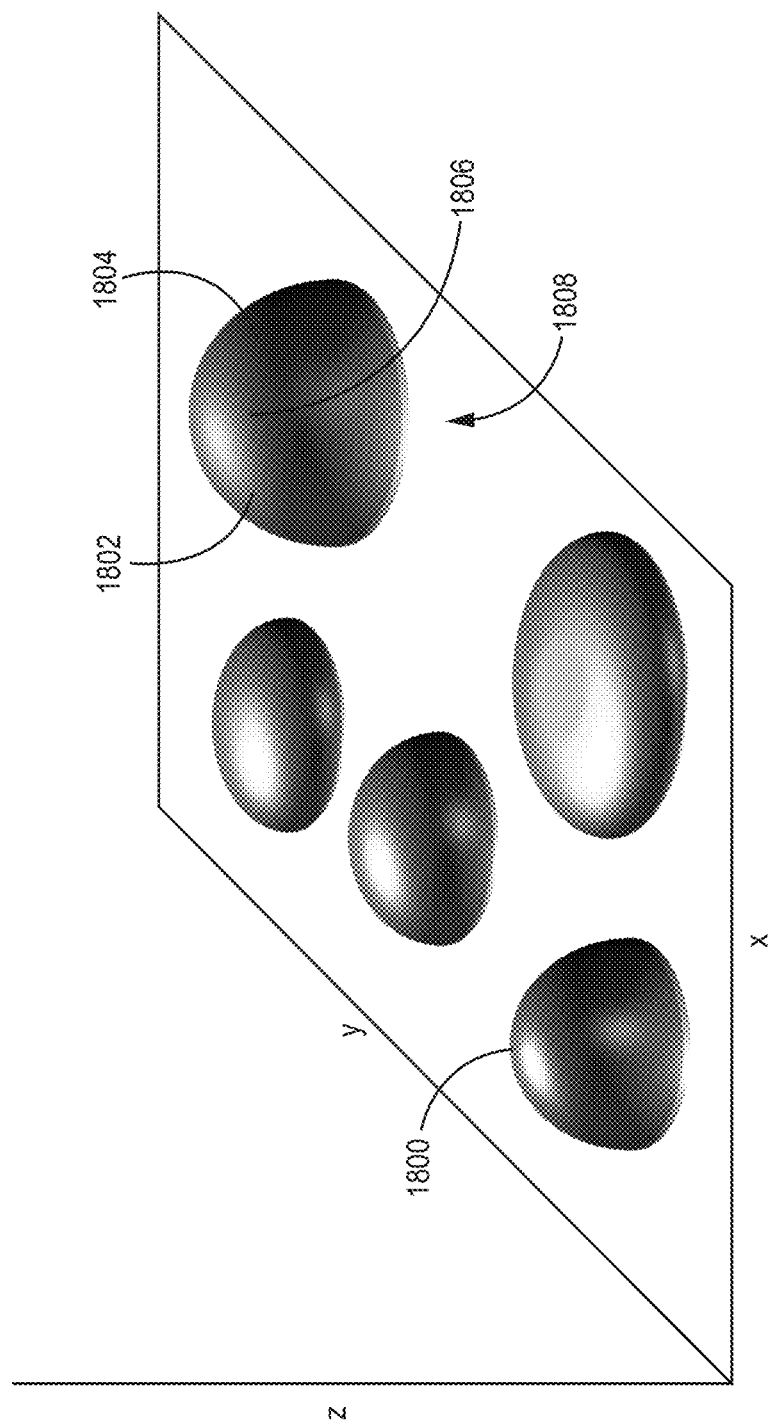
FIG. 18 is a plot generated by performing a non-maximum-suppression algorithm, according to an embodiment.

Referring to FIG. 18, to determine, from the potential locations, the actual location of each detected feature, the ultrasound system 130 (FIG. 8) implements an embodiment of a non-maximum suppression operation. While executing the non-maximum suppression algorithm, the ultrasound system 130 (FIG. 8) effectively plots the highest score (e.g., confidence levels) values for each detected and classified feature on a 3D map, where the <x, y> plane is the image plane (i.e., the plane of the ultrasound image), and the score values are plotted along the z dimension. The ultrasound machine 130 "looks for" peaks in the score map and selects the peaks as the location of the features. For example, a score map forms a peak at location 1800, and, therefore, the non-maximum suppression operation accepts the feature (e.g., A-line, B-line, pleural line, consolidation, pleural effusion) classified by the score value at the location 1800. But multiple score values at locations 1802, 1804, and 1806 form a cluster 1808 of scores. Because the score value at location 1806 is the highest (at the peak of the "hill"), the ultrasound machine 130, while performing the non-maximum suppression operation, selects the score value at the location 1806 as corresponding to a true detected and classified feature, and effectively discards the score values at 1802 and 1804 as corresponding to redundant, or "ghost," features; that is, the ultrasound system 130, while executing the non-maximum suppression algorithm, prunes the cluster 1808 of features to determine the classification and position (in the image) of one true feature, which is the feature with the highest score value.

The remaining four numbers of the vector are, respectively, the offset from the default bounding box x, y coordinates of the upper left corner of the actual bounding box of the feature, and the offset from the default bounding box width ($\Delta x$) and height ($\Delta y$) of the actual bounding box. Such bounding boxes are shown in at least some of FIGS. 1-7. In an embodiment, the size and/or relative location of the actual bounding box may be respective indicators of the severity of the pathology indicated by the classified feature, and the ultrasound system 130 (FIG. 8) is configured to process the pixels within the actual bounding box according to any suitable algorithm to give yet another indication of severity. Furthermore, the ultrasound system 130 makes the severity determination by implementing the CNN or by implementing an algorithm separate from the CNN. A good high-level overview of a CNN for image processing is on the world wide web at https://blog.athelas.com/a-brief-history-of-cnns-in-image-segmentation-from-r-cnn-to-mask-r-cnn-34ea83205de4, by Dhruv Parthasarathy.

Referring to FIGS. 8 and 10-17, although described as implementing one or more SSD CNNs, the ultrasound system 130 can be configured to implement other types of algorithms to perform the above-described functions, such other types of algorithms including You Only Look Once (YOLO), Region-Based CNN (R-CNN), Fast R-CNN, and Faster R-CNN. Furthermore, the ultrasound system 130 can be configured to implement a single neural network, or multiple neural networks, to perform the above-described functions, and can use algorithms other than neural networks to perform one or more of the above-described functions. And, as stated previously, a non-SSD CNN is typically used to classify lung sliding since detection of lung sliding is not needed (the ultrasound system 130 performs only classification (is it "there" or "not there") for lung sliding). There can be advantages and disadvantages for the single-class and the multi-class embodiments of FIGS. 9 and 16, respectively. A set of single-class detectors may use more computer-processing time and power because multiple individual CNN models are evaluated for each input image. A multi-class detector may be more computationally efficient, but detections of different feature classifications that are co-located in an image may compete with one another, thereby reducing sensitivity to one or more feature classifications. Therefore, a designer of the ultrasound system 130 can carefully consider these tradeoffs when selecting which embodiment to deploy in a clinical setting.

Training of One or More CNNs Implemented by the Ultrasound System

Figure 19A:
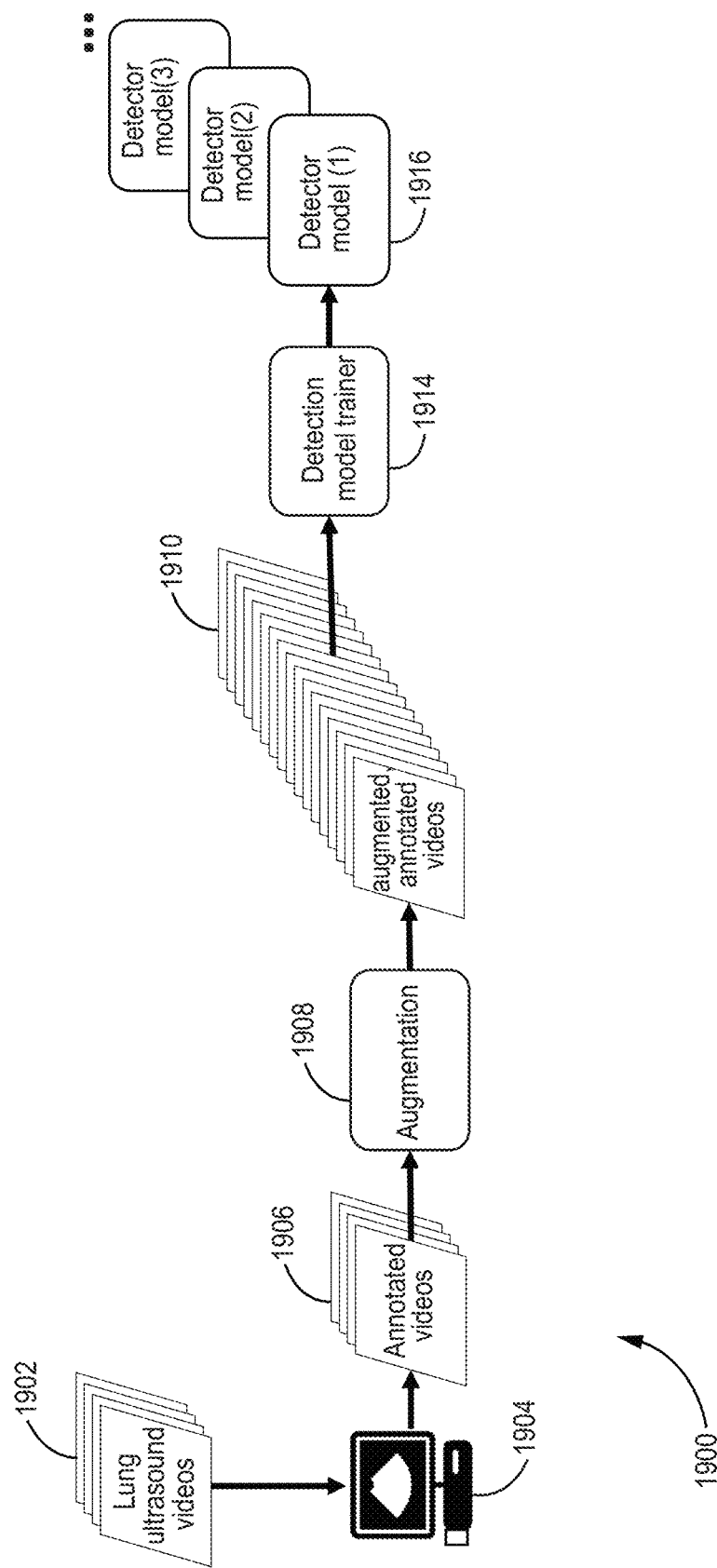
FIG. 19A is a workflow for training one or more detector-model-based neural networks, according to an embodiment.
Figure 19B:
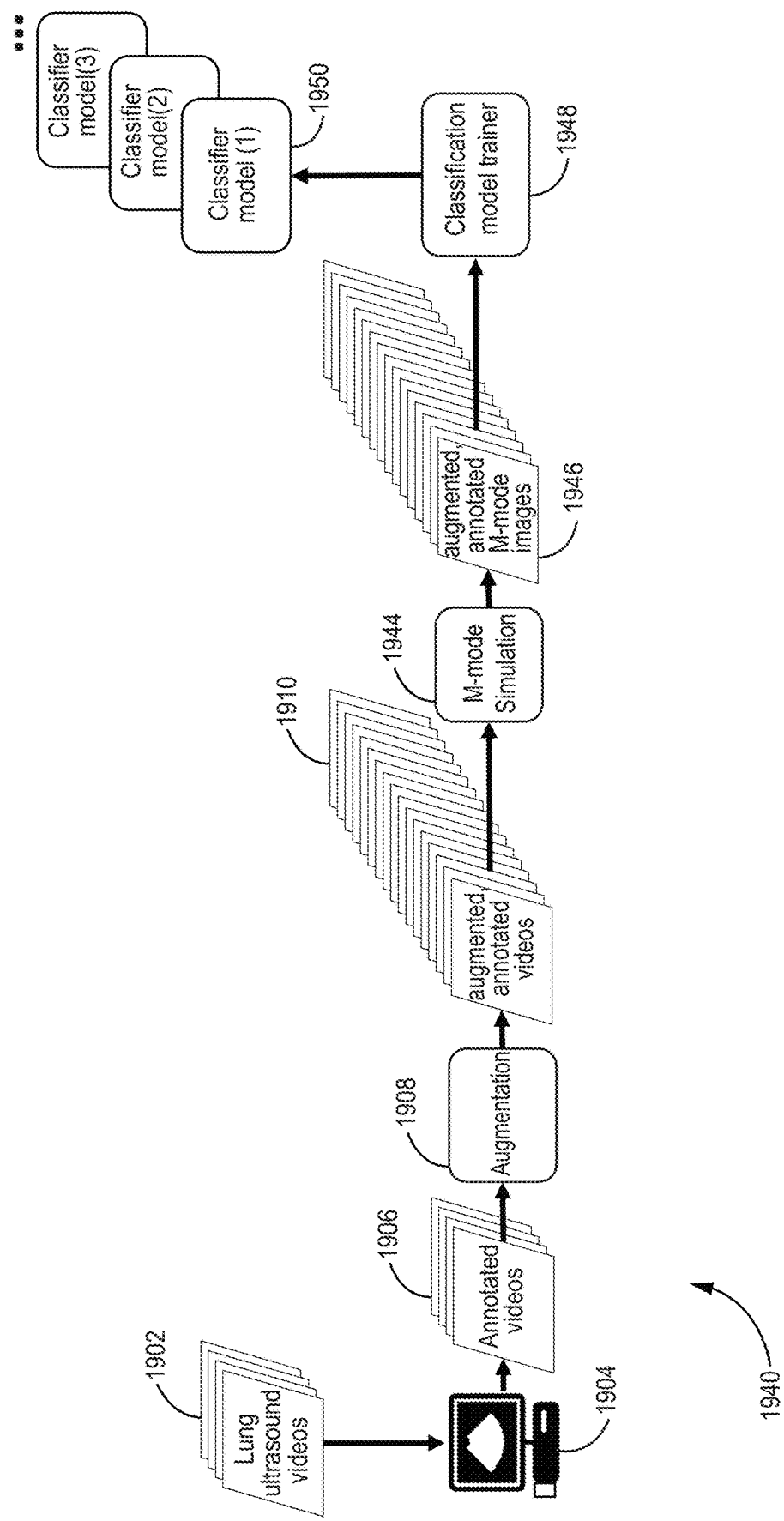
FIG. 19B is a workflow for training one or more classifier-model-based neural networks, according to an embodiment.

Referring to FIGS. 19A and 19B, according to an embodiment, in a supervised learning paradigm, a neural network, such as a CNN, is trained on images or videos with features known a priori before the ultrasound system 130 (FIG. 8) uses the neural network to detect and identify features in images or videos where the features are not known a priori.

Deep learning models are usually trained with a gradient descent algorithm. Algorithms in this family are iterative and gradually descend to a low value of the cost (loss) function after a great many iterations. Depending on the size of the model and the number of training samples, the training process can last hours, days, or even weeks. Most software frameworks for training Deep Learning models allow the user to monitor the overall loss function and to save the intermediate solutions (models) as the training proceeds. Thus, the training process generates a large number of intermediate models and the best model among these is selected for implementation in the deployed system. In FIG. 19A, block 1914 represents software, for execution by hardware, for training one or more detector-neural-network models. The training process generates multiple detector machine-learning models 1916, one of which is selected, after the training is complete, to be the detector neural network, such as an SSD CNN. And in FIG. 19B, a block 1948 represents software, for execution by hardware, for training one or more classifier neural network models such as a CNN. The training process generates multiple classifier machine-learning models 1950, one of which is selected, after the training is complete to be the classifier neural network.

Figure 20:
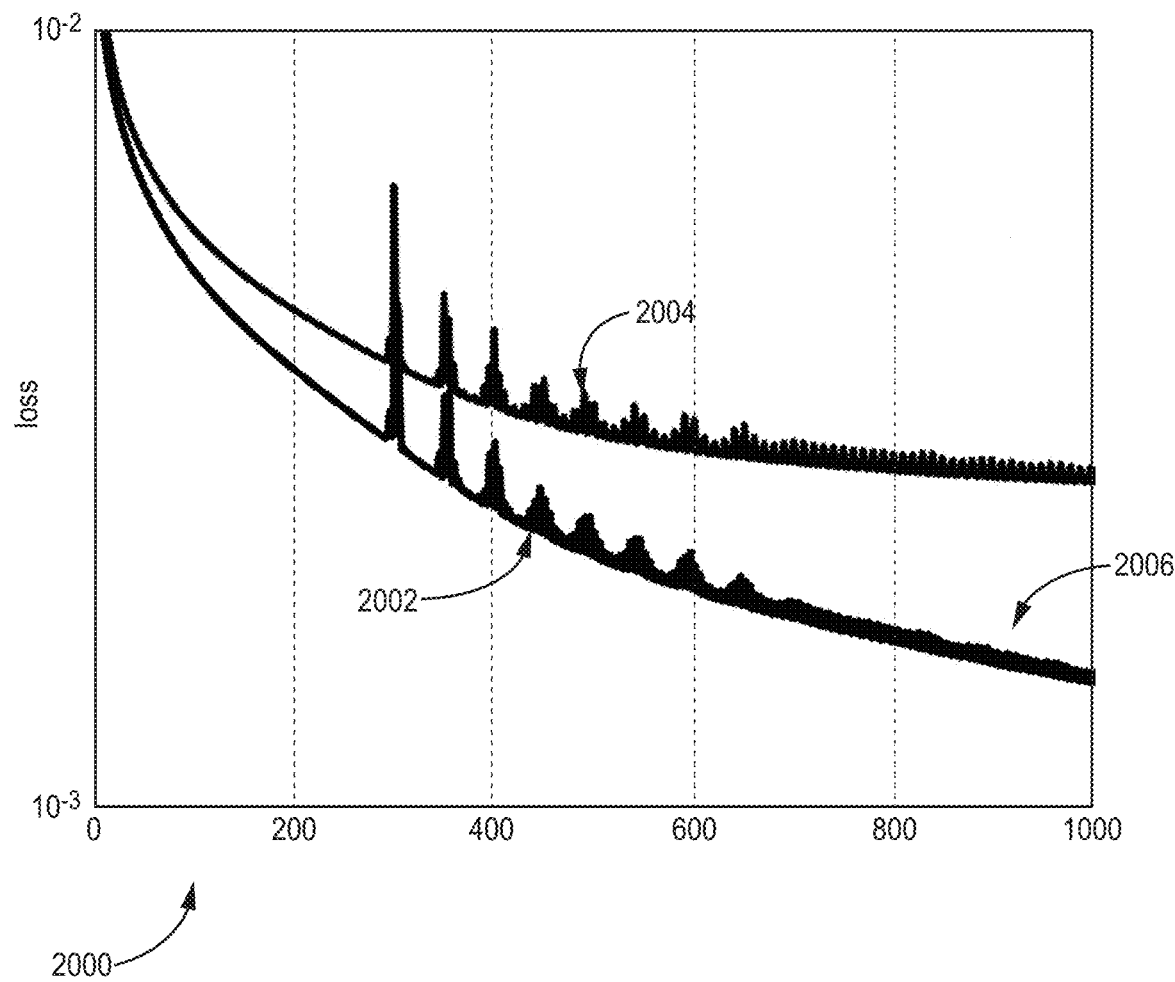
FIG. 20 is a plot of training loss and validation loss (ordinate) versus the number of different final training images (abscissa) used to train an SSD CNN, according to an embodiment.

In addition to the training set of images, most practitioners of Deep Learning also set aside a validation set of images to monitor the loss on the validation set. Referring to FIG. 20, typically, the loss (e.g., training loss) on the training set of images continues to decrease, but the loss (e.g., validation loss) on the validation set of images either plateaus or begins to rise at a certain point in the training process. The performance of the neural networks on the validation set can be crucial for selecting a stopping point for training as well as for selecting a final machine-learning model for inference implementation.

In typical workflows, Deep Learning researchers select one of these intermediate machine-learning models based on observation of the training loss, validation loss, and validation accuracy curves. The present disclosure describes an embodiment of a method for model selection that eliminates the inherent subjectivity of the model-selection process. An embodiment selects among the intermediate machine-learning models based on maximizing the known F1 metric on the validation set. The F1 metric is defined by the following equation:

$$F_1 = 2 \; P \cdot R / (P + R) \quad (1)$$

where P is precision (positive predictive value) and R is recall (sensitivity). The inclusion of precision in the model-selection metric means that the performance on negative samples is taken into account as well as positive samples. This can be important for a diagnostic device because precision is a measure of certainty in the prediction of a positive outcome.

For example, regarding pleural effusion, a medical professional, such as a pulmonologist or other doctor, typically decides upon the most appropriate intervention in response to his/her assessment of the severity of the pleural effusion. Therefore, in an embodiment, the neural network(s) implemented by the ultrasound system 130 (FIG. 8) are trained to estimate the severity of a detected one or more pleural effusions using an unsupervised machine-learning approach. The core machine-learning models of the ultrasound system 130 are trained using a large number of example ultrasound images (taken from ultrasound videos) that an expert, such as pulmonologist or sonographer, has carefully annotated for lung features and pathologies. This set of annotated ultrasound images is called the training set of images. The process for training the machine-learning models is described below, but here it is noted that the training set of ultrasound images contains, at least ideally, a great deal of feature diversity, which typically provides for training that results in good deep-learning models. In particular, the training set of images for pleural effusion contains examples with a range of severities of pleural effusion from mild to severe. In an embodiment, the examples of pleural effusion in the training set are clustered based on the values of attributes extracted from their annotated bounding boxes. The clustering attributes may include, but are not limited to, the following: height of bounding box, width of bounding box, area of bounding box, perimeter of bounding box, aspect ratio of bounding box, ratio of dark pixels to total pixels, or any combination thereof.

Referring to FIG. 19A, described below is an embodiment of a workflow 1900 for training one or more detector CNNs, such as an SSD CNN, to detect and to classify one or more features in one or more ultrasound images.

First, a relatively large number (e.g., hundreds, a few thousand) of ultrasound video images 1902 of different lungs are acquired. For example, such training ultrasound images may be sequences of ultrasound images, or ultrasound videos, acquired from a medical-imaging laboratory.

Next, using a computer system 1904 with image-display and image-annotation capabilities, a pulmonologist (not shown in FIG. 19A), or other expert (e.g., a radiologist, sonographer) interprets the ultrasound images 1902 of the lung, analyzes each of the images, manually draws, with a computer application running on the computer system, a training bounding box around each feature that the expert ultrasound-image interpreter detects (e.g., A-line, B-line), and labels/annotates each detected feature (e.g., A-line, B-line, severe pleural effusion) with the computer application. For example, the label/annotation for a feature typically includes the class (e.g., A-line, B-line) of the feature. The result of the pulmonologist's actions are annotated ultrasound images, also called original training images, 1906. Said another way, the training of machine-learning detector models for automated medical image diagnosis often involves establishing the "ground truth" for a training set of images. "Ground truth" refers to the medically accepted diagnosis as established by an expert. In the case of ultrasound lung images and videos, the expert would be a sonographer, pulmonologist, or other physician or medical professional, who annotates features in the images with the respective "ground truths" for those features. The computing system 1904 can convert the bounding boxes drawn by the expert into relative coordinates, such as Cartesian coordinates, of one or more points (e.g., corners) of the bounding box.

Then, at a step 1908, a training system, perhaps the computer system 1904, augments the original training images (annotated images) 1906 to increase the number of training images without acquiring additional images. That is, augmentation effectively allows generating a number of final training images that this significantly greater than the number of original, or raw, training images from which one generates the final training images 1910. The training of convolutional-neural-network (CNN) models typically uses a great deal of data. A conventional technique for increasing the size and diversity of the training set is to generate artificial training data based on transformations of the real training data. This process is generally referred to as augmentation. For example, one could generate one hundred final training images 1910 from ten original training images 1906. Consequently, augmentation can reduce the cost and effort of obtaining the original training images 1906 by reducing the number of original training images required for training. For example, one can augment one or more of the original training images 1906 by filtering each original training image to blur it. Other techniques for augmenting one or more of the original training images 1906 include adding noise to an image, altering the brightness of one or more pixels of the image, altering the image contrast, rotating the image in the image plane, and rotating the image according to a pseudo three-dimensional technique, in a random or deliberate manner. For example, augmentation software running on the computer system 1904 can add noise or other pseudo-random artifacts to the existing original training images 1906 to increase the diversity of the pool of final training images 1910. Each augmented original training image constitutes a separate final training image 1910 as described above. For example, an original acquired and annotated training image 1906 can be augmented in multiple different ways to generate multiple respective final training images 1910 from the single original acquired and annotated training image. Other types of image-augmentation transforms include image flips, random image crops, random image scaling, jittering of the position of the expert-drawn bounding box, and random grayscale contrast modifications. Suitable augmentation schemes are highly domain- and target-dependent as the transformations applied are designed to preserve the classifications of the target features. That is, augmentations applied to lung ultrasound images are designed so as not to alter the identity of lung features or artifacts. Thus, augmentation of ultrasound images typically eschews the image being flipped vertically as this could render the ultrasound image unrealistic. But horizontal flips of lung ultrasound images are typically suitable for augmentation. Likewise, ultrasound images acquired with a curvilinear transducer typically can be safely rotated by small angles around the origin of the polar coordinate system. Scale transformations applied to B-lines and other features are suitable if the scale transformations respect the relative dimensions of the various structures and artifacts in the image. For example, B-lines generally extend from the pleural line down to the maximum depth of the image, so scale transformations for image augmentation should respect this constraint. Scaling transformations that narrow or widen B-lines are also suitable as this typically does not alter the identity of a B-line.

Next, the training system feeds the augmented (final) training images 1910 to the detection-model CNN trainer 1914. During an SSD CNN detection-model training session, a series of continuously improving intermediate machine-learning detector models 1916 are generated as described above in conjunction with the automated model-selection process that is based on maximizing the F1 metric. As is known, the weights of the base network in the SSD CNN may be set to pre-trained values to accelerate the detector-model training process. Although such pre-trained CNN weights are typically not trained on ultrasound images of a lung, training on other types of images nonetheless can reduce, significantly, the time it takes to train the detector SSD CNN models 1916 on ultrasound images as compared to starting with raw, untrained CNN weights.

The training system executes each intermediate detector model 1916 to effectively compare the CNN's feature-position and feature-classification result(s) for a final training image 1910 to the annotations of the same final training image. In more detail, at any one time, the SSD CNN is the current detector model 1916. As described below, after each training iteration of one or more final images 1910, the training system updates the SSD CNN to generate a new model 1916. This continues for a number of models 1916, which are stored in memory, until the error rates of the most recent models are within suitable ranges. Then, one selects one of the most recent models 1916 as the model that is the final SSD CNN to be used to analyze images.

Initially, for each detected feature from a number of final training images 1910, it is likely that the respective SSD CNN position and classification results are significantly different from the annotation position and classification (e.g., the bounding box drawn by, and the classification indicated by, the pulmonologist or other expert using the computing system 1904).

Over a large number of final training images 1910 and over a large number of training iterations, and, therefore, over a large number of differences between the training position and classification results yielded by each detector SSD CNN model 1916 and the training-image position and classification annotations, the training computer system alters the parameters (e.g., the inter-neuron connection weights of the neural-network model) of the SSD CNN 1916 in a manner that reduces the respective differences between the position and classification outputs (e.g., bounding boxes and the confidence values) and the training-image classification annotations (e.g., the bounding boxes and the confidence values of the annotated final training images 1910), until each of these differences reaches a respective minimum error rate. A CNN, however, does not alter its structure as it learns. In neural terminology, the number of neurons in the CNN is not changed during training, and the neurons themselves are not modified during training; only the signal weights imparted by the synapses between the neurons are modified. Learning alters the weights in an effort to reduce the error. But, as described below, the error rate typically never reaches zero except for the most trivial of problems.

FIG. 20 is a plot 2000 of the training-loss 2002 (ordinate) versus the number of training iterations (abscissa) used to train the detector SSD CNN 1916 implemented by the ultrasound system 130 (FIG. 8), and of the validation-loss 2004 (ordinate) versus the number of training iterations (abscissa) used to train the detector SSD CNN, according to an embodiment. The training-loss 2002 is, effectively, the combined feature-position and feature-classification error rate that the trained SSD CNN 1916 yields for training images, and the validation-loss 2004 is, effectively, the combined feature-position and feature-classification error rate that the trained SSD CNN yield for images other than the training images. Typically, for a given number of training iterations along the abscissa, the validation loss 2004 is higher than the training loss 2002 because the SSD CNN 1916 is trained with, and, therefore, is effectively customized for, the final training images 1910, whereas the SSD CNN is not trained with, and, therefore, is not customized for, the validation images.

Referring to FIG. 20, a training computer system (not shown in FIG. 20) can plot the training error rate, or training loss, 2002 as the training is ongoing. Typically, the training error rate 2002 starts out high, then falls off, and then more-or-less flattens out (although there still can be oscillations in the training loss as is evident in the plot 2000). The trained detector SSD CNN 1916 (FIG. 19A) attain its minimum training loss in the flatter part 2006 of the training-loss curve 2002.

Referring to FIGS. 19A and 20, in an embodiment a tool (not shown in FIGS. 19A and 20) that is part of, or that is provided with, the SSD CNN 1916 being trained, effectively back-propagates changes to the SSD CNN's inter-neuron (synapse) connection weights from the output node(s) of the SSD CNN to the input node(s) of the SSD CNN, the average magnitude of the changes being related to the magnitude of the errors between the actual SSD CNN output(s) and the outputs that the SSD CNN should have rendered for the training images, i.e., the bounding-box-location and confidence values that the CNN outputs.

The ultrasound system 130 (FIG. 8) effectively deactivates the error backpropagation tool during inference (e.g., non-training) operation of the SSD CNN 1916, although the forward-propagation function of the SSD CNN is retained during inference operation.

Still referring to FIGS. 19A and 20, in an embodiment, the training computer system, which can be the same as, or different from, the ultrasound system 130 (FIG. 8), computes the validation loss 2004 every V training iterations, where V is a hyperparameter of the training process that a human trainer/user can select; for example, one can select V=1000. To obtain a validation loss 2004, one uses the latest training models of the SSD CNN to analyze a set of images that are different from the training images. That is, the validation images, and the loss associated with them, are not used to train the SSD CNN 1916 but are used as an indication of how the SSD CNN will perform "in the field" on images that are not the training images. Generally, validation loss 2004 is higher than training loss 2002 (as is evidenced by the validation-loss generally being higher than the training-loss) because during the training, the above-described changes to the SSD CNN's inter-neuron connection weights are to cause the SSD CNN 1916 to better analyze the final training images 1910, so it is expected that the training loss will be lower than the validation loss since the SSD CNN is effectively being customized to the training images.

In addition to the validation loss 2004, the SSD CNN training tool can provide additional statistics from the validation run, such as the precision P (also known as purity, or positive-predicted value), and the recall R (also known as sensitivity), which are described above in conjunction with equation (1). Algorithms for determining these statistical values are conventional, and, therefore, are not described in detail herein.

Referring to FIGS. 19A and 20, although SSD CNN 1916 is described as being a single CNN, the SSD CNN can be, at least effectively, a combination of a detector CNN and a classifier CNN, and the training losses of the detector CNN and classifier CNN can be mathematically combined, in a conventional manner, to yield the combined training loss 2002; similarly, the validation losses of the detector CNN and classifier CNN can be mathematically combined, in a conventional manner, to yield the combined validation loss 2004. For example, in the case of an SSD based architecture such as the SSD CNN 1916, usually there is a CNN base network that works as a feature extractor for the classification and localization sub-branches. An SSD CNN applies small convolutional filters (detection filters) to the output feature maps of a base feature extractor to predict object-category scores and bounding-box offsets. The convolutional filters are applied to feature maps at multiple spatial scales to enable the detection of objects with various sizes. For example, in an embodiment, the feature extractor is the respective front-end portion of an SSD CNN (e.g., a single or multi-class SSD CNN), the detection and classification networks are respective back-end detection portions of the same SSD CNN, and the entire SSD CNN architecture is trained on final training-image frames, such as the final training images 1910, as described above in conjunction with FIGS. 19A and 20.

Referring to FIG. 19B, described below is an embodiment of a workflow 1940 for training one or more classifier CNNs, such as a CNN used to classify lung sliding in a sequence of ultrasound images (e.g., in an ultrasound video), or in one or more M-mode images. Components common to FIGS. 19A and 19B are labeled with like reference numbers.

First, a relatively large number (e.g., hundreds, a few thousand) of ultrasound videos 1902 of different lungs are acquired. For example, such training ultrasound videos are time sequences of ultrasound images of respective lungs, and may be acquired from a medical-imaging laboratory.

Next, using a computer system 1904 with image-display and image-annotation capabilities, a pulmonologist (not shown in FIG. 19B), or other expert (e.g., a radiologist, sonographer) interprets the ultrasound images 1902 of the lung, analyzes each of the images, and with the computer application, annotates each video to indicate whether the video indicates lung sliding. The result of the pulmonologist's actions are annotated ultrasound videos, also called original training videos, 1906. Said another way, the training of machine-learning classifier models for automated medical video diagnosis often involves establishing the "ground truth" for a training set of videos. "Ground truth" refers to the medically accepted diagnosis as established by an expert. In the case of ultrasound lung videos, the expert would be a sonographer, pulmonologist, or other physician or medical professional, who annotates lung sliding in the videos with the respective "ground truths" for lung sliding.

Then, at a step 1908, a training system, perhaps the computer system 1904, augments the original training videos (annotated videos) 1906 to increase the number of training videos without acquiring additional videos. That is, augmentation effectively allows generating a number of final training videos 1910 that this significantly greater than the number of original, or raw, training videos from which one generates the final training videos 1910. The training of convolutional-neural-network (CNN) models typically uses a great deal of data. A conventional technique for increasing the size and diversity of the training set is to generate artificial training data based on transformations of the real training data. This process is generally referred to as augmentation. For example, one could generate one hundred final training videos 1910 from ten original training videos 1906. Consequently, augmentation can reduce the cost and effort of obtaining the original training videos 1906 by reducing the number of original training videos required for training. For example, one can augment one or more of the original training videos 1906 by filtering each original training video to blur it. Other techniques for augmenting one or more of the original training videos 1906 include adding noise to one or more images that form the video, altering the brightness of one or more pixels of one or more images that form the video, altering the contrast of one or more images that form the video, rotating one or more images that form the video in the image plane, and rotating one or more images that form the video according to a pseudo three-dimensional technique, in a random or deliberate manner. For example, augmentation software running on the computer system 1904 can add noise or other pseudo-random artifacts to the existing original training videos 1906 to increase the diversity of the pool of final training videos 1910. Each augmented original training video constitutes a separate final training video 1910 as described above. For example, an original acquired and annotated training video 1906 can be augmented in multiple different ways to generate multiple respective final training videos 1910 from the single original acquired and annotated training video. Other types of video-augmentation transforms include image flips, random image crops, random image scaling, and random grayscale contrast modifications. Suitable augmentation schemes are highly domain- and target-dependent as the transformations applied are designed to preserve the classifications of the target features. That is, augmentations applied to lung ultrasound videos are designed so as not to alter the identity of lung features or artifacts. Thus, augmentation of ultrasound videos typically eschews the images of a video being flipped vertically as this could render the ultrasound video unrealistic. But horizontal flips of the images of lung ultrasound videos are typically suitable for augmentation. Likewise, the images that form ultrasound videos acquired with a curvilinear transducer typically can be safely rotated by small angles around the origin of the polar coordinate system. Scale transformations applied to pleural line and other features are suitable if the scale transformations respect the relative dimensions of the various structures and artifacts in the images that form the video. For example, scaling transformations that narrow or widen a pleural line are suitable as this typically does not alter the identity of a pleural line.

Next, at a step 1944, the training system converts the final ultrasound videos 1910 into final ultrasound M-mode training images 1946.

Then, the training system feeds the final M-mode training images 1946 to the classifier-model CNN trainer 1948. During a CNN classifier-model training session, a series of continuously improving intermediate machine-learning classifier models 1950 are generated as described above in conjunction with the automated model-selection process that is based on maximizing the F1 metric. As is known, the weights of the classifier CNN may be set to pre-trained values to accelerate the CNN classifier-model training process. Although such pre-trained CNN weights are typically not trained on ultrasound videos, or M-mode images, of a lung, training on other types of images or videos nonetheless can reduce, significantly, the time it takes to train the respective classifier CNN on ultrasound M-mode images as compared to starting with raw, untrained CNN weights.

The training system executes, sequentially, each intermediate classifier model 1950 to effectively compare the CNN's classification result for a final training M-mode image 1946 to the annotations of the same final training M-mode image. In more detail, at any one time, the classifier CNN is the current detector model 1950. As described below, after each training iteration of one or more final M-mode images 1946, the training system updates the classifier CNN to generate a new model 1950. This continues for a number of models 1950, which are stored in memory, until the error rates of the most recent models are within suitable ranges. Then, one selects one of the most recent models 1950 as the model that is the final classifier CNN to be used to analyze images.

Initially, for each of a number of final training M-mode images 1946, it is likely that the respective classifier CNN classification result for lung sliding is significantly different from the annotation classification (e.g., the confidence value that the M-mode image indicates lung sliding) indicated by the pulmonologist or other expert using the computing system 1904.

Over a large number of final training M-mode images 1946 and over a large number of training iterations, and, therefore, over a large number of differences between the training classification results yielded by each classifier CNN model 1950 and the training-image classification annotations, the training computer system alters the parameters (e.g., the inter-neuron connection weights of the neural-network model) of the classifier CNN models 1950 in a manner that reduces the respective differences between the classification outputs (e.g., the confidence values) and the training-image classification annotations (e.g., the confidence values of the annotated final training M-mode images 1946), until each of these differences reaches a respective minimum error rate. A CNN, however, does not alter its structure as it learns. In neural terminology, the number of neurons in the CNN is not changed during training, and the neurons themselves are not modified during training; only the signal weights imparted by the synapses between the neurons are modified. Learning alters the weights in an effort to reduce the error. But, as described below, the error rate typically never reaches zero except for the most trivial of problems.

As described above, FIG. 20 is a plot 2000 of the training-loss 2002 (ordinate) versus the number of training iterations (abscissa) used to train the detector SSD CNN models 1916 (FIG. 19A) implemented by the ultrasound system 130 (FIG. 8), and of the validation-loss 2004 (ordinate) versus the number of training iterations (abscissa) used to train the detector SSD CNN.

But because the training loss and the validation loss of the classifier CNN models 1950 have generally the same curve shape (when plotted) and characteristics as the training loss and validation loss of the SSD CNN models 1916, for purposes of example, it is assumed that the classifier CNN models exhibit the training-loss 2002 and the validation loss 2004.

Referring to FIGS. 19B and 20, a training computer system (not shown in FIGS. 19B and 20) can plot the training error rate, or training loss, 2002 as the training is ongoing. Typically, the training error rate 2002 starts out high, then falls off, and then more-or-less flattens out (although there still can be oscillations in the training loss as is evident in the plot 2000). The trained classifier CNN attains a minimum training loss in the flatter part 2006 of the training-loss curve 2002.

Referring to FIGS. 19B and 20, in an embodiment a tool (not shown in FIGS. 19B and 20) that is part of, or that is provided with, the classifier CNN model 1950 being trained, effectively back-propagates changes to the classifier CNN's inter-neuron (synapse) connection weights from the output node(s) of the classifier CNN to the input node(s) of the classifier CNN, the average magnitude of the changes being related to the magnitude of the errors between the actual classifier CNN output(s) and the outputs that the classifier CNN should have rendered for the training M-mode images 1946, i.e., the confidence values that the classifier CNN outputs.

The ultrasound system 130 (FIG. 8) effectively deactivates the error backpropagation tool during inference (e.g., non-training) operation of the classifier CNN, although the forward-propagation function of the classifier CNN is retained during inference operation.

Still referring to FIGS. 19B and 20, in an embodiment, the training computer system, which can be the same as, or different from, the ultrasound system 130 (FIG. 8), computes the validation loss 2004 every V training iterations, where V is a hyperparameter of the training process that a human trainer/user can select; for example, one can select V=1000. To obtain a validation loss 2004, one uses the latest training models 1950 of the classifier CNN to analyze a set of M-mode images that are different from the training M-mode images 1946. That is, the validation images, and the validation loss associated with them, are not used to train the classifier CNN but are used as an indication of how the classifier CNN will perform "in the field" on M-mode images that are not the M-mode training images 1946. Generally, validation loss 2004 is higher than training loss 2002 (as is evidenced by the validation-loss generally being higher than the training-loss) because during the training, the above-described changes to the classifier CNN's inter-neuron connection weights are to cause the classifier CNN models 1950 to better analyze the final M-mode training images 1946, so it is expected that the training loss will be lower than the validation loss since the classifier CNN is effectively being customized to the training M-mode images.

In addition to the validation loss 2004, the classifier CNN training tool can provide additional statistics from the validation run, such as the precision P (also known as purity, or positive-predicted value), and the recall R (also known as sensitivity), which are described above in conjunction with equation (1). Algorithms for determining these statistical values are conventional, and, therefore, are not described in detail herein.

Referring again to FIG. 9, step 220, and to FIGS. 19A-20, in an embodiment, the lung-sliding classifier CNN is trained on M-mode final training images 1946 in parallel with the training on the final images 1910 of the SSD CNN(s) for the features other than lung sliding; the M-mode final training images are typically different than the final training images for the SSD CNN architectures that detect and classify, for example, other features such as A-line, B-line, pleural line, consolidation, and plural effusion.

The training of the lung-sliding CNN and the lung-feature detector SSD CNN(s) does not necessarily occur simultaneously, and, as described above, need not occur with the same final training images.

The training and validation of the lung-sliding classifier CNN, and the one or more detector-and-classifier SSD CNNs, can take a significant time, for example, hours, days, or even one or more weeks, depending on the number of final training images 1910 and 1946 used, and the levels of training loss 2002 and validation loss 2004 deemed suitable for an application for which the lung-sliding classifier CNN and the one or more detector-and-classifier SSD CNNs are trained.

Once the training error rates (e.g., the training loss 2002 and the validation loss 2004) flatten out, there are small variations, also called oscillations, in the training error rate from training iteration to training iteration.

Therefore, one typically has many choices of which exact CNN version/model(s) to select for use in analyzing images and detecting and classifying features during inference. That is, each training iteration yields a CNN version/model that is typically slightly different from all other CNN versions/models, even though these CNN versions/models may all yield a comparable training loss 2002 and validation loss 2004.

Consequently, in an embodiment, a conventional algorithm can be used to select a respective suitable CNN version/model for the lung-sliding classifier CNN and for the feature-detector-and-classifier SSD CNN(s).

For example, in an embodiment, a conventional F1 selection algorithm is used to select the CNN versions/models for the SSD CNN(s) and for the classifier CNN from among the versions/models that give an approximately minimum error, where the F1 metric is defined by the following equation, which is the same as equation (1) above:

$$F1 = 2 \cdot P \cdot R/(P+R) \quad (2)$$

where P is precision and R is recall as explained below.

For the SSD CNN, a respective F1 metric is calculated for each of the features (e.g., A-line, B-line, pleural line, consolidation, and plural effusion) that the ultrasound system 130 (FIG. 8) is to be configured to detect, these respective F1 metrics are conventionally combined, and a respective SSD CNN version/model is selected in response to the resulting combination of the F1 metrics (the classifier CNN version/model for classifying lung sliding is selected separately).

Combining the respective F1 metrics for the to-be-detected features allows one to weight the different to-be-detected features in terms of importance, so that an SSD CNN version that is more accurate with heavily weighted features is favored over an SSD CNN version that is less accurate with the heavily weighted features, even if the latter SSD CNN version is more accurate with lightly weighted features.

For example, in an embodiment, accurate detection and identification of pleural effusion and consolidation are weighted more heavily than detection and identification of other features such as A-line, B-line, and pleural line, because the former features are considered by many in the medical community to indicate more serious lung conditions.

Using the conventional F1 metric can provide a good balance between good sensitivity on the positive images (accurately detecting and classifying a particular feature, such as B-line, in images that actually include the particular feature) and a low false-positive rate on the negative images (not falsely detecting/classifying a particular feature, such as B-line, in images that lack the particular feature). That is, one typically would like to choose a model of the SSD CNN that is good at detecting and classifying features where the features are present in images, and that is good at not falsely detecting and falsely classifying features where the features are lacking from images.

Applying a conventional F1 metric for each feature that an SSD CNN is trained to detect and to classify allows one to select a version/model for the SSD CNN that provides different sensitivity and false-positive-rejection weights to the feature/objects according to the following equation:

$$\text{Total\_Weighed\_F1} = [(W_1 \cdot (F1 \text{ for object class (e.g., feature)} 1) + (W_2 \cdot (F1 \text{ for object class (e.g., feature)} 2) + \ldots + (W_C \cdot (F1 \text{ for object class (e.g., feature)} C)] / (W_1 + W_2 + W_3 \ldots + W_C) \quad (3)$$

Per equation (3), the higher the weight $W_i$, the higher the emphasis that is placed on the accurate detection and classification, and the accurate rejection of false positives, of the corresponding object class. For example, if $W_1$ is greater than $W_2$, then equation (3) tends to give higher values of Total Weighted F1 to SSD CNN models that have a higher accuracy regarding object class (e.g., feature) 1 than regarding object class (e.g., feature) 2. That is, if $W_1$ is greater than $W_2$, then equation (3) tends to select SSD CNN versions/models that have a higher F1 metric regarding object class (e.g., feature) 1 than regarding object class (e.g., feature) 2.

For example, in an embodiment, the detector training model that gives the highest value of Total Weighted F1 according to the following equation is selected as the model of the SSD CNN to use "in the field:"

$$\text{Total Weighted } F1 = (2 \cdot F1 \text{consolidation} + 2 \cdot F1_{effusion} + 1 \cdot F1_{peura\_line} + 1 \cdot F1_{A\text{-}line} + 1 \cdot F1_{B\text{-}Line} + 1 \cdot F1_{merged\_B\text{-}line})/8 \quad (4)$$

Equation (4) emphasizes accuracy of consolidation and pleural-effusion detection over pleural-line, A-line, B-line, and merged B-line by a ratio of 2 to 1, because some medical experts have indicated that this weighting emphasizes detecting and classifying life-threatening conditions over less-serious conditions. Of course, other embodiments can use other weight values.

Because the lung-sliding classifier CNN is trained to classify only lung-sliding, one may decide to select the classifier model 1950 that yields a lowest training loss or validation loss instead of using the above-described weighted-F1 technique.

Figure 21:
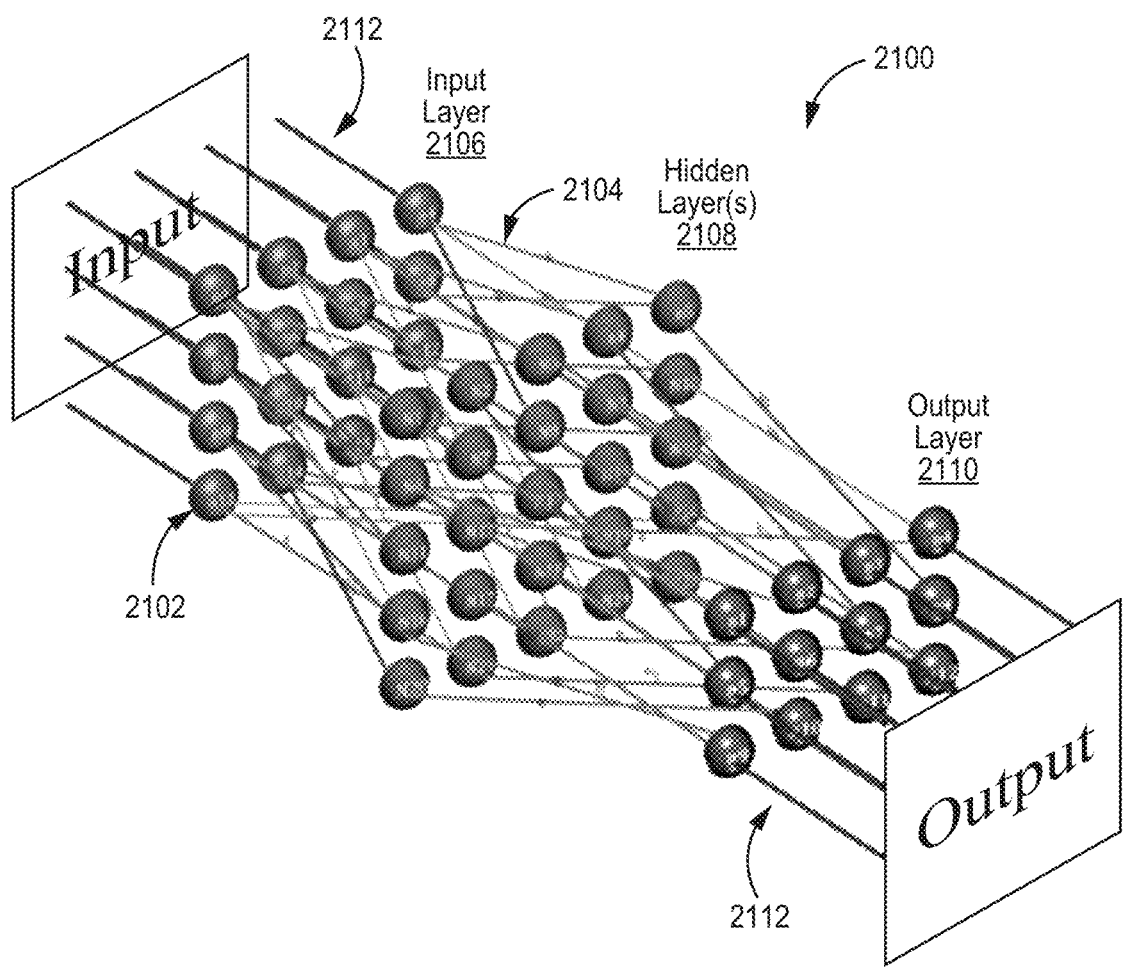
FIG. 21 is a general diagram of a CNN, such as an SSD CNN, according to an embodiment.

FIG. 21 is a general diagram of a CNN 2100, such as an SSD CNN, according to an embodiment. The circular items represent neurons 2102, which are, or which represent, fixed algorithms that each combine the inputs to the neurons to generate one or more outputs, and the connections lines 2104 between an output of a neuron in one layer and the respective input of one or more neurons in the next layer represent synapses, which are equations with trainable coefficients that operate on the output/result from a neuron in one layer and provided a new output/result to a neuron in a following layer. The CNN 2100 is logically arranged in layers: an input layer 2106, one or more intermediate, or hidden, layers 2108, and an output layer 2110. The number of neurons 2102 in each layer can be different from layer to layer but is fixed in that the number of neurons in each layer is not changed in response to training, and the operations at each layer of the CNN from input (left in FIG. 21) to output (right in FIG. 21) are performed simultaneously (at least conceptually). Furthermore, connection lines 2112 to the input layer 2106 and from the output layer 2110 can weight the respective inputs to the input layer and the outputs from the output layer; that is, the weights are coefficients by which the signals input to the input layer and output from the output layer are respectively multiplied. At least conceptually, at a time $t_0$, the weightings of the signals input to the input layer 2106 are performed; at a time $t_1$, operations of the synapses 2104 between the input layer 2106 and the first hidden layer 2108 are performed; at a time $t_2$, operations of the neurons 2102 in the first hidden layer 2108 are performed; at one or more times $t_3$ the operations of the synapses 2104 between the first hidden layer and the second hidden layer (if present) are performed, and so on for any additional hidden layers; at a time $t_4$, the operations of the synapses between the $n^{th}$ (last) hidden layer and the output layer 2110 are performed; and at a time $t_5$, the weightings of the signals output from the output layer 2110 are performed. Also, a fully connected (FC) layer is a layer in which each neuron 2102 is connected to every neuron in the previous layer. In an embodiment, any one or more of the hidden layer(s) 2108 and the output layer 2110 can be a fully connected layer, although a CNN can contain no fully connected layers. Furthermore, a CNN can include parallel layers that, at least conceptually, are separate layers that lie on a same layer plane. For example, in an embodiment, parallel layers of the SSD CNN respective perform feature detection and feature classification; said another way, the SSD CNN can be configured to perform feature detection and feature classification in parallel instead of in series. Furthermore, the training loss of an SSD CNN includes a classifier-training-loss component and a detector-training-loss component. The combined, or total, training loss 2002 of FIG. 20 is a conventional mathematical combination of these training-loss components. Similarly, the validation loss of an SSD CNN includes a classifier-validation-loss component and a detector-validation-loss component. The combined, or total, validation loss 2004 of FIG. 20 is a conventional mathematical combination of these to validation-loss components. In contrast, a classifier CNN, such as the classifier CNN trained to classify lung sliding, has only one training-loss component and only one validation-loss component.

Still referring to FIG. 21, as discussed above, in an embodiment, the lung-sliding classifier (see step 220 of FIGS. 9 and 16) is a conventional classifier CNN, which is configured to process an input ultrasound image with multiple layers of convolutions followed by non-linear operations. The output of each layer is a multi-channel feature map. Successive layers of the CNN extract progressively larger and more abstract features from the image. Later feature maps are also less sensitive to minor spatial transformations of the features they are detecting, where spatial transformations include translation, intensity change, or distortion. The last few layers of a classifier CNN are where the classification takes place. These are usually fully-connected (FC) layers. As described below, these last few layers are removed before using the classifier CNN as the front end (base network) of an SSD CNN.

For purposes of the following discussion in which an SSD CNN is used for feature detection and classification in images, each convolutional layer of the SSD CNN corresponds to a feature map of the image, and each plane of neurons in a layer can be referred to as a channel of the feature map. Per above, each layer can have any number of neuron planes and, therefore, can have any number of channels.

Figure 22:
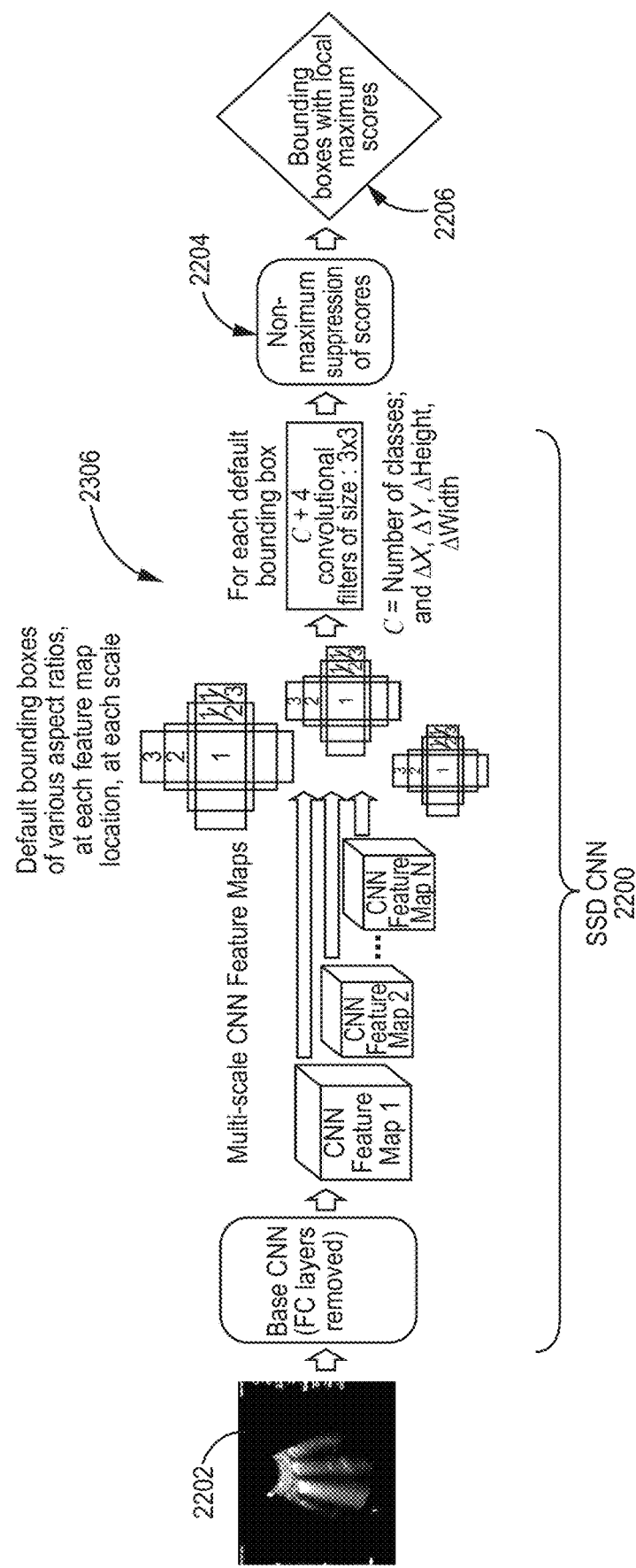
FIG. 22 is a diagram of a single multi-class SSD CNN, according to an embodiment.

FIG. 22 is a diagram of a multi-class SSD CNN 2200, according to an embodiment. As described above, the multi-class SSD CNN 2200 is configured both to detect features and to classify the detected features.

In an embodiment of the operation of the SSD CNN 2200, input to the SSD CNN 2200 is an ultrasound image/frame 2202. A premise for the SSD CNN 2200 is that the image 2202 can include any number of features (not shown in FIG. 22) that the SSD CNN is trained, or otherwise configured, to detect and to classify, and each feature can have any scale and any aspect ratio. Although a feature can have an arbitrary shape, the SSD CNN 2200 outputs a minimum-dimension rectangle (e.g., boundary box not shown in FIG. 22) that contains the feature. For example, if the detected feature is a perfect circle, then the SSD CNN 2200 would identify the detected feature by defining a minimum-dimension rectangle, in this case a square, having sides each tangent to a respective point along the circumference of the circle, such that the square is the smallest possible rectangle that can contain the entire circle. The SSD CNN 2200 also outputs C scores that indicate the probability that the detected feature belongs to one of the classes that it has been trained, or otherwise configured, to detect and to classify, where C is the number of classes that the SSD CNN 2200 has been trained, or otherwise configured, to detect.

The SSD CNN 2200 is built on top of a conventional image-classification network, albeit a conventional CNN with its image-classification layers (which, per above, can be fully-connected layers) removed. Such a truncated image-classification CNN is called the "base network," and the base network can have any suitable CNN architecture such as, but not limited to, AlexNet, VGG, Inception, or Residual. The SSD CNN 2200 includes an additional one or more convolutional layers at the end of the base-network CNN. These additional layers are trained, or otherwise configured, to perform the feature-detection and the feature classification operations in the SSD CNN 2200, and are called the "predictor convolutional layers" or the "predictor layers."

Figure 23:
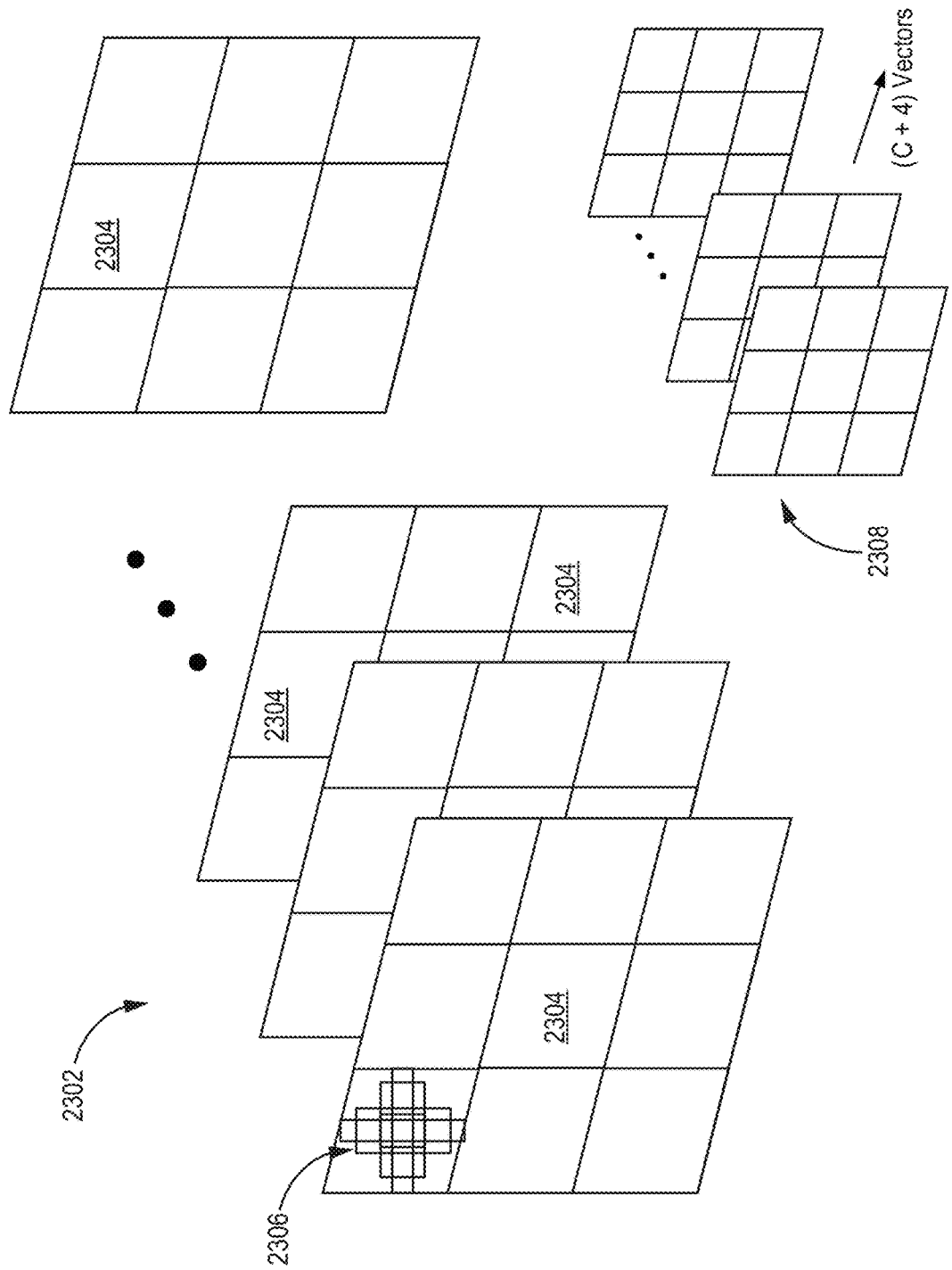
FIG. 23 is a diagram of a feature map, according to an embodiment.

Referring to FIG. 23, the predictor convolutional layers are configured to produce one or more feature maps 2302 (only one feature map is shown in FIG. 23) at progressively different sizes, that is, at progressively different resolutions, and this allows the SSD CNN 2200 (FIG. 22) to detect features at multiple spatial scales. For example, in an embodiment, a first predictor layer, and thus a first feature map, may have a feature-map resolution of 38×38 grid cells 2304, the next predictor layer may have a resolution of 19×19 grid cells, the next predictor layer may have a resolution of 10×10 grid cells, the next predictor layer may have a resolution of 5×5 grid cells, the next predictor layer may have a resolution of 3×3 grid cells (this is the predictor layer shown in FIG. 23), and a final one or more predictor layers may have a resolution of 1×1 grid cells (for clarity, FIG. 23 includes a feature map 2302 having a resolution of 3×3 grid cells, it being understood that the SSD CNN 2200 of FIG. 22 can generate more than one feature map that each have respective resolutions as described).

Referring to FIGS. 22-23, in more detail, in an embodiment each channel of a feature map, such as the feature map 2302 is, effectively, a pseudo version of the entire ultrasound image 2202. One can think of each channel as a respectively filtered version of the image at a respective resolution. The SSD CNN 2200 effectively generates each grid cell 2304 of a feature map 2302 by down sampling and filtering the pixels in the corresponding region of the image 2202, although in actuality, the SSD CNN effectively generates the grid cells of a feature map in one layer by down sampling the cells of the feature map of a prior layer. For example, if a grid cell 2304 of a feature map 2302 represents a corresponding image region that is $\frac{1}{100} \times \frac{1}{100}$ the area of the ultrasound image 2202, then the SSD CNN 2200 derives the values (e.g., pseudo pixels) associated with the grid cell by effectively down sampling the pixels in (e.g., that constitute) the same $\frac{1}{100} \times \frac{1}{100}$ region of the ultrasound image.

Further as shown in FIG. 23, one can view the feature-map channels associated with a layer of the SSD CNN 2200 (FIG. 22) as a stack, or as a three-dimensional representation of the two-dimensional ultrasound image 2202 (FIG. 22).

Still referring to FIGS. 22-23, in the example embodiment being considered, the 38×38 grid-cell feature map is tuned to the smallest features in the ultrasound image 2202 because this grid cell has the highest resolution among the feature maps. The 19×19 grid-cell feature map is tuned to detecting features at a scale double that of the 38×38 feature map, and so on. Finally, the 1×1 feature map is tuned to detect features that fill the entire ultrasound image 2202; therefore the 1×1 feature map represents the largest scale at which the SSD CNN 2200 is trained, or otherwise configured, to detect features.

These stacks of feature-map channels are depicted in FIG. 22 as the cubic boxes labeled "CNN Feature Map 1," "CNN Feature Map 2, . . . , CNN Feature Map N, with a progressively lower map resolution, and thus with a progressively larger associated spatial scale, as the value of N increases (e.g., as one moves from left to right in FIG. 22).

And FIG. 23 is, effectively, an expansion of one of the cubic boxes in FIG. 22.

Referring again to FIGS. 22-23, in every channel of a feature map (such as the feature map 2302), at every grid cell 2304, at every scale, there is associated a multiplicity of default bounding boxes 2306 with respective aspect ratios $\alpha_i$, so that the SSD CNN can detect features of any aspect ratio at any location and at any scale. These bounding boxes 2306 are schematically illustrated in FIG. 22 near the logical center of the SSD CNN 2200, where the aspect ratio of a bounding box is indicated by a whole number or a fraction, i.e. 3, 2, 1, ½, ⅓. Tall, narrow bounding boxes 2306 are tuned to tall, thin features located anywhere in the ultrasound image 2202 at any scale, whereas short, wide bounding boxes are tuned to elongated features anywhere in the ultrasound image at any scale, and so forth. The entire collection of default bounding boxes 2306 is designed to capture (e.g., to allow the SSD CNN 2200 to detect) any feature with an arbitrary aspect ratio, an arbitrary size (relative to the size of the ultrasound image 2202), and at any location in the ultrasound image. If a detected feature in the ultrasound image 2202 has an orientation that is different from the orientations of the bounding boxes 2306, then the SSD CNN 2200 still generates a minimum-dimension bounding box around the detected feature. For example, if the detected feature is slanted in the ultrasound image 2202, then the SSD CNN 2200 fits the detected feature with a bounding box 2306 with sides that are parallel to the sides of the image, e.g., that are aligned with the vertical and horizontal axes of the image; that is, the described embodiment of the SSD CNN does not use slanted bounding boxes, e.g., does not use bounding boxes with any slanted sides.

Referring again to FIG. 23, for each feature map 2302, small (e.g., 3×3) convolutional kernels 2308 (the dimensions of the kernels are independent of the corresponding layer of the SSD CNN, and may be the same as, or different from, the dimensions of other kernels) are applied to the feature map to produce either classification scores (e.g., the probability of a detected feature belonging to a particular class) or a relative offset to the coordinates of the default bounding box 2306. Each default bounding box 2306 is considered to be centered at its feature-map position and to have a size proportional to the scale of the feature map; the relative offsets indicate the distance that the center of the actual bounding box that the SSD CNN 2200 determines for a feature deviates from the center <x,y> of the default bounding box and the amount by which the width and height of the actual bounding box deviate from the width and height, <width, height>, of the default bounding box.

As an example given for the sake of concreteness and without any implied limitation to the scope of this disclosure, suppose a (m=19)×(n=19) feature map 2302 has 361 (19×19) grid cells. Every cell is transformed to various aspect ratios (k=5, $a_i$=3, 2, 1, ½, ⅓) before processing through the sequence of three convolutional layers, each having 256 kernels. Therefore, a 19×19 feature map has 361×5×3×256=1,386,240 kernels. The output of the last convolutional layer yields a vector of size (C+4) for every aspect ratio box.

The result of the application of the kernels by the SSD CNN 2200 is (m=19)×(n=19)×(k=5)=1,805 resulting (C+4)-vectors (e.g., 1,804 vectors of length C+4), one vector for each aspect-ratio bounding box 2306 of each grid cell 2304 of the feature map 2302 (notice this is not per feature-map channel).

An explanation of the factor (C+4) is as follows. CNN layers map the aspect-ratio bounding box (which effectively defines the detected feature) to C (confidence values)+4 (location offsets). Each confidence score is a value between 0-1. As part of learning process, predicted confidence values are matched with the actual class labels provided by the expert radiologists (or other experts). Location offsets (Δx, Δy, Δwidth, Δheight: these relative offsets can have both positive and negative values) provides normalized co-ordinates for the classified object.

The application of the kernels described above will produce 1,805 potential feature detections.

The same algorithm pattern applies to all of the feature maps at all of the different scales as described above. That is, the above-described algorithmic sequence repeats until resulting (C+4) vectors, one for each aspect-ratio bounding box in each cell, are generated by, and output from, the SSD CNN 2200 for each feature map such as the feature map 2302. Because each feature map represents a different resolution and, therefore, a different scale, of the ultrasound image 2202, the number of feature-map grid cells 2304, and thus the number of resulting vectors, are different from feature map to feature map.

Referring to FIG. 22, in response to the SSD CNN 2200 generating, for each default bound box, the C+4 convolutional kernels 2308 (FIG. 23), at a step 2204, the ultrasound system 130 (FIG. 8) determines whether there is redundancy in the detected and classified features, according to an embodiment. That is, multiple feature detections may actually correspond to the same feature. The ultrasound system 130 makes this determination by applying a Non-Maximum-Suppression algorithm, such as the algorithm described above in conjunction with FIG. 18, to determine which of the determined, precise bounding boxes in a spatially close group of determined bounding boxes most likely represents the detected feature. For example, the ultrasound system 130 may select the one of the detected features having the highest confidence value (e.g., a peak value) in a local spatial region (e.g., a "hill" of a confidence map such as described above in conjunction with FIG. 18) as being associated with the bounding box that encloses/defines the actual detected feature.

The above-described step 2204, in which the classified features are "pruned" to eliminate redundancy, is the last step of analysis that the ultrasound system 130 (FIG. 8) performs in conjunction with the SSD CNN 2200 to detect and to classify predetermined features (e.g., A-line, B-line, pleural line, consolidation, and pleural effusion) in the ultrasound image 2202, according to an embodiment.

The final outputs 2206 of the ultrasound system 130 (FIG. 8), after executing the SSD CNN 2200 and the Non-Maximum Suppression algorithm, are the C+4 vectors that classify the detected feature(s). These final outputs 2206 can be input to an algorithm that, for example, renders a diagnosis of one or more conditions or pathologies of the lung represented by the ultrasound image 2202.

Referring to FIGS. 19 and 22, while the SSD CNN 2200 is being trained, the final output C+4 vectors are effectively compared to the known, true, C+4 vectors corresponding to known feature(s) in a training image.

As stated above, for each training image, an expert, such as a pulmonologist, identifies features in the training image by drawing a precise box around each of the features, and classifies the features. For example, if the expert determines that a feature is a B-line, then the annotation system sets the training confidence value for B-line to "1," and sets all other confidence values to "zero" for the specific bounding box. The annotation system also records the precise location and dimensions of the training bounding box drawn by the expert(s) for the all features.

Thereafter during the training, the SSD CNN 2200 yields its version of the bounding box and of the confidence values for the same feature. Differences between the training bounding box and the yielded bounding box, and differences between each of the training confidence values and the yielded confidence values, are determined (by the training system executing an algorithm separate from the SSD CNN, or executing a tool that is part of, or corresponds to/comes with, the SSD CNN), and the training system derives one or more loss values from these differences.

In response to the determined one or more loss values, the training system, executing the training algorithm, determines how much to "tweak" the weights (synapses) that the SSD CNN 2200 implements. For example, if the loss is low, then the training system tweaks the CNN weights only slightly; but if the loss is large, then the training system may tweak the SSD CNN weights more significantly.

The purpose, or goal, of the "tweaks" is to have the SSD CNN 2200 error converge to a lowest value, without the error effectively "oscillating" from CNN model to CNN model. So, this is akin to negative feedback where one controls the gain to allow a signal (here the error) to settle to a final value without instability such as "ringing" or oscillation.

After the SSD CNN 2200 error rate converges to a lowest value, a CNN model is selected for the SSD CNN with the F1 algorithm as described above in conjunction with equations (1)-(4).

Figure 24:
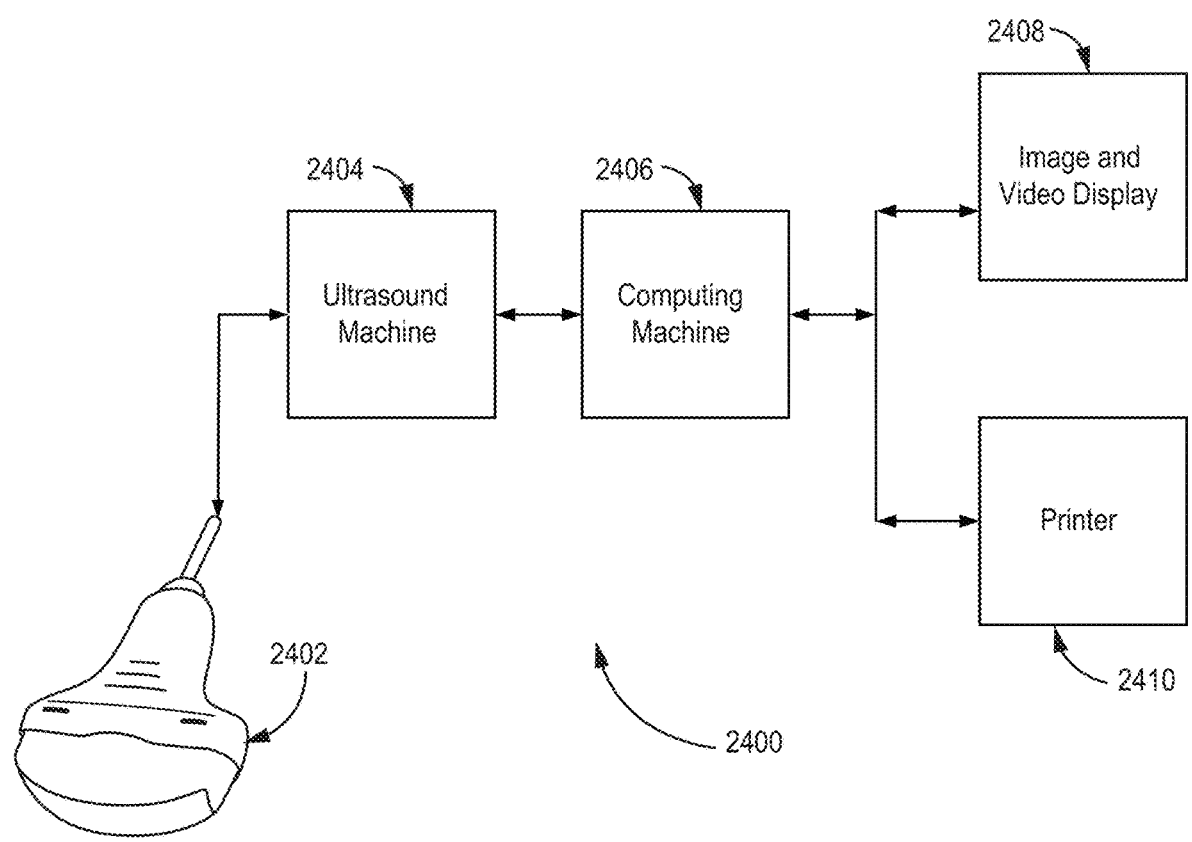
FIG. 24 is a diagram of an ultrasound system, such as the ultrasound system of FIG. 8, according to an embodiment.

FIG. 24 is a diagram of an ultrasound system 2400, which can be similar to the ultrasound system 130 of FIG. 8, according to an embodiment.

The ultrasound system 2400 includes a transducer 2402, an ultrasound machine 2404, a computing machine 2406, an image and video display 2408, and an output device such as a printer 2410.

The transducer 2402 is a conventional linear or curvilinear ultrasound transducer. And one may be able to swap out one type of transducer 2402 for another type of transducer depending on the region of a subject's body (not shown in FIG. 24) being imaged.

The ultrasound machine 2404 is a conventional ultrasound machine configured to drive the transducer 2402 to generate ultrasound signals for transmission into the tissue of a subject's body (not shown in FIG. 24), and for processing redirected ultrasound signals received by the transducer.

The computing machine 2406 is configured to perform feature detection and classification as described above; although shown separate from the ultrasound machine 2404, the computing machine can be part of the ultrasound machine, or the ultrasound machine can be part of the computing machine. For example, the ultrasound machine 2404 and the computing machine 2406 can share circuitry, such as a microprocessor, a microcontroller, or a graphics processor unit (GPU), and can be disposed within a common housing. Alternatively, the computing machine 2406 can be a separate machine, such as a tablet computer, laptop computer, or other portable computer, that is couplable to the ultrasound machine in a conventional manner, such as wirelessly or with a Universal Serial Bus (USB) cable or a Category (CAT) 5 or CAT 6 cable. The computing machine 2406 includes processing circuitry, such as one or more microprocessors or microcontrollers, non-volatile-memory circuitry, such as an EEPROM, configured to store software and configuration data such as firmware, volatile, or working, memory circuitry, and other conventional circuitry and components.

Example Embodiments

Example 1 includes a method, comprising receiving an image of a body portion, detecting, with a neural network, at least one feature in the image, and determining, with the neural network, a respective position and a respective class of each of the detected at least one feature.

Example 2 includes the method of Example 1 wherein the image of the body portion includes an image of a lung.

Example 3 includes the method of any of Examples 1-2 wherein the neural network includes a convolutional neural network.

Example 4 includes the method of any of Examples 1-3 wherein the neural network includes a single-shot-detector convolutional neural network.

Example 5 includes the method of any of Examples 1-4 wherein determining a respective position of each of the detected at least one feature includes determining a respective container that bounds the detected feature.

Example 6 includes the method of any of Examples 1-5 wherein determining a respective position of each of the detected at least one feature includes determining a respective bounding box in which the feature is disposed.

Example 7 includes the method of any of Examples 1-6 wherein determining a respective position of each of the detected at least one feature includes determining a coordinate of a respective bounding box in which the feature is disposed.

Example 8 includes the method of any of Examples 1-7 wherein determining a respective position of each of the detected at least one feature includes determining a size of a respective bounding box in which the feature is disposed.

Example 9 includes the method of any of Examples 1-8 wherein determining a respective class of each of the detected at least one feature includes determining a respective probability that the feature belongs to the respective class.

Example 10 includes the method of any of Examples 1-9 wherein determining a respective class of each of the detected at least one feature includes determining a respective confidence level that the feature belongs to the respective class.

Example 11 includes the method of any of Examples 1-10 wherein determining a respective class of each of the detected at least one feature includes: determining a respective probability that the feature belongs to the respective class; and determining that the feature belongs to the respective class in response to the respective probability being greater than a threshold for the respective class.

Example 12 includes the method of any of Examples 1-11 wherein determining a respective class of each of the detected at least one feature includes: determining probabilities that the detected at least one feature belongs to respective classes; and determining that the feature belongs to the one of the respective classes corresponding to the highest one of the probabilities.

Example 13 includes the method of any of Examples 1-12 wherein determining a respective class of each of the detected at least one feature includes determining that at least one of the detected at least one feature includes an A-line.

Example 14 includes the method of any of Examples 1-13 wherein determining a respective class of each of the detected at least one feature includes determining that at least one of the detected at least one feature includes a pleural line.

Example 15 includes the method of any of Examples 1-14 wherein determining a respective class of each of the detected at least one feature includes determining that at least one of the detected at least one feature includes a pleural effusion.

Example 16 includes the method of any of Examples 1-15 wherein determining a respective class of each of the detected at least one feature includes determining that at least one of the detected at least one feature includes a B-line.

Example 17 includes the method of any of Examples 1-16 wherein determining a respective class of each of the detected at least one feature includes determining that at least one of the detected at least one feature includes merged B-lines.

Example 18 includes the method of any of Examples 1-17, further comprising: detecting, with the neural network, at least one respective feature in each of multiple ones of the image and at least one other image of the body portion; determining, with the neural network, that each of the detected at least one respective feature is a respective detected B-line, and a respective position of each of the detected B-lines; grouping the detected B-lines in at least one cluster in response to the respective positions of the detected B-lines, each cluster corresponding to a respective actual B-line; and determining, with the neural network, a respective position of each actual B-line in response to a corresponding one of the at least one cluster.

Example 19 includes the method of any of Examples 1-18, further comprising: detecting, with the neural network, at least one respective feature in each of multiple ones of the image and at least one other image of the body portion; determining, with the neural network, that each of the detected at least one respective feature belongs to a same class, and a respective position of each of the detected at least one of the respective feature; grouping the detected features in at least one cluster in response to the respective positions of the detected features, each cluster corresponding to a respective actual feature; and determining, with the neural network, a respective position of each actual feature in response to a corresponding one of the at least one cluster.

Example 20 includes the method of any of Examples 1-19 wherein determining a respective class of each of the detected at least one feature includes determining that at least one of the detected at least one feature includes a consolidation.

Example 21 includes the method of any of Examples 1-20, further comprising: wherein determining a respective class of each of the detected at least one feature includes determining that at least one of the detected at least one feature includes a pleural effusion; and determining a severity of the pleural effusion.

Example 22 includes the method of any of Examples 1-21, further comprising: wherein the image of the body portion includes an image of a lung; and diagnosing a pathology of the lung in response to the respective determined class of each of the detected at least one feature.

Example 23 includes the method of any of Examples 1-22, further comprising: wherein the image of the body portion includes an image of a lung; and diagnosing a pathology of the lung in response to the respective position and to the respective determined class of each of the detected at least one feature.

Example 24 includes a method, comprising: receiving an image of a body portion; and determining, with a classifier neural network, a probability that the image includes a feature belonging to a particular class.

Example 25 includes the method of Example 24 wherein the particular class is lung sliding.

Example 26 includes the method of any of Examples 24-25, further comprising determining that the image includes a feature belonging to the particular class in response to the probability being greater than or equal to a threshold.

Example 27 includes a method, comprising: receiving each of an image of a body portion and at least one modified version of the image with a respective input channel of a neural network; detecting, with the neural network, at least one feature in the image in response to the image and the at least one modified version of the image; and determining, with the neural network, a respective position and a respective class of each of the detected at least one feature in response to the image and the at least one modified version of the image.

Example 28 includes the method of Example 27, further comprising generating, in response to the image of the body portion, the at least one modified version of the image.

Example 29 includes the method of any of Examples 27-28 wherein the image of the body portion includes an image of a lung.

Example 30 includes the method of any of Examples 27-29 wherein generating the at least one modified version of the image includes generating at least one filtered version of the image.

Example 31 includes the method of any of Examples 27-30 wherein the neural network includes a convolutional neural network.

Example 32 includes the method of any of Examples 27-31 wherein the neural network includes a single-shot-detector convolutional neural network.

Example 33 includes the method of any of Examples 27-32 wherein determining a respective position of each of the detected at least one feature includes determining a respective container that bounds the detected feature.

Example 34 includes the method of any of Examples 27-33 wherein determining a respective position of each of the detected at least one feature includes determining a respective bounding box in which the feature is disposed.

Example 35 includes the method of any of Examples 27-34 wherein determining a respective position of each of the detected at least one feature includes determining a coordinate of a respective bounding box in which the feature is disposed.

Example 36 includes the method of any of Examples 27-35 wherein determining a respective position of each of the detected at least one feature includes determining a size of a respective bounding box in which the feature is disposed.

Example 37 includes the method of any of Examples 27-36 wherein determining a respective class of each of the detected at least one feature includes determining a respective probability that the feature belongs to the respective class.

Example 38 includes the method of any of Examples 27-37 wherein determining a respective class of each of the detected at least one feature includes determining a respective confidence level that the feature belongs to the respective class.

Example 39 includes the method of any of Examples 27-38 wherein determining a respective class of each of the detected at least one feature includes: determining a respective probability that the feature belongs to the respective class; and determining that the feature belongs to the respective class in response to the respective probability being greater than a threshold for the respective class.

Example 40 includes the method of any of Examples 27-39 wherein determining a respective class of each of the detected at least one feature includes: determining probabilities that the detected at least one feature belongs to respective classes; and determining that the feature belongs to the one of the respective classes corresponding to the highest one of the probabilities.

Example 41 includes the method of any of Examples 27-40 wherein determining a respective class of each of the detected at least one feature includes determining that at least one of the detected at least one feature includes an A-line.

Example 42 includes the method of any of Examples 27-41 wherein determining a respective class of each of the detected at least one feature includes determining that at least one of the detected at least one feature includes a pleural line.

Example 43 includes the method of any of Examples 27-42 wherein determining a respective class of each of the detected at least one feature includes determining that at least one of the detected at least one feature includes a pleural effusion.

Example 44 includes the method of any of Examples 27-43 wherein determining a respective class of each of the detected at least one feature includes determining that at least one of the detected at least one feature includes a B-line.

Example 45 includes the method of any of Examples 27-44 wherein determining a respective class of each of the detected at least one feature includes determining that at least one of the detected at least one feature includes merged B-lines.

Example 46 includes the method of any of Examples 27-45 wherein determining a respective class of each of the detected at least one feature includes determining that at least one of the detected at least one feature includes a consolidation.

Example 47 includes the method of any of Examples 27-46, further comprising: wherein determining a respective class of each of the detected at least one feature includes determining that at least one of the detected at least one feature includes a pleural effusion; and determining a severity of the pleural effusion.

Example 48 includes the method of any of Examples 27-47, further comprising: wherein the image of the body portion includes an image of a lung; and diagnosing a pathology of the lung in response to the respective determined class of each of the detected at least one feature.

Example 49 includes the method of any of Examples 27-48, further comprising: wherein the image of the body portion includes an image of a lung; and diagnosing a pathology of the lung in response to the respective position and to the respective determined class of each of the detected at least one feature.

Example 50 includes a method, comprising: detecting at least one feature in an image of a body portion with a neural network configured to detect, in the image, at least one feature belonging to a class; and determining, with the neural network, for each of the detected at least one feature, a respective position and a respective confidence level that the respective one of the detected at least one feature belongs to the class.

Example 51 includes the method of Example 50, further comprising detecting the at least one feature and determining the respective position and the respective confidence level in response to the image.

Example 52 includes the method of any of Examples 50-51, further comprising determining, with the neural network, for each of the detected at least one feature, a respective one or more confidence levels that the respective one of the at least one feature belongs to one or more other classes.

Example 53 includes the method of any of Examples 50-52, further comprising: wherein detecting includes detecting, with the neural network, the at least one feature in the image in response to at least one modified version of the image; and wherein determining includes determining, with the neural network, for each of the detected at least one feature, the respective position and the respective confidence level in response to the at least one modified version of the image.

Example 54 includes the method of any of Examples 50-53, further comprising: wherein detecting includes detecting, with the neural network, the at least one feature in the image in response to the image and at least one modified version of the image; and wherein determining includes determining, with the neural network, for each of the detected at least one feature, the respective position and the respective confidence level in response to the image and the at least one modified version of the image.

Example 55 includes a method, comprising: generating, from each of at least one first training image, at least one second training image; determining, with a neural network, a respective probability that each of at least one feature in at least one of the at least one first training image and the at least one second training image belongs to a feature class; determining, for each of the detected at least one feature, a probability difference between the determined respective probability and a corresponding annotated probability; and changing a respective weighting of each of at least one synapse of the neural network in response to the probability difference.

Example 56 includes the method of Example 55 wherein generating includes generating at least one second training image by adding noise to one of the at least one first training image.

Example 57 includes the method of any of Examples 55-56 wherein generating includes generating at least one second training image by altering a respective brightness of at least one pixel of one of the at least one first training image.

Example 58 includes the method of any of Examples 55-57 wherein generating includes generating at least one second training image by altering a respective contrast of one of the at least one first training image.

Example 59 includes the method of any of Examples 55-58 wherein generating includes generating at least one second training image by rotating one of the at least one first training image.

Example 60 includes the method of any of Examples 55-59 wherein generating includes generating at least one second training image by adding at least one artifact to one of the at least one first training image.

Example 61 includes the method of any of Examples 55-60, further comprising: detecting, with the neural network, each of the at least one feature; determining a respective location of each of the detected at least one feature; determining, for each of the detected at least one feature, a location difference between the determined respective location and a corresponding annotated location; and wherein changing a respective weighting of each of at least one synapse of the neural network includes changing the respective weighting in response to the location difference.

Example 62 includes the method of any of Examples 55-61, further comprising: repeating determining a respective probability, determining a probability difference, and changing a respective weighting for at least one iteration, for one or more additional iterations; generating, after each iteration, a respective training model for the neural network; and configuring the neural network in response to the one of the training models that yields a highest value of a metric.

Example 63 includes the method of any of Examples 55-62, further comprising: repeating determining a respective probability, determining a probability difference, and changing a respective weighting for at least one iteration, for one or more additional iterations; generating, after each iteration, a respective training model for the neural network; and configuring the neural network in response to the one of the training models that yields a highest value of a weighted F1 metric.

Example 64 includes the method of any of Examples 55-63, further comprising: repeating determining a respective probability, determining a probability difference, and changing a respective weighting for at least one iteration, for one or more additional iterations; generating, after each iteration for which the probability difference is less than or equal to a threshold, a respective training model for the neural network; and configuring the neural network in response to the one of the training models that yields a highest value of a metric.

Example 65 includes a system, comprising: an electronic circuit configured to execute a neural network; to detect at least one feature in an image of a body portion while executing the neural network; and to determine a respective position and a respective class of each of the detected at least one feature while executing the neural network.

Example 66 includes the system of Example 65 wherein the neural network includes a convolutional neural network.

Example 67 includes the system of any of Examples 65-66 wherein the neural network includes a single-shot-detector convolutional neural network.

Example 68 includes the system of any of Examples 65-67, further comprising an ultrasound transducer coupled to the electronic circuit and configured to acquire the image.

Example 69 includes the system of any of Examples 65-68 wherein the electronic circuit, while executing the neural network, is configured to detect at least one feature in an ultrasound image of a lung.

Example 70 includes the system of any of Examples 65-69 wherein the electronic circuit, while executing the neural network, is configured to determine a respective position of each of the detected at least one feature by determining a respective container that bounds the detected feature.

Example 71 includes the system of any of Examples 65-70 wherein the electronic circuit, while executing the neural network, is configured to determine a respective position of each of the detected at least one feature by determining a respective bounding box in which the feature is disposed.

Example 72 includes the system of any of Examples 65-71 wherein the electronic circuit, while executing the neural network, is configured to determine a respective position of each of the detected at least one feature by determining a coordinate of a respective bounding box in which the feature is disposed.

Example 73 includes the system of any of Examples 65-72 wherein the electronic circuit, while executing the neural network, is configured to determine a respective position of each of the detected at least one feature by determining a size of a respective bounding box in which the feature is disposed.

Example 74 includes the system of any of Examples 65-73 wherein the electronic circuit, while executing the neural network, is configured to determine a respective class of each of the detected at least one feature by determining a respective probability that the feature belongs to the respective class.

Example 75 includes the system of any of Examples 65-74 wherein the electronic circuit, while executing the neural network, is configured to determine a respective class of each of the detected at least one feature by determining a respective confidence level that the feature belongs to the respective class.

Example 76 includes the system of any of Examples 65-75 wherein the electronic circuit, while executing the neural network, is configured to determine a respective class of each of the detected at least one feature by: determining a respective probability that the feature belongs to the respective class; and determining that the feature belongs to the respective class in response to the respective probability being greater than a threshold for the respective class.

Example 77 includes the system of any of Examples 65-76 wherein the electronic circuit, while executing the neural network, is configured to determine a respective class of each of the detected at least one feature by: determining probabilities that the detected at least one feature belongs to respective classes; and determining that the feature belongs to the one of the respective classes corresponding to the highest one of the probabilities.

Example 78 includes the system of any of Examples 65-77 wherein the electronic circuit, while executing the neural network, is configured to determine a respective class of each of the detected at least one feature by determining whether at least one of the detected at least one feature includes an A-line.

Example 79 includes the system of any of Examples 65-78 wherein the electronic circuit, while executing the neural network, is configured to determine a respective class of each of the detected at least one feature by determining whether at least one of the detected at least one feature includes a pleural line.

Example 80 includes the system of any of Examples 65-79 wherein the electronic circuit, while executing the neural network, is configured to determine a respective class of each of the detected at least one feature by determining whether at least one of the detected at least one feature includes a pleural effusion.

Example 81 includes the system of any of Examples 65-80 wherein the electronic circuit, while executing the neural network, is configured to determine a respective class of each of the detected at least one feature by determining whether at least one of the detected at least one feature includes a B-line.

Example 82 includes the system of any of Examples 65-81 wherein the electronic circuit, while executing the neural network, is configured to determine a respective class of each of the detected at least one feature by determining whether at least one of the detected at least one feature includes merged B-lines.

Example 83 includes the system of any of Examples 65-82 wherein the electronic circuit, while executing the neural network, is configured: to receive at least one other image of the body portion; to detect at least one respective feature in each of multiple ones of the images; to determine which of the detected at least one respective feature is a respective detected B-line, and a respective position of each of the detected B-lines; to group multiple detected B-lines in at least one cluster in response to the respective positions of the detected B-lines, each cluster corresponding to a respective actual B-line; and to determine a respective position of each actual B-line in response to a corresponding one of the at least one cluster.

Example 84 includes the system of any of Examples 65-83 wherein the electronic circuit, while executing the neural network, is configured to determine a respective class of each of the detected at least one feature by determining that at least one of the detected at least one feature includes a consolidation.

Example 85 includes the system of any of Examples 65-84 wherein the electronic circuit, while executing the neural network, is configured: to determine a respective class of each of the detected at least one feature by determining that at least one of the detected at least one feature includes a pleural effusion; and to determine a severity of the pleural effusion.

Example 86 includes the system of any of Examples 65-85 wherein: the image of the body portion includes an image of a lung; and the electronic circuit is configured to diagnose a pathology of the lung in response to the respective determined class of each of the detected at least one feature.

Example 87 includes the system of any of Examples 65-86 wherein: the image of the body portion includes an image of a lung; and the electronic circuit is configured to diagnose a pathology of the lung in response to the respective position and to the respective determined class of each of the detected at least one feature.

Example 88 includes the system of any of Examples 65-87 wherein the electronic circuit includes a control circuit.

Example 89 includes the system of any of Examples 65-88 wherein the electronic circuit includes a microprocessor.

Example 90 includes the system of any of Examples 65-89 wherein the electronic circuit includes a microcontroller.

Example 91 includes a system, comprising: an electronic circuit configured to execute a classifier neural network, to receive, while executing the classifier neural network, an image of a body portion, and to determine, while executing the classifier neural network, a probability that the image includes a feature belonging to a particular class.

Example 92 includes the system of Example 91 wherein the electronic circuit is configured to receive, while executing the classifier neural network, a time sequence of images of the body portion, the time sequence of images including the image, and to determine, while executing the classifier neural network, the probability that the images indicate the state of the function of the body portion.

Example 93 includes the system of any of Examples 91-92 wherein the electronic circuit is configured to receive, while executing the classifier neural network, a video of the body portion, the video including the image, and to determine, while executing the classifier neural network, the probability that the video indicates the state of the function of the body portion.

Example 94 includes the system of any of Examples 91-93 wherein the image includes an M-mode image.

Example 95 includes the system of any of Examples 91-94 wherein the state of the function can be function exhibited or function not exhibited.

Example 96 includes the system of any of Examples 91-95 wherein the body portion includes a lung and the function is lung sliding.

Example 97 includes the system of any of Examples 91-96 wherein the particular class is lung sliding.

Example 98 includes the system of any of Examples 91-97, wherein the electronic circuit, while executing the neural network, is configured to determine that the image indicates a state of a function belonging to the particular class in response to the probability being greater than or equal to a threshold.

Example 99 includes the system of any of Examples 91-98 wherein the electronic circuit includes a control circuit.

Example 100 includes the system of any of Examples 91-99 wherein the electronic circuit includes a microprocessor.

Example 101 includes the system of any of Examples 91-100 wherein the electronic circuit includes a microcontroller.

Example 102 includes a system, comprising: an electronic circuit configured to execute a neural network having input channels, and, while executing the neural network, configured to receive each of an image of a body portion and at least one modified version of the image with a respective input channel, to detect at least one feature in the image in response to the image and the at least one modified version of the image; and to determine a respective position and a respective class of each of the detected at least one feature in response to the image and the at least one modified version of the image.

Example 103 includes the system of Example 102 wherein the electronic circuit, while executing the neural network, is configured to generate, in response to the image of the body portion, the at least one modified version of the image.

Example 104 includes the system of any of Examples 102-103 wherein the image of the body portion includes an image of a lung.

Example 105 includes the system of any of Examples 102-104 wherein the electronic circuit, while executing the neural network, is configured to generate the at least one modified version of the image by generating at least one filtered version of the image.

Example 106 includes the system of any of Examples 102-105 wherein the neural network includes a convolutional neural network.

Example 107 includes the system of any of Examples 102-106 wherein the neural network includes a single-shot-detector convolutional neural network.

Example 108 includes the system of any of Examples 102-107 wherein the electronic circuit, while executing the neural network, is configured to determine a respective position of each of the detected at least one feature by determining a respective container that bounds the detected feature.

Example 109 includes the system of any of Examples 102-108 wherein the electronic circuit, while executing the neural network, is configured to determine a respective position of each of the detected at least one feature by determining a respective bounding box in which the feature is disposed.

Example 110 includes the system of any of Examples 102-109 wherein the electronic circuit, while executing the neural network, is configured to determine a respective position of each of the detected at least one feature by determining a coordinate of a respective bounding box in which the feature is disposed.

Example 111 includes the system of any of Examples 102-110 wherein the electronic circuit, while executing the neural network, is configured to determine a respective position of each of the detected at least one feature by determining a size of a respective bounding box in which the feature is disposed.

Example 112 includes the system of any of Examples 102-111 wherein the electronic circuit, while executing the neural network, is configured to determine a respective class of each of the detected at least one feature by determining a respective probability that the feature belongs to the respective class.

Example 113 includes the system of any of Examples 102-112 wherein the electronic circuit, while executing the neural network, is configured to determine a respective class of each of the detected at least one feature by determining a respective confidence level that the feature belongs to the respective class.

Example 114 includes the system of any of Examples 102-113 wherein the electronic circuit, while executing the neural network, is configured to determine a respective class of each of the detected at least one feature: by determining a respective probability that the feature belongs to the respective class; and by determining that the feature belongs to the respective class in response to the respective probability being greater than a threshold for the respective class.

Example 115 includes the system of any of Examples 102-114 wherein the electronic circuit, while executing the neural network, is configured to determine a respective class of each of the detected at least one feature: by determining probabilities that the detected at least one feature belongs to respective classes; and by determining that the feature belongs to the one of the respective classes corresponding to the highest one of the probabilities.

Example 116 includes the system of any of Examples 102-115 wherein the electronic circuit, while executing the neural network, is configured to determine a respective class of each of the detected at least one feature by determining whether at least one of the detected at least one feature includes an A-line.

Example 117 includes the system of any of Examples 102-116 wherein the electronic circuit, while executing the neural network, is configured to determine a respective class of each of the detected at least one feature by determining whether at least one of the detected at least one feature includes a pleural line.

Example 118 includes the system of any of Examples 102-117 wherein the electronic circuit, while executing the neural network, is configured to determine a respective class of each of the detected at least one feature by determining whether at least one of the detected at least one feature includes a pleural effusion.

Example 119 includes the system of any of Examples 102-118 wherein the electronic circuit, while executing the neural network, is configured to determine a respective class of each of the detected at least one feature by determining whether at least one of the detected at least one feature includes a B-line.

Example 120 includes the system of any of Examples 102-119 wherein the electronic circuit, while executing the neural network, is configured to determine a respective class of each of the detected at least one feature by determining whether at least one of the detected at least one feature includes merged B-lines.

Example 121 includes the system of any of Examples 102-120 wherein the electronic circuit, while executing the neural network, is configured to determine a respective class of each of the detected at least one feature by determining whether at least one of the detected at least one feature includes a consolidation.

Example 122 includes the system of any of Examples 102-121 wherein the electronic circuit, while executing the neural network, is configured: to determine a respective class of each of the detected at least one feature by determining whether at least one of the detected at least one feature includes a pleural effusion; and determining a severity of a detected pleural effusion.

Example 123 includes the system of any of Examples 102-122 wherein: the image of the body portion includes an image of a lung; and the electronic circuit is configured to diagnose a pathology of the lung in response to the respective determined class of each of the detected at least one feature.

Example 124 includes the system of any of Examples 102-123 wherein: the image of the body portion includes an image of a lung; and the electronic circuit is configured to diagnose a pathology of the lung in response to the respective position and to the respective determined class of each of the detected at least one feature.

Example 125 includes the system of any of Examples 102-124 wherein the electronic circuit includes a control circuit.

Example 126 includes the system of any of Examples 102-125 wherein the electronic circuit includes a microprocessor.

Example 127 includes the system of any of Examples 102-126 wherein the electronic circuit includes a microcontroller.

Example 128 includes a system, comprising: an electronic circuit configured to execute a neural network and configured, while executing the neural network, to receive an image of a body portion, the image including at least one feature belonging to a class, to detect at least one feature in the image; and to determine, for each of the detected at least one feature, a respective position and a respective confidence level that the respective one of the detected at least one feature belongs to the class.

Example 129 includes the system of Example 128 wherein the electronic circuit, while executing the neural network, is configured to detect the at least one feature and to determine the respective position and the respective confidence level in response to the image.

Example 130 includes the system of any of Examples 128-129 wherein the electronic circuit, while executing the neural network, is configured to determine, for each of the detected at least one feature, a respective one or more confidence levels that the respective one of the at least one feature belongs to one or more other classes.

Example 131 includes the system of any of Examples 128-130 wherein the electronic circuit, while executing the neural network, is configured: to receive at least one modified version of the image with the neural network; to detect the at least one feature in the image in response to the at least one modified version of the image; and to determine, for each of the detected at least one feature, the respective position and the respective confidence level in response to the at least one modified version of the image.

Example 132 includes the system of any of Examples 128-131 wherein the electronic circuit, while executing the neural network, is configured: to receive at least one modified version of the image with the neural network; to detect the at least one feature in the image in response to the image and the at least one modified version of the image; and to determine, for each of the detected at least one feature, the respective position and the respective confidence level in response to the image and the at least one modified version of the image.

Example 133 includes the system of any of Examples 128-132 wherein the electronic circuit includes a control circuit.

Example 134 includes the system of any of Examples 128-133 wherein the electronic circuit includes a microprocessor.

Example 135 includes the system of any of Examples 128-134 wherein the electronic circuit includes a microcontroller.

Example 136 includes a system, comprising: an electronic circuit configured to generate, from each of at least one first training image, at least one second training image, and to train a neural network by executing the neural network to determine a respective probability that each of at least one feature in at least one of the at least one first training image and the at least one second training image belongs to a feature class, by determining, for each of the at least one feature, a probability difference between the determined respective probability and a corresponding annotated probability, and by changing a respective weighting of each of at least one synapse of the neural network in response to the probability difference.

Example 137 includes the system of Example 136 wherein the electronic circuit is configured to generate the at least one second training image by adding noise to one of the at least one first training image.

Example 138 includes the system of any of Examples 136-137 wherein the electronic circuit is configured to generate the at least one second training image by altering a respective brightness of at least one pixel of one of the at least one first training image.

Example 139 includes the system of any of Examples 136-138 wherein the electronic circuit is configured to generate the at least one second training image by altering a respective contrast of one of the at least one first training image.

Example 140 includes the system of any of Examples 136-139 wherein the electronic circuit is configured to generate the at least one second training image by rotating one of the at least one first training image.

Example 141 includes the system of any of Examples 136-140 wherein the electronic circuit is configured to generate the at least one second training image by adding at least one artifact to one of the at least one first training image.

Example 142 includes the system of any of Examples 136-141 wherein the electronic circuit is further configured to train the neural network: by executing the neural network to detect each of the at least one feature; by executing the neural network to determine a respective location of each of the detected at least one feature; by executing the neural network to determine, for each of the detected at least one feature, a location difference between the determined respective location and a corresponding annotated location; and by changing the respective weighting of each of at least one synapse of the neural network in response to the location difference.

Example 143 includes the system of any of Examples 136-142 wherein the electronic circuit is further configured to train the neural network: by executing the neural network to repeat determining a respective probability, determining a probability difference, and changing a respective weighting for at least one iteration, for one or more additional iterations; by generating, after each iteration, a respective training model for the neural network; and by configuring the neural network in response to the one of the training models that yields a highest value of a metric.

Example 144 includes the system of any of Examples 136-143 wherein the electronic circuitry is further configured to train the neural network: by executing the neural network to repeat determining a respective probability, determining a probability difference, and changing a respective weighting for at least one iteration, for one or more additional iterations; by generating, after each iteration, a respective training model for the neural network; and by configuring the neural network in response to the one of the training models that yields a highest value of a weighted F1 metric.

Example 145 includes the system of any of Examples 136-144 wherein the electronic circuitry is further configured to train the neural network: by executing the neural network to repeat determining a respective probability, determining a probability difference, and changing a respective weighting for at least one iteration, for one or more additional iterations; by generating, after each iteration for which the probability difference is less than or equal to a threshold, a respective training model for the neural network; and by configuring the neural network in response to the one of the training models that yields a highest value of a metric.

Example 146 includes a tangible, non-transitory computer-readable medium storing instructions that, when executed by a computing circuit, cause the computing circuit, or another circuit under control of the computing circuit, to execute a neural network: to detect at least one feature in an image of a body portion; and to determine a respective position and a respective class of each of the detected at least one feature.

Example 147 includes a tangible, non-transitory computer-readable medium storing instructions that, when executed by a computing circuit, cause the computing circuit, or another circuit under control of the computing circuit, to execute a classifier neural network: to determine a probability that an image of a body portion includes a feature belonging to a particular class.

Example 148 includes a tangible, non-transitory computer-readable medium storing instructions that, when executed by a computing circuit, cause the computing circuit, or another circuit under control of the computing circuit to execute a neural network: to receive each of an image of a body portion and at least one modified version of the image with a respective input channel; to detect at least one feature in the image in response to the image and the at least one modified version of the image; and to determine a respective position and a respective class of each of the detected at least one feature in response to the image and the at least one modified version of the image.

Example 149 includes a tangible, non-transitory computer-readable medium storing instructions that, when executed by a computing circuit, cause the computing circuit, or another circuit under control of the computing circuit to execute a neural network configured to detect, in an image of a body portion, at least one feature belonging to a class: to detect at least one feature in an image of a body portion; and to determine for each of the detected at least one feature a respective position and a respective confidence level that the respective one of the detected at least one feature belongs to the class.

Example 150 includes a tangible, non-transitory computer-readable medium storing instructions that, when executed by a computing circuit, cause the computing circuit, or another circuit under control of the computing circuit: to generate, from each of at least one first training image, at least one second training image; to determine, with a neural network, a respective probability that each of at least one feature in at least one of the at least one first training image and the at least one second training image belongs to a feature class; to determine, for each of the detected at least one feature, a probability difference between the determined respective probability and a corresponding annotated probability; and to change a respective weighting of each of at least one synapse of the neural network in response to the probability difference.

From the foregoing it will be appreciated that, although specific embodiments have been described herein for purposes of illustration, various modifications may be made without deviating from the spirit and scope of the disclosure. Furthermore, where an alternative is disclosed for a particular embodiment, this alternative may also apply to other embodiments even if not specifically stated. In addition, any described component or operation may be implemented/performed in hardware, software, firmware, or a combination of any two or more of hardware, software, and firmware. For example, any of one, more, or all of the above-described operations and functions can be performed by electronic circuitry that is hardwire configured to perform one or more operations or functions, that is configured to execute program instructions to perform one or more operations or functions, that is configured with firmware, or otherwise configured, to perform one or more operations or functions, or that is configured with a combination of two or more of the aforementioned configurations. For example, one or more of the components of FIG. 24 can include such electronic circuitry. And if a software, firmware, or logical structure is described as performing a function or yielding a result, such description includes a hardware structure executing software, or being configured with software or firmware, performing the function or yielding the result. Furthermore, one or more components of a described apparatus or system may have been omitted from the description for clarity or another reason. Moreover, one or more components of a described apparatus or system that have been included in the description may be omitted from the apparatus or system.

The invention claimed is:

1. A method, comprising:
   capturing an ultrasound video having a plurality of images of a body portion via an ultrasound transducer, wherein the images of the body portion includes an image of a lung;
   executing a neural network by an electronic circuit coupled to the ultrasound transducer, the electronic circuit is configured to execute the neural network to:
   detect at least one feature in each of the images;
   determine a respective position and a respective class of each of the detected at least one feature, determining a respective position including determining a respective bounding box in which the detected at least one feature is disposed and determining a respective class including determining a respective probability that the detected at least one feature belongs to the respective class;
   group the detected at least one feature in at least one cluster in response to the respective position and the respective class, each cluster corresponding to a respective actual feature; and
   determine a grade for the respective actual feature in response to the cluster in which the respective actual feature is grouped; and
   diagnosing a pathology of the lung in response to the respective determined class of each of the detected at least one feature;
   wherein each detection of the at least one feature is represented by an output having the respective probability, a respective coordinate and a respective width of the respective bounding box.

2. The method of claim 1 wherein the images of the body portion include an image of a lung.

3. The method of claim 1 wherein determining a respective position of each of the detected at least one feature includes determining a size of the respective bounding box in which the detected at least one feature is disposed.

4. The method of claim 1 wherein determining a respective class of each of the detected at least one feature includes:
   determining a respective probability that the detected at least one feature belongs to the respective class; and
   determining that the detected at least one feature belongs to the respective class in response to the respective probability being greater than a threshold for the respective class.

5. The method of claim 1 wherein determining a respective class of each of the detected at least one feature includes:
   determining probabilities that the detected at least one feature belongs to respective classes; and
   determining that the detected at least one feature belongs to the one of the respective classes corresponding to the highest one of the probabilities.

6. The method of claim 1 wherein determining a respective class of each of the detected at least one feature includes determining that at least one of the detected at least one feature includes an A-line.

7. The method of claim 1 wherein determining a respective class of each of the detected at least one feature includes determining that at least one of the detected at least one feature includes a pleural line.

8. The method of claim 1 wherein determining a respective class of each of the detected at least one feature includes determining that at least one of the detected at least one feature includes a pleural effusion.

9. The method of claim 1 wherein determining a respective class of each of the detected at least one feature includes determining that at least one of the detected at least one feature includes a B-line.

10. The method of claim 1 wherein determining a respective class of each of the detected at least one feature includes determining that at least one of the detected at least one feature includes merged B-lines.

11. The method of claim 1 wherein determining a respective class of each of the detected at least one feature includes determining that at least one of the detected at least one feature includes a consolidation.

12. The method of claim 1, further comprising:
wherein determining a respective class of each of the detected at least one feature includes determining that at least one of the detected at least one feature includes a pleural effusion; and
determining a severity of the pleural effusion.

13. The method of claim 1, further comprising:
wherein the images of the body portion includes an image of a lung; and
diagnosing a pathology of the lung in response to the respective determined class of each of the detected at least one feature.

14. The method of claim 1, further comprising:
wherein the images of the body portion includes an image of a lung; and
diagnosing a pathology of the lung in response to the respective position and to the respective determined class of each of the detected at least one feature.

15. A system, comprising:
an ultrasound transducer configured to acquire an ultrasound video having a plurality of images of a body portion, wherein the images of the body portion includes an image of a lung; and
an electronic circuit coupled to the ultrasound transducer configured
to execute a neural network;
to detect at least one feature in each of the images while executing the neural network;
to determine a respective position and a respective class of each of the detected at least one feature while executing the neural network, determining a respective position including determining a respective bounding box in which the detected at least one feature is disposed and determining a respective class including determining a respective probability that the detected at least one feature belongs to the respective class;
to group the detected at least one feature in at least one cluster in response to the respective position and the respective class while executing the neural network, each cluster corresponding to a respective actual feature;
to determine a grade for the respective actual feature in response to the cluster in which the respective actual feature is grouped while executing the neural network; and
to diagnose a pathology of the lung in response to the respective determined class of each of the detected at least one feature;
wherein each detection of the at least one feature is represented by an output having the respective probability, a respective coordinate and a respective width of the respective bounding box.

16. The system of claim 15 wherein the neural network includes a convolutional neural network.

17. The system of claim 15 wherein the neural network includes a single-shot-detector convolutional neural network.

18. The system of claim 15 wherein the electronic circuit, while executing the neural network, is configured to detect at least one feature in an ultrasound image of a lung.

19. The system of claim 15 wherein the electronic circuit includes a control circuit.

20. The system of claim 15 wherein the image includes an M-mode image.

21. The system of claim 15 wherein the body portion includes a lung and the function is lung sliding.

22. A tangible, non-transitory computer-readable medium storing instructions that, when executed by a computing circuit, cause the computing circuit, or another circuit under control of the computing circuit, to execute a neural network:
to detect at least one feature in each of images of a body portion acquired by an ultrasound transducer, wherein the images of the body portion includes an image of a lung; and
to determine a respective position and a respective class of each of the detected at least one feature, determining a respective position including determining a respective bounding box in which the detected at least one feature is disposed and determining a respective class including determining a respective probability that the detected at least one feature belongs to the respective class;
to group the detected at least one feature in at least one cluster in response to the respective position and the respective class, each cluster corresponding to a respective actual feature; and
to determine a grade for the respective actual feature in response to the cluster in which the respective actual feature is grouped; and
to diagnose a pathology of the lung in response to the respective determined class of each of the detected at least one feature;
wherein each detection of the at least one feature is represented by an output having the respective probability, a respective coordinate and a respective width of the respective bounding box.

* * * * *